(12) United States Patent
Begemann

(10) Patent No.: US 11,535,857 B2
(45) Date of Patent: Dec. 27, 2022

(54) INCREASING PLANT GROWTH AND YIELD BY USING AN ABC TRANSPORTER SEQUENCE

(71) Applicant: BENSON HILL, INC., St. Louis, MO (US)

(72) Inventor: Matthew Begemann, St. Louis, MO (US)

(73) Assignee: BENSON HILL, INC., St. Louis, MO (US)

( * ) Notice: Subject to any disclaimer, the term of this patent is extended or adjusted under 35 U.S.C. 154(b) by 0 days.

(21) Appl. No.: 16/615,682

(22) PCT Filed: May 21, 2018

(86) PCT No.: PCT/IB2018/053576
§ 371 (c)(1),
(2) Date: Nov. 21, 2019

(87) PCT Pub. No.: WO2018/215915
PCT Pub. Date: Nov. 29, 2018

(65) Prior Publication Data
US 2020/0208168 A1 Jul. 2, 2020

Related U.S. Application Data

(60) Provisional application No. 62/509,384, filed on May 22, 2017.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01)

(58) Field of Classification Search
None
See application file for complete search history.

(56) References Cited

U.S. PATENT DOCUMENTS 7,589,257 B2 * 9/2009 Hershey ............... C07K 14/415 800/295
9,273,323 B2 * 3/2016 Kim .................... C12N 15/8261

FOREIGN PATENT DOCUMENTS

| EP | 2 661 959 A1 | 11/2013 | |
|---|---|---|---|
| WO | WO 2011/061656 A1 | 5/2011 | |
| WO | WO 2017/070458 A2 | 4/2017 | |
| WO | WO-2017070458 A2 * | 4/2017 | ........... C07K 14/415 |

OTHER PUBLICATIONS

Vinod, K.K. "Enhancing Nutrient Starvation Tolerance in Rice". Genetic Manipulation in Plants for Mitigation of Climate Change. 6, 117-142. (Year: 2016).*
Bakhsh et al. "A Minireview: Rubisco Small Subunit as a Strong, Green Tissue-Specific Promoter". Arch Biol Sci. 63(2): 299-307. (Year: 2011).*
Martinoia et al. "Multifunctionality of plant ABC transporters—more than just detoxifiers". Planta. 214: 345-355. (Year: 2002).*
Kim, D., et al., "The ABC transporter AtPDR8 is a cadmium extrusion pump conferring heavy metal resistance". The Plant Journal (2007) 50: 207-218 (Year: 2007).*
DATABASE Geneseq, "Plant cytoplasm localized yield increasing sequence SEQ:7740," 2011, pp. 1-2.
Hwang, J., et al., "Plant ABC Transporters Enable Many Unique Aspects of a Terrestrial Plant's Lifestyle," *Molecular Plant*, 2016, vol. 9(3), pp. 338-355.
Kim, D., et al., "Overexpression of AtABCG36 improves drought and salt stress resistance in *Arabidopsis*" *Physiologia Plantarum*, 2010, vol. 139(2), pp. 170-180.

* cited by examiner

*Primary Examiner* — Matthew R Keogh
*Assistant Examiner* — David R Byrnes
(74) *Attorney, Agent, or Firm* — Womble Bond Dickinson (US) LLP

(57) ABSTRACT

Compositions and methods for improving plant growth are provided herein. Polynucleotides encoding ABC transporter proteins, polypeptides encompassing ABC transporter proteins, and expression constructs for expressing genes of interest whose expression may improve agronomic properties including but not limited to crop yield, biotic and abiotic stress tolerance, and early vigor, plants comprising the polynucleotides, polypeptides, and expression constructs, and methods of producing transgenic plants are also provided.

3 Claims, No Drawings
Specification includes a Sequence Listing.

INCREASING PLANT GROWTH AND YIELD BY USING AN ABC TRANSPORTER SEQUENCE

CROSS-REFERENCE TO RELATED APPLICATIONS

This application is a national stage filing under 35 U.S.C. 371 of PCT/IB2018/053576 filed May 21, 2018, which International Application was published by the International Bureau in English on Nov. 29, 2018, and application claims priority from U.S. Provisional Patent Application No. 62/509,384, filed May 22, 2017, which applications are hereby incorporated in their entirety by reference in this application.

FIELD OF THE INVENTION

The invention is drawn to compositions and methods for increasing plant growth and yield through expression of an ABC transporter gene in a plant.

BACKGROUND OF THE INVENTION

The ever-increasing world population and the dwindling supply of arable land available for agriculture fuels research towards developing plants with increased biomass and yield. Conventional means for crop and horticultural improvements utilize selective breeding techniques to identify plants having desirable characteristics. However, such selective breeding techniques have several drawbacks, namely that these techniques are typically labor intensive and result in plants that often contain heterogeneous genetic components that may not always result in the desirable trait being passed on from parent plants. Advances in molecular biology provide means to precisely modify the germplasm of plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

Traits of interest include plant biomass and yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance, photosynthetic carbon assimilation rates, and early vigor may also be important factors in determining yield. Optimizing the abovementioned factors may therefore contribute to increasing crop yield.

An increase in seed yield is a particularly important trait since the seeds of many plants are important for human and animal consumption. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. An increase in plant biomass is important for forage crops like alfalfa, silage corn and hay. Many genes are involved in the metabolic pathways that contribute to plant growth and development. Modulating the expression of one or more such genes in a plant can produce a plant with improved growth and development relative to a control plant, but often can produce a plant with impaired growth and development relative to a control plant. Therefore, methods to improve plant growth and development are needed.

SUMMARY OF THE INVENTION

Compositions and methods for regulating gene expression in a plant are provided. The methods increase plant growth resulting in higher crop yield. Such methods include increasing the expression of at least one ABC transporter gene in a plant of interest. The invention also encompasses constructs comprising a promoter that drives expression in a plant cell operably linked to an ABC transporter coding sequence. Compositions further comprise plants, plant seeds, plant organs, plant cells, and other plant parts that have increased expression of an ABC transporter sequence. The invention includes methods that can be utilized to increase expression of an ABC transporter gene in a plant. Such ABC transporter gene may be a native sequence or alternatively, may be a sequence that is heterologous to the plant of interest.

Embodiments of the invention include:
1. A method for increasing crop yield comprising transforming a plant with at least one ABC transporter protein-encoding sequence.
2. The method of embodiment 1, wherein said ABC transporter protein-encoding sequence comprises SEQ ID NO: 1, or encodes a protein selected from the group of SEQ ID NOs:2 and 15-103.
3. The method of embodiment 1, wherein said ABC transporter protein-encoding sequence encodes a protein with at least 80%, 90%, 95%, 96%, 97%, 98%, or 99% sequence identity to a sequence selected from the group of SEQ ID NOs:2 and 15-103, and that has ABC transporter function.
4. The method of embodiment 1, wherein said ABC transporter protein-encoding sequence encodes a protein with at least 80%, 85%, 90%, 95%, 96%, 97%, 98%, or 99% sequence positives relative to a sequence selected from the group of SEQ ID NOs:2 and 15-103, and that has ABC transporter function.
5. A plant having stably incorporated into its genome a promoter that drives expression in a plant operably linked to an ABC transporter protein-encoding sequence, wherein said promoter is heterologous to said ABC transporter protein-encoding sequence.
6. The plant of embodiment 5, wherein said ABC transporter protein-encoding sequence comprises SEQ ID NO: 1, or encodes a protein selected from the group of SEQ ID NOs:2 and 15-103.
7. The plant of embodiment 5, wherein said ABC transporter protein-encoding sequence encodes a protein with at least 80%, 85%, 90%, 95%, 96%, 97%, 98%, or 99% sequence identity to a sequence selected from the group of SEQ ID NOs:2 and 15-103, and that has ABC transporter function.
8. The plant of embodiment 5, wherein said ABC transporter protein-encoding sequence encodes a protein with at least 80%, 85%, 90%, 95%, 96%, 97%, 98%, or 99% sequence positives relative to a sequence selected from the group of SEQ ID NOs:2 and 15-103, and that has ABC transporter function.
9. Transformed seed of any one of the plants of embodiments 5-8.
10. The plant of any one of embodiments 5-8 wherein said plant is a monocot.
11. The plant of embodiment 10 wherein said plant is from the genus *Zea, Oryza, Triticum, Sorghum, Secale, Eleusine, Setaria, Saccharum, Miscanthus, Panicum, Pennisetum, Megathyrsus, Cocos, Ananas, Musa, Elaeis, Avena*, or *Hordeum*.
12. The plant of any one of embodiments 5-8 wherein said plant is a dicot.
13. The plant of embodiment 12 wherein said plant is from the genus *Glycine, Brassica, Medicago, Helianthus, Carthamus, Nicotiana, Solanum, Gossypium, Ipomoea, Manihot, Coffea, Citrus, Theobroma, Camellia, Persea, Ficus, Psidium, Mangifera, Olea, Carica, Anacardium, Macadamia, Prunus, Beta, Populus*, or *Eucalyptus*.
14. The plant of any one of embodiments 5-8 wherein said plant exhibits increased growth relative to a control plant.
15. The plant of any one of embodiments 5-8 wherein said plant exhibits increased biomass yield relative to a control plant.
16. The plant of any one of embodiments 5-8 wherein said plant exhibits increased seed yield relative to a control plant.
17. The method of any one of embodiments 1-4, wherein said ABC transporter protein-encoding sequence is expressed from a developmentally regulated promoter.
18. The method of embodiment 17, wherein said developmentally regulated promoter comprises SEQ ID NO:3 or SEQ ID NO:5.
19. The method of any one of embodiments 1-18, further comprising transforming a plant with at least one additional protein-encoding sequence.
20. The method of embodiment 19 wherein said at least one additional protein-encoding sequence is selected from the group of SEQ ID NOs:7 and 9, or encodes a protein with at least 90% identity to a sequence selected from the group of SEQ ID NOs:8 and 10.
21. The method of embodiment 19 or 20 wherein said at least one additional protein-encoding sequence encodes a protein selected from the group of SEQ ID NOs:8 and 10.
22. The plant of any one of embodiments 5-8, wherein said promoter that drives expression in a plant is a developmentally regulated promoter.
23. The plant of embodiment 22, wherein said developmentally promoter comprises SEQ ID NO:3 or SEQ ID NO:5.
24. The plant of embodiment 5 having stably incorporated into its genome a second promoter that drives expression in a plant operably linked to a second protein-encoding sequence, wherein said second promoter is heterologous to said second protein-encoding sequence.
25. The plant of embodiment 24 wherein said second protein-encoding sequence is selected from the group of SEQ ID NOs:7 and 9, or encodes a protein with at least 90% identity to a sequence selected from the group of SEQ ID NOs:8 and 10.
26. The plant of embodiment 24 or 25 wherein said second protein-encoding sequence encodes a protein selected from the group of SEQ ID NOs:8 and 10.
27. A DNA construct comprising, in operable linkage,
   a. A promoter that is functional in a plant cell and,
   b. A nucleic acid sequence encoding an ABC transporter protein.
28. The DNA construct of embodiment 27, wherein said nucleic acid sequence encoding an ABC transporter protein comprises SEQ ID NO: 1, or encodes a protein selected from the group consisting of SEQ ID NOs:2 and 15-103.
29. The DNA construct of embodiment 27 or 28, wherein said nucleic acid sequence encoding an ABC transporter protein encodes a protein with at least 80%, 85%, 90%, 95%, 96%, 97%, 98%, or 99% sequence identity to a sequence selected from the group of SEQ ID NOs:2 and 15-103, and that has ABC transporter function.
30. The DNA construct of embodiment 27 or 28, wherein said nucleic acid sequence encoding an ABC transporter protein encodes a protein with at least 80%, 85%, 90%, 95%, 96%, 97%, 98%, or 99% sequence positives relative to a sequence selected from the group of SEQ ID NOs:2 and 15-103, and that has ABC transporter function.
31. The DNA construct of embodiment 27 or 28, wherein said promoter that is functional in a plant cell is selected from the group of SEQ ID NOs:3 and 5.
32. The DNA construct of any one of embodiments 27-31, wherein said promoter is heterologous to said nucleic acid sequence encoding an ABC transporter protein.
33. A method for increasing crop yield comprising modulating the expression of at least one ABC transporter protein-encoding sequence in a plant.
34. The method of embodiment 33 wherein said modulating the expression comprises increasing the expression of at least one ABC transporter protein-encoding sequence in a plant.
35. The method of embodiment 34, wherein said increasing the expression comprises increasing the activity of a native ABC transporter sequence in said plant or increasing activity of a native ABC transporter protein-encoding sequence in said plant.
36. The plant of any one of embodiments 5-8, wherein said promoter that drives expression in a plant is active in leaf tissue.
37. The DNA construct of any one of embodiments 27-32, wherein said promoter that is functional in a plant cell is active in leaf tissue.

DETAILED DESCRIPTION OF THE INVENTION

Compositions and methods for increasing crop biomass and yield are provided. The methods include increasing the expression of at least one ABC transporter gene in a plant of interest. Crop yield is an extremely complex trait that results from the growth of a crop plant through all stages of its development and allocation of plant resources to the harvestable portions of the plant. In some crops including but not limited to maize and soybean, the primary harvestable portions may include seeds, with secondary applications from the remainder of the biomass (e.g., leaves and stems). In other crops including but not limited to sugarcane and alfalfa, the primary harvestable portions of the plant consist of the stems or entire above-ground portion of the plant. In other crops including but not limited to potato and carrot, the primary harvestable portions of the plant are found belowground. Regardless of the harvested portion(s) of the crop plant, the accumulation of harvestable biomass results from plant growth and allocation of photosynthetically fixed carbon to the harvested portion(s) of the plant. Plant growth may be manipulated by modulating the expression of one or more plant genes. This modulation can alter the function of one or more metabolic pathways that contributes to plant growth and accumulation of harvestable biomass.

Methods of the invention include the manipulation of plant growth for increased yield through modulation of the expression of one or more genes encoding an ABC transporter protein. In a preferred embodiment, the expression of an ABC transporter protein-encoding gene is upregulated relative to ABC transporter expression levels in a control plant, resulting in increased harvestable biomass in plants with increased ABC transporter expression relative to control plants. Any methods for increasing the activity or expression of an ABC transporter protein-encoding sequence in a plant are encompassed by the present invention.

The compositions of the invention include constructs comprising the coding sequence set forth in SEQ ID NO:1 or encoding a protein selected from the group of SEQ ID NOs:2 and 15-103 or variants thereof, operably linked to a promoter that is functional in a plant cell. By "promoter" is intended to mean a regulatory region of DNA that is capable of driving expression of a sequence in a plant or plant cell. It is recognized that having identified the ABC transporter protein sequences disclosed herein, it is within the state of the art to isolate and identify additional ABC transporter protein sequences and nucleotide sequences encoding ABC transporter protein sequences, for instance through BLAST searches, PCR assays, and the like.

The coding sequences of the present invention, when assembled within a DNA construct such that a promoter is operably linked to the coding sequence of interest, enable expression and accumulation of ABC transporter protein in the cells of a plant stably transformed with this DNA construct. "Operably linked" is intended to mean a functional linkage between two or more elements. For example, an operable linkage between a promoter of the present invention and a heterologous nucleotide of interest is a functional link that allows for expression of the heterologous nucleotide sequence of interest. Operably linked elements may be contiguous or non-contiguous. When used to refer to the joining of two protein coding regions, by operably linked is intended that the coding regions are in the same reading frame. The cassette may additionally contain at least one additional gene to be co-transformed into the plant. Alternatively, the additional gene(s) can be provided on multiple expression cassettes or DNA constructs. The expression cassette may additionally contain selectable marker genes.

In this manner, the nucleotide sequences encoding the ABC transporter proteins of the invention are provided in expression cassettes or expression constructs along with a promoter sequence of interest, typically a heterologous promoter sequence, for expression in the plant of interest. By "heterologous promoter sequence" is intended to mean a sequence that is not naturally operably linked with the ABC transporter protein-encoding nucleotide sequence. While the ABC transporter protein-encoding nucleotide sequence and the promoter sequence are heterologous to each other, either the ABC transporter protein-encoding nucleotide sequence or the heterologous promoter sequence may be homologous, or native, or heterologous, or foreign, to the plant host. It is recognized that the promoter may also drive expression of its homologous or native nucleotide sequence. In this case, the transformed plant will have a change in phenotype.

Fragments and variants of the polynucleotides and amino acid sequences of the present invention may also be expressed by promoters that are operable in plant cells. By "fragment" is intended a portion of the polynucleotide or a portion of the amino acid sequence. "Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. Fragments and variants of the polynucleotides disclosed herein can encode proteins that retain ABC transporter function.

"Variant" amino acid or protein is intended to mean an amino acid or protein derived from the native amino acid or protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, such as hydrolysis of ATP and transport of inorganic ions. Biologically active variants of a native polypeptide will have at least about 80%, 85%, 90%, 91%, 92%, 93%, 94%, 95%, 96%, 97%, 98%, 99% or more sequence identity to the amino acid sequence for the native sequence as determined by sequence alignment programs and parameters described herein. In some embodiments, the variant polypeptide sequences will comprise conservative amino acid substitutions. The number of such conservative amino acid substitutions, summed with the number of amino acid identities, can be used to calculate the sequence positives when this sum is divided by the total number of amino acids in the sequence of interest. Sequence positive calculations are performed on the NCBI BLAST server that can be accessed on the world wide web at blast.ncbi.nlm.nih-.gov/Blast.cgi. A biologically active variant of a protein of the invention may differ from that protein by as few as 1-15 amino acid residues, as few as 1-10, such as 6-10, as few as 5, as few as 4, 3, 2, or even 1 amino acid residue.

Amino acids can be generally categorized as aliphatic, hydroxyl or sulfur/selenium-containing, cyclic, aromatic, basic, or acidic and their amide. Without being limited by theory, conservative amino acid substitutions may be preferable in some cases to non-conservative amino acid substitutions for the generation of variant protein sequences, as conservative substitutions may be more likely than non-conservative substitutions to allow the variant protein to retain its biological activity. Polynucleotides encoding a polypeptide having one or more amino acid substitutions in the sequence are contemplated within the scope of the present invention. Table 1 below provides a listing of examples of amino acids belong to each class.

TABLE 1

Classes of Amino Acids

| Amino Acid Class | Example Amino Acids |
| --- | --- |
| Aliphatic | Gly, Ala, Val, Leu, Ile |
| Hydroxyl or sulfur/selenium-containing | Ser, Cys, Thr, Met, Sec |
| Cyclic | Pro |
| Aromatic | Phe, Tyr, Trp |
| Basic | His, Lys, Arg |
| Acidic and their Amide | Asp, Glu, Asn, Gln |

Variant sequences may also be identified by analysis of existing databases of sequenced genomes. In this manner, corresponding sequences can be identified and used in the methods of the invention.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM 120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Such genes and coding regions can be codon optimized for expression in a plant of interest. A "codon-optimized gene" is a gene having its frequency of codon usage designed to mimic the frequency of preferred codon usage of the host cell. Nucleic acid molecules can be codon optimized, either wholly or in part. Because any one amino acid (except for methionine and tryptophan) is encoded by a number of codons, the sequence of the nucleic acid molecule may be changed without changing the encoded amino acid. Codon optimization is when one or more codons are altered at the nucleic acid level such that the amino acids are not changed but expression in a particular host organism is increased. Those having ordinary skill in the art will recognize that codon tables and other references providing preference information for a wide range of organisms are available in the art (see, e.g., Zhang et al. (1991) *Gene* 105:61-72; Murray et al. (1989) *Nucl. Acids Res.* 17:477-508). Methodology for optimizing a nucleotide sequence for expression in a plant is provided, for example, in U.S. Pat. No. 6,015,891, and the references cited therein, as well as in WO 2012/142,371, and the references cited therein.

The nucleotide sequences of the invention may be used in recombinant polynucleotides. A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

By "altering" or "modulating" the expression level of a gene is intended that the expression of the gene is upregulated or downregulated. It is recognized that in some instances, plant growth and yield are increased by increasing the expression levels of one or more genes encoding ABC transporter proteins, i.e. upregulating expression. Likewise, in some instances, plant growth and yield may be increased by decreasing the expression levels of one or more genes encoding ABC transporter proteins, i.e. downregulating expression. Thus, the invention encompasses the upregulation or downregulation of one or more genes encoding ABC transporter proteins. Further, the methods include the upregulation of at least one gene encoding an ABC transporter protein and the downregulation of at least one gene encoding a second ABC transporter protein in a plant of interest. By modulating the concentration and/or activity of at least one of the genes encoding an ABC transporter protein in a transgenic plant is intended that the concentration and/or activity is increased or decreased by at least about 1%, about 5%, about 10%, about 20%, about 30%, about 40%, about 50%, about 60%, about 70%, about 80%, or about 90% or greater relative to a native control plant, plant part, or cell which did not have the sequence of the invention introduced.

It is recognized that the expression levels of the genes encoding ABC transporter proteins of the present invention can be controlled by the use of one or more promoters that are functional in a plant cell. The expression level of the ABC transporter protein-encoding gene of interest may be measured directly, for example, by assaying for the level of the ABC transporter gene transcript or of the encoded protein in the plant. Methods for such assays are well-known in the art. For example, Northern blotting or quantitative reverse transcriptase-PCR (qRT-PCR) may be used to assess transcript levels, while western blotting, ELISA assays, or enzyme assays may be used to assess protein levels. ABC transporter function can be assessed by, for example, the well-known ATPase assay (Glavinas et al 2008 *Expert Opinion on Drug Metabolism & Toxicology* 4:721-732).

A "subject plant or plant cell" is one in which genetic alteration, such as transformation, has been effected as to an ABC transporter protein-encoding gene of interest, or is a plant or plant cell which is descended from a plant or cell so altered and which comprises the alteration. A "control" or "control plant" or "control plant cell" provides a reference point for measuring changes in phenotype of the subject plant or plant cell. Thus, the expression levels of an ABC transporter protein-encoding gene of interest are higher or lower than those in the control plant depending on the methods of the invention.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

While the invention is described in terms of transformed plants, it is recognized that transformed organisms of the invention also include plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

To downregulate expression of an ABC transporter protein-encoding gene of interest, antisense constructions, complementary to at least a portion of the messenger RNA (mRNA) for the sequences of a gene of interest, particularly a gene encoding an ABC transporter protein of interest can be constructed. Antisense nucleotides are designed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85%, 90%, 95% or greater sequence identity to the corresponding sequences to be silenced may be used. Furthermore, portions of the antisense nucleotides may be used to disrupt the expression of the target gene.

The polynucleotides of the invention can be used to isolate corresponding sequences from other plants. In this manner, methods such as PCR, hybridization, and the like can be used to identify such sequences based on their sequence homology or identity to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have transcription activation or enhancer activities and which share at least 75% sequence identity to the sequences disclosed herein, or to variants or fragments thereof, are encompassed by the present invention.

Variant sequences can be isolated by PCR. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York).

Variant sequences may also be identified by analysis of existing databases of sequenced genomes. In this manner, corresponding sequences encoding ABC transporter proteins can be identified and used in the methods of the invention. The variant sequences will retain the biological activity of an ABC transporter protein (i.e., ATP hydrolysis and transport of inorganic ions). The present invention shows that, unexpectedly, certain novel expression strategies for ABC transporter protein overexpression can lead to increased biomass and seed yield.

The expression cassette will include in the 5'-3' direction of transcription, a transcriptional and translational initiation region, a polynucleotide encoding an ABC transporter protein of the present invention, and a transcriptional and translational termination region (i.e., termination region) functional in plants.

A number of promoters may be used in the practice of the invention. The polynucleotides encoding an ABC transporter protein of the invention may be expressed from a promoter with a constitutive expression profile. Constitutive promoters include the CaMV 35S promoter (Odell et al. (1985) *Nature* 313:810-812); rice actin (McElroy et al. (1990) *Plant Cell* 2:163-171); ubiquitin (Christensen et al.

(1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like.

Polynucleotides of the invention encoding ABC transporter proteins of the invention may be expressed from tissue-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Leaf-preferred promoters are also known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6): 1129-1138; and Matsuoka et al. (1993) *Proc. Natl. Acad. Sci. USA* 90(20):9586-9590.

Developmentally-regulated promoters may be desirable for the expression of a polynucleotide encoding an ABC transporter protein. Such promoters may show a peak in expression at a particular developmental stage. Such promoters have been described in the art, e.g., U.S. 62/029,068; Gan and Amasino (1995) *Science* 270: 1986-1988; Rinehart et al. (1996) *Plant Physiol* 112: 1331-1341; Gray-Mitsumune et al. (1999) *Plant Mol Biol* 39: 657-669; Beaudoin and Rothstein (1997) *Plant Mol Biol* 33: 835-846; Genschik et al. (1994) *Gene* 148: 195-202, and the like.

Promoters that are induced following the application of a particular biotic and/or abiotic stress may be desirable for the expression of a polynucleotide encoding an ABC transporter protein. Such promoters have been described in the art, e.g., Yi et al. (2010) *Planta* 232: 743-754; Yamaguchi-Shinozaki and Shinozaki (1993) *Mol Gen Genet* 236: 331-340; U.S. Pat. No. 7,674,952; Rerksiri et al. (2013) *Sci World J* 2013: Article ID 397401; Khurana et al. (2013) *PLoS One* 8: e54418; Tao et al. (2015) *Plant Mol Biol Rep* 33: 200-208, and the like.

Cell-preferred promoters may be desirable for the expression of a polynucleotide encoding an ABC transporter protein. Such promoters may preferentially drive the expression of a downstream gene in a particular cell type such as a mesophyll or a bundle sheath cell. Such cell-preferred promoters have been described in the art, e.g., Viret et al. (1994) *Proc Natl Acad USA* 91: 8577-8581; U.S. Pat. Nos. 8,455,718; 7,642,347; Sattarzadeh et al. (2010) *Plant Biotechnol J* 8: 112-125; Engelmann et al. (2008) *Plant Physiol* 146: 1773-1785; Matsuoka et al. (1994) *Plant J* 6: 311-319, and the like.

It is recognized that a specific, non-constitutive expression profile may provide an improved plant phenotype relative to constitutive expression of a gene or genes of interest. For instance, many plant genes are regulated by light conditions, the application of particular stresses, the circadian cycle, or the stage of a plant's development. These expression profiles may be important for the function of the gene or gene product in planta. One strategy that may be used to provide a desired expression profile is the use of synthetic promoters containing cis-regulatory elements that drive the desired expression levels at the desired time and place in the plant. Cis-regulatory elements that can be used to alter gene expression in planta have been described in the scientific literature (Vandepoele et al. (2009) *Plant Physiol* 150: 535-546; Rushton et al. (2002) *Plant Cell* 14: 749-762). Cis-regulatory elements may also be used to alter promoter expression profiles, as described in Venter (2007) *Trends Plant Sci* 12: 118-124.

Plant terminators are known in the art and include those available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

As indicated, the nucleotides encoding ABC transporter proteins of the present invention can be used in expression cassettes to transform plants of interest. Transformation protocols as well as protocols for introducing polypeptides or polynucleotide sequences into plants may vary depending on the type of plant or plant cell, i.e., monocot or dicot, targeted for transformation. The term "transform" or "transformation" refers to any method used to introduce polypeptides or polynucleotides into plant cells. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, Agrobacterium-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. "Stable transformation" is intended to mean that the nucleotide construct introduced into a plant integrates into the genome of the plant and is capable of being inherited by the progeny thereof.

The cells that have been transformed may be grown into plants in accordance with conventional ways. See, for example, McCormick et al. (1986) *Plant Cell Reports* 5:81-84. In this manner, the present invention provides transformed seed (also referred to as "transgenic seed") having a polynucleotide of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Elusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (Musa spp.), avocado (*Persea americana*), fig (*Ficus* casica), guava (*Psidium guajava*), mango (*Mangifera indica*), olive (*Olea europaea*), papaya (*Carica papaya*), cashew (*Anacardium occidentale*), macadamia (Macadamia *integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers.

In one embodiment, a construct containing a promoter that is operable in a plant cell, operably linked to a coding sequence encoding an ABC transporter protein of the present invention is used to transform a plant cell or cells. The transformed plant cell or cells are regenerated to produce transformed plants. These plants transformed with a construct comprising a functional promoter driving expression of an ABC transporter protein-encoding polynucleotide of the invention demonstrated increased plant yield, i.e., increased above-ground biomass and/or increased harvestable biomass and/or increased seed yield.

Now that it has been demonstrated that upregulation of ABC transporter increases plant yield, other methods for increasing expression of an endogenous ABC transporter sequence in a plant of interest can be used. The expression of an ABC transporter gene present in a plant's genome can be altered by inserting a transcriptional enhancer upstream of the ABC transporter gene present in the plant's genome. This strategy will allow the ABC transporter gene's expression to retain its normal developmental profile, while showing elevated transcript levels. This strategy will occur through the insertion of an enhancer element upstream of an ABC transporter gene of interest using a meganuclease designed against the genomic sequence of interest. Alternatively, a Cas9 endonuclease coupled with a guide RNA (gRNA) designed against the genomic sequence of interest, or a Cpf1 endonuclease coupled with a gRNA designed against the genomic sequence of interest, or a Csm1 endonuclease coupled with a gRNA designed against the genomic sequence of interest is used to effect the insertion of an enhancer element upstream of an ABC transporter gene of interest. Alternatively, a deactivated endonuclease (e.g., a deactivated Cas9, Cpf1, or Csm1 endonuclease) fused to a transcriptional enhancer element is targeted to a genomic location near the transcription start site for an ABC transporter gene of interest, thereby modulating the expression of said ABC transporter gene of interest (Piatek et al. (2015) *Plant Biotechnol J* 13:578-589).

Modulation of the expression of an ABC transporter protein-encoding gene may be achieved through the use of precise genome-editing technologies to modulate the expression of the endogenous sequence. In this manner, a nucleic acid sequence will be inserted proximal to a native plant sequence encoding the ABC transporter through the use of methods available in the art. Such methods include, but are not limited to, meganucleases designed against the plant genomic sequence of interest (D'Halluin et al (2013) *Plant Biotechnol J* 11: 933-941); CRISPR-Cas9, CRISPR-Cpf1, TALENs, and other technologies for precise editing of genomes (Feng et al. (2013) *Cell Research* 23:1229-1232, Podevin et al. (2013) *Trends Biotechnology* 31: 375-383, Wei et al. (2013) *J Gen Genomics* 40: 281-289, Zhang et al (2013) WO 2013/026740, Zetsche et al. (2015) *Cell* 163: 759-771, U.S. Provisional Patent Application 62/295,325); *N. gregoryi* Argonaute-mediated DNA insertion (Gao et al. (2016) *Nat Biotechnol* doi:10.1038/nbt.3547); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. (2011) *Plant J* 701:147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65; Puchta (2002) *Plant Mol Biol* 48:173-182). The insertion of said nucleic acid sequences will be used to achieve the desired result of overexpression, decreased expression, and/or altered expression profile of an ABC transporter gene.

Enhancers include any molecule capable of enhancing gene expression when inserted into the genome of a plant. Thus, an enhancer can be inserted in a region of the genome upstream or downstream of an ABC transporter sequence of interest to enhance expression. Enhancers may be cis-acting, and can be located anywhere within the genome relative to a gene for which expression will be enhanced. For example, an enhancer may be positioned within about 1 Mbp, within about 100 kbp, within about 50 kbp, about 30 kbp, about 20 kbp, about 10 kbp, about 5 kbp, about 3 kbp, or about 1kbp of a coding sequence for which it enhances expression. An enhancer may also be located within about 1500 bp of a gene for which it enhances expression, or may be directly proximal to or located within an intron of a gene for which it enhances expression. Enhancers for use in modulating the expression of an endogenous gene encoding an ABC transporter protein or homolog according to the present invention include classical enhancer elements such as the CaMV 35S enhancer element, cytomegalovirus (CMV) early promoter enhancer element, and the SV40 enhancer element, and also intron-mediated enhancer elements that enhance gene expression such as the maize shrunken-1 enhancer element (Clancy and Hannah (2002) *Plant Physiol.* 130(2):918-29). Further examples of enhancers which may be introduced into a plant genome to modulate expression include a PetE enhancer (Chua et al. (2003) *Plant Cell* 15:11468-1479), or a rice α-amylase enhancer (Chen et al. (2002) *J. Biol. Chem.*

277:13641-13649), or any enhancer known in the art (Chudalayandi (2011) *Methods Mol. Biol.* 701:285-300). In some embodiments, the present invention comprises a subdomain, fragment, or duplicated enhancer element (Benfrey et al. (1990) *EMBO J* 9:1677-1684).

Alteration of ABC transporter gene expression may also be achieved through the modification of DNA in a way that does not alter the sequence of the DNA. Such changes could include modifying the chromatin content or structure of the ABC transporter gene of interest and/or of the DNA surrounding the ABC transporter gene. It is well known that such changes in chromatin content or structure can affect gene transcription (Hirschhorn et al. (1992) *Genes and Dev* 6:2288-2298; Narlikar et al. (2002) *Cell* 108: 475-487). Such changes could also include altering the methylation status of the ABC transporter gene of interest and/or of the DNA surrounding the ABC transporter gene of interest. It is well known that such changes in DNA methylation can alter transcription (Hsieh (1994) *Mol Cell Biol* 14: 5487-5494). Targeted epigenome editing has been shown to affect the transcription of a gene in a predictable manner (Hilton et al. (2015) 33: 510-517). It will be obvious to those skilled in the art that other similar alterations (collectively termed "epigenetic alterations") to the DNA that regulates transcription of the ABC transporter gene of interest may be applied in order to achieve the desired result of an altered ABC transporter gene expression profile.

Alteration of ABC transporter gene expression may also be achieved through the use of transposable element technologies to alter gene expression. It is well understood that transposable elements can alter the expression of nearby DNA (McGinnis et al. (1983) *Cell* 34:75-84). Alteration of the expression of a gene encoding an ABC transporter may be achieved by inserting a transposable element upstream of the ABC transporter gene of interest, causing the expression of said gene to be altered.

Alteration of ABC transporter gene expression may also be achieved through expression of a transcription factor or transcription factors that regulate the expression of the ABC transporter gene of interest. It is well understood that alteration of transcription factor expression can in turn alter the expression of the target gene(s) of said transcription factor (Hiratsu et al. (2003) *Plant J* 34:733-739). Alteration of ABC transporter gene expression may be achieved by altering the expression of transcription factor(s) that are known to interact with an ABC transporter gene of interest (e.g., OCLI; Javelle et al (2010) *Plant Physiol* 154:273-286).

Alteration of ABC transporter gene expression may also be achieved through the insertion of a promoter upstream of the open reading frame encoding a native ABC transporter in the plant species of interest. This will occur through the insertion of a promoter of interest upstream of an ABC transporter protein-encoding open reading frame using a meganuclease designed against the genomic sequence of interest. This strategy is well-understood and has been demonstrated previously to insert a transgene at a predefined location in the cotton genome (D'Halluin et al. (2013) *Plant Biotechnol J* 11: 933-941). It will be obvious to those skilled in the art that other technologies can be used to achieve a similar result of insertion of genetic elements at a predefined genomic locus by causing a double-strand break at said predefined genomic locus and providing an appropriate DNA template for insertion (e.g., CRISPR-Cas9, CRISPR-cpfl, CRISPR-Csm1, TALENs, and other technologies for precise editing of genomes).

The following examples are offered by way of illustration and not by way of limitation. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1—Construction of ABC Transporter Plant Transformation Vectors

An open reading frame encoding a maize ABC transporter protein was synthesized. This open reading frame comprised SEQ ID NO: 1, encoding the protein sequence of SEQ ID NO:2. Appropriate restriction sites were included at the 5' and 3' ends of the coding sequence to allow this DNA to be cloned into plant transformation vectors that contained genetic elements suitable for controlling gene expression. In each plant transformation construct, the ABC transporter open reading frame was located downstream of a plant promoter and 5' untranslated region (5'UTR) and upstream of a 3'UTR. Table 2 summarizes the plant transformation constructs that were built containing an ABC transporter open reading frame.

TABLE 2

ABC transporter plant transformation constructs

| Construct ID | Promoter + 5'UTR | ORF | 3'UTR |
|---|---|---|---|
| 131220 | OsRbcS (SEQ ID NO: 5) | ABC transporter (SEQ ID NO: 1, encoding SEQ ID NO: 2) | OsRbcS (SEQ ID NO: 6) |
| 131223 | OsCA (SEQ ID NO: 3) | ABC transporter (SEQ ID NO: 1, encoding SEQ ID NO: 2) | OsCA (SEQ ID NO: 4) |
| 132137 | OsRbcS (SEQ. ID NO: 5) | ABC transporter (SEQ ID NO: 1, encoding SEQ ID NO: 2) | OsRbcS (SEQ ID NO: 6) |
| 132141 | OsCA (SEQ ID NO: 3) | ABC transporter (SEQ ID NO: 1, encoding SEQ ID NO: 2) | OsCA (SEQ ID NO: 4) |

In addition to the single-genic ABC transporter plant transformation constructs listed in Table 2, multigenic plant transformation constructs containing an ABC transporter gene cassette and a second linked cassette were also built. Table 3 summarizes the multigenic ABC transporter plant transformation constructs.

TABLE 3

ABC transporter multigenic plant transformation constructs

| Construct ID | Promoter + 5'UTR | ORF | 3'UTR | Promoter + 5'UTR | ORF | 3'UTR |
|---|---|---|---|---|---|---|
| 132232 | OsRbcS (SEQ ID NO: 5) | ABC transporter (SEQ ID NO: 1, encoding SEQ ID NO: 2) | OsRbcS (SEQ ID NO: 6) | ZmRbcS (SEQ ID NO: 11) | RbcS-ictB (SEQ ID NO: 9) | ZmRbcS (SEQ ID NO: 12) |
| 132234 | OsRbcS (SEQ ID NO: 5) | ABC transporter (SEQ ID NO: 1, encoding SEQ ID NO: 2) | OsRbcS (SEQ ID NO: 6) | 4xRGCGR (SEQ ID NO: 13) | Thioredoxin (SEQ ID NO: 7) | ZmCA1 (SEQ ID NO: 14) |

In addition to the gene cassettes described in Tables 2 and 3, each plant transformation construct listed in Tables 2 and 3 also contained a selectable marker cassette suitable for the selection of transformed plant cells and regeneration of plants following the introduction of the plant transformation vector, as described below. Each transformation vector was built in a plasmid that contained sequences suitable for plasmid maintenance in *E. coli* and in *Agrobacterium tumefaciens*. Following verification that the plant transformation constructs listed in Tables 2 and 3 contained the desired sequences, they were transformed into *A. tumefaciens* cells for plant transformation.

Example 2—Transformation of *Setaria viridis*

*A. tumefaciens* cells harboring ABC transporter plant transformation vectors were used to transform *S. viridis* cells according to a previously described method (PCT/US2015/43989, herein incorporated by reference). Following transformation of the *S. viridis* cells with the relevant plant transformation vectors and regeneration of *S. viridis* plants, PCR analyses were performed to confirm the presence of the gene(s) of interest in the *S. viridis* genome. Table 4 summarizes the transformation constructs used to transform *S. viridis*, along with the number of PCR-verified transgenic plants that resulted from transformation with each construct.

TABLE 4

Summary of *S. viridis* transformation with
ABC transporter plant transformation vectors

| Construct | # Events |
|---|---|
| 131223 | 25 |
| 131220 | 31 |

Example 3—Transformation of Maize (*Zea mays*

*A. tumefaciens* cells harboring construct 132141 (Table 2) were used to transform maize (*Zea mays* cv. B 104) cells suitable for regeneration on tissue culture medium. Following transformation of the maize cells and regeneration of maize plants, PCR analyses were performed to confirm the presence of the gene(s) of interest in the maize genome. Forty-five transformed events were produced and confirmed by molecular assays to comprise the gene of interest.

Example 4—Transformation of Rice (*Oryza sativa*

*A. tumefaciens* cells harboring ABC transporter plant transformation vectors are used to transform rice (*Oryza sativa* cv. Kitaake) cells suitable for regeneration on tissue culture medium. Following transformation of the rice cells with the relevant plant transformation vectors and regeneration of rice plants, PCR analyses are performed to confirm the presence of the gene(s) of interest in the rice genome.

Example 5—Characterization of Transgenic *S. viridis*

Following the transformation and regeneration of *S. viridis* plants transformed with an ABC transporter plant transformation vector, the T0-generation plants were cultivated to maturity to produce T1-generation seeds. T1-generation *S. viridis* plants harboring the ABC transporter gene cassette of interest were grown in a greenhouse setting to assess the effects of ABC transporter gene expression on plant growth and terminal above-ground biomass and seed yield. A randomized block design was used with a wild-type *S. viridis* border row to eliminate edge effects from the analysis. Null segregant plants were grown alongside the transgenic *S. viridis* plants in identical environmental conditions. Table 5 summarizes the results of the biomass and seed yield determinations made from experiments with T1-generation *S. viridis* plants harboring an ABC transporter gene cassette as a result of transformation (experiments S60 and S68). Experiment U16 shows the results of biomass and seed yield experiments with T2 generation *S. viridis* produced by self-pollination of the indicated T1 events. This table indicates the construct used for transformation, as described in Table 2, followed by the T0 event number from which the T1 seed was harvested.

TABLE 5

Summary of S. viridis greenhouse observations with T1-generation plants

| Experiment | Event | DW (g) | Seed Yield (g) | DW Change | Seed Change |
|---|---|---|---|---|---|
| S68 | 131220-14A | 1.96 ± 0.21 | 0.32 ± 0.04 | 6.70% | −12.70% |
|  | 131220-19B | 2.48 ± 0.08 | 0.52 ± 0.02 | 34.90% | 43.00% |
|  | 131220-26 | 2.29 ± 0.15 | 0.46 ± 0.04 | 24.90% | 27.30% |
|  | 131220-3 | 2.17 ± 0.12 | 0.36 ± 0.04 | 18.20% | −1.90% |
|  | 131220-9 | 2.10 ± 0.18 | 0.37 ± 0.05 | 14.60% | 2.80% |
|  | 131220-Null | 1.83 ± 0.29 | 0.36 ± 0.06 | n/a | n/a |
| S60 | 131223-1 | 3.46 ± 0.28 | 1.06 ± 0.10 | 4.53% | 0.95% |
|  | 131223-2 | 3.25 ± 0.24 | 1.03 ± 0.10 | −1.81% | −1.90% |
|  | 131223-4A | 3.23 ± 0.23 | 1.00 ± 0.09 | −2.42% | −4.76% |
|  | 131223-4B | 3.21 ± 0.34 | 0.98 ± 0.13 | −3.02% | −6.67% |
|  | 131223-5 | 2.94 ± 0.19 | 0.90 ± 0.08 | −11.18% | −14.29% |
|  | 131223-null | 3.31 ± 0.16 | 1.05 ± 0.06 | n/a | n/a |
| U16 | 131220-14A | 3.34 ± 0.16 | 0.61 ± 0.05 | 7.05% | −3.17% |
|  | 131220-19B | 3.45 ± 0.10 | 0.74 ± 0.05 | 10.58% | 17.46% |
|  | 131220-26 | 3.06 ± 0.14 | 0.68 ± 0.04 | −1.92% | 7.94% |
|  | 131220-3 | 2.72 ± 0.20 | 0.49 ± 0.05 | −12.82% | −22.22% |
|  | 131220-9 | 2.66 ± 0.16 | 0.52 ± 0.05 | −14.74% | −17.46% |
|  | 131220-null | 3.12 ± 0.10 | 0.63 ± 0.03 | n/a | n/a |
|  | WT | 2.71 ± 0.24 | 0.59 ± 0.06 | −13.14% | −6.35% |

In Table 5, the dry weight of the above-ground biomass is indicated in the DW column in grams. Similarly, the dry weight of the harvested seeds is indicated in grams in the Seed Yield column. The DW Change and Seed Change columns indicate the percent change in above-ground biomass and seed yield, respectively, relative to the null segregants from the 131220 construct. As this table shows, all five of the 131220 events tested in experiment S68 had increased above-ground biomass accumulation relative to null segregants; three of the five 131220 events tested had increased seed yield relative to null segregants. In experiment S60, one of five 131223 events tested produced increased biomass and seed yield relative to null segregant controls. In experiment U16, T2 generation events produced by self-pollination were tested for biomass production and seed yield. In these tests, event 14A again showed an increase in biomass production and decrease in seed yield relative to null segregants; event 19B showed increased biomass yield and seed production; and event 26 showed increased seed production relative to null segregants.

Example 6—Characterization of Transgenic Maize

T0-generation maize plants transformed with the ABC transporter plant transformation vector of interest and confirmed to contain the gene(s) of interest are grown to maturity in a greenhouse. When the T0 plants reach reproductive stages, they are pollinated by an appropriate inbred maize line to produce hybrid maize seeds. Alternatively, or in addition to pollination of the T0 transgenic maize plant, the pollen from the T0 is used to pollinate one or more inbred maize lines to produce hybrid maize seeds. The F1-generation hybrid seed resulting from these pollinations are planted in a field setting in two- or four-row plots and cultivated using standard agronomic practices. Plants are genotyped to determine which plants do and which do not contain the ABC transporter gene cassette and any other relevant gene cassettes (e.g., a selectable marker gene cassette) that were included in the ABC transporter plant transformation vector. Following the maturation of the maize plants, the seed is harvested. Seeds from the plants containing the ABC transporter gene cassette are pooled, as are seeds from the null segregant plants lacking the ABC transporter gene cassette. The seeds are weighed, and seed yields are calculated for the plants containing the ABC transporter gene cassette as well as for the null segregant plants lacking the ABC transporter gene cassette. Appropriate statistical analyses are performed to determine whether plants containing an ABC transporter gene cassette produce higher yields than those plants that lack an ABC transporter gene cassette.

Alternatively, T0-generation maize plants transformed with the ABC transporter plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. Pollen from homozygous T1 plants is used to pollinate one or more inbred maize lines to produce hybrid maize seeds. Pollen from null segregant plants is also used to pollinate one or more inbred maize lines to produce hybrid maize seeds. The resulting hybrid seeds are planted in a field setting in two- or four-row plots and cultivated using standard agronomic practices. Following the maturation of the maize plants, the seed is harvested. Seeds from the plants containing the ABC transporter gene cassette are pooled, as are seeds from the null segregant plants lacking the ABC transporter gene cassette. The seeds are weighed, and seed yields are calculated for the plants containing the ABC transporter gene cassette as well as for the null segregant plants lacking the ABC transporter gene cassette. Appropriate statistical analyses are performed to determine whether plants containing an ABC transporter gene cassette produce higher yields than those plants that lack an ABC transporter gene cassette.

Example 7—Characterization of Transgenic Rice

T0-generation rice plants transformed with the ABC transporter plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. The plants from each group are grown to maturity and allowed to self-pollinate to produce T2 seed. The T2 seed resulting from this self-pollination is harvested and weighed, and seed yields from homozygous, heterozygous, and null segregant plants are calculated. Appropriate statistical analyses are performed to determine whether plants containing an ABC transporter gene cassette produce higher yields than those plants that lack an ABC transporter gene cassette.

T1-generation plants grown from seed that resulted from self-pollination of T0-generation plants, or T2-generation plants grown from seed that resulted from self-pollination of homozygous T1-generation plants, are grown in a field setting. In the case of T2-generation plants, null-segregant T1-generation plants are also self-pollinated to produce T2-generation null plants as negative controls. The plants are cultivated using standard agronomic practices and allowed to reach maturity. Upon reaching maturity, the plants are allowed to self-pollinate. The seed resulting from these self-pollinations is harvested and weighed, and seed yields from homozygous, heterozygous, and null segregant plants are calculated. Appropriate statistical analyses are performed to determine whether plants containing an ABC transporter gene cassette produce higher yields than those plants that lack an ABC transporter gene cassette.

I claim:

1. A method for increasing crop yield of a plant from genus *Setaria* comprising transforming a plant with an ABC transporter protein-encoding sequence comprising SEQ ID NO: 1, or at least one ABC transporter protein-encoding sequence with at least 95% identity to SEQ ID NO: 1 that encodes a protein, wherein the ABC transporter protein-encoding sequence is operably linked to a heterologous promoter comprising SEQ ID NO: 5, and wherein the crop yield is increased by at least 24% as compared to a control plant.

2. A plant from genus *Setaria* having stably incorporated into its genome an ABC transporter protein-encoding sequence comprising SEQ ID NO: 1, or at least one ABC transporter protein-encoding sequence with at least 95% identity to SEQ ID NO: 1, wherein the ABC transporter protein-encoding sequence is operably linked to a heterologous promoter comprising SEQ ID NO: 5, wherein a yield of the plant is increased by at least 24% as compared to a control plant.

3. A seed from genus *Setaria* transformed with a ABC transporter protein-encoding sequence comprising SEQ ID NO: 1, or at least one ABC transporter protein-encoding sequence with at least 95% identity to SEQ ID NO: 1, wherein the ABC transporter protein-encoding sequence is operably linked to a heterologous promoter comprising SEQ ID NO: 5, and wherein a yield of a plant grown from said seed is increased by at least 24% as compared to a control plant.

* * * * *

SEQUENCE LISTING

```
<160> NUMBER OF SEQ ID NOS: 103

<210> SEQ ID NO 1
<211> LENGTH: 888
<212> TYPE: DNA
<213> ORGANISM: Zea mays
<220> FEATURE:
<221> NAME/KEY: misc_feature
<222> LOCATION: (1)..(888)
<223> OTHER INFORMATION: ABC Transporter

<400> SEQUENCE: 1
atggccggcg aagggaatgg ggatgaaggg tggaggcgga gcggcatcga ggtcagcgcc      60
ctgcagttcg gctacgacgg gcagccgccg ctcttcgcgc gcttcaacct ctgcgtcgca     120
cccggctccc gctgcctcct cgtcggcgcc aacggatcag gcaagaccac actcttgaag     180
attcttgcgg gaaagcatat ggttggagga agagatgtgg tccgtgtcct caatggttcc     240
gcttttcatg atacacagct agtgtgcaat ggtgaccttt cgtacttggg tggttcttgg     300
agccgtacta ttggttcagc tggggatgtt ccactgcaag gcgacttctc tgctgagcac     360 atgattttg gagttgatgg ggttgatcct gtcaggcgag agaagctggt tgatctgcta     420
gacattgatc tgcagtggcg catgcataaa gtttcagatg ggcagcgccg cagggtgcaa     480
atctgcatgg gtcttcttca tccatacaag gtgcttttgc tcgatgagat cacggttgat     540
ctggacgtgg tgaccaggat ggacctgctt ggtttcttca aggaagagtg cgagcagagg     600
gaagctacca tcgtgtacgc cacccatata tttgacggac tcgagacgtg ggctaccgac     660
tttgcgtaca tccaagaagg cgagctgaga aggtccggga gatactccga catcgaggag     720
ctaaggagcg ccaagaactt gctgtcggta gtcgagtcgt ggctgaggtc agagaccaaa     780
cttccgaaga aggaaccccc accacgtcct gagacccagg ccaggcgttc ctcgccgttc     840
gatgcttctc ctttccgttc gtcacgccac atggcctact accgttga                  888

<210> SEQ ID NO 2
<211> LENGTH: 295
<212> TYPE: PRT
<213> ORGANISM: Zea mays
<220> FEATURE:
<221> NAME/KEY: MISC_FEATURE
<222> LOCATION: (1)..(295)
<223> OTHER INFORMATION: ABC Transporter

<400> SEQUENCE: 2

Met Ala Gly Glu Gly Asn Gly Asp Glu Gly Trp Arg Arg Ser Gly Ile
1               5                   10                  15

Glu Val Ser Ala Leu Gln Phe Gly Tyr Asp Gly Gln Pro Pro Leu Phe
            20                  25                  30

Ala Arg Phe Asn Leu Cys Val Ala Pro Gly Ser Arg Cys Leu Leu Val
```

```
                 35                  40                  45
Gly Ala Asn Gly Ser Gly Lys Thr Thr Leu Leu Lys Ile Leu Ala Gly
 50                  55                  60

Lys His Met Val Gly Gly Arg Asp Val Val Arg Val Leu Asn Gly Ser
 65                  70                  75                  80

Ala Phe His Asp Thr Gln Leu Val Cys Asn Gly Asp Leu Ser Tyr Leu
                 85                  90                  95

Gly Gly Ser Trp Ser Arg Thr Ile Gly Ser Ala Gly Asp Val Pro Leu
                100                 105                 110

Gln Gly Asp Phe Ser Ala Glu His Met Ile Phe Gly Val Asp Gly Val
            115                 120                 125

Asp Pro Val Arg Arg Glu Lys Leu Val Asp Leu Leu Asp Ile Asp Leu
        130                 135                 140

Gln Trp Arg Met His Lys Val Ser Asp Gly Gln Arg Arg Arg Val Gln
145                 150                 155                 160

Ile Cys Met Gly Leu Leu His Pro Tyr Lys Val Leu Leu Leu Asp Glu
                165                 170                 175

Ile Thr Val Asp Leu Asp Val Val Thr Arg Met Asp Leu Leu Gly Phe
            180                 185                 190

Phe Lys Glu Glu Cys Glu Gln Arg Glu Ala Thr Ile Val Tyr Ala Thr
        195                 200                 205

His Ile Phe Asp Gly Leu Glu Thr Trp Ala Thr Asp Phe Ala Tyr Ile
    210                 215                 220

Gln Glu Gly Glu Leu Arg Arg Ser Gly Arg Tyr Ser Asp Ile Glu Glu
225                 230                 235                 240

Leu Arg Ser Ala Lys Asn Leu Leu Ser Val Val Glu Ser Trp Leu Arg
                245                 250                 255

Ser Glu Thr Lys Leu Pro Lys Lys Glu Pro Pro Arg Pro Glu Thr
            260                 265                 270

Gln Ala Arg Arg Ser Ser Pro Phe Asp Ala Ser Pro Phe Arg Ser Ser
        275                 280                 285

Arg His Met Ala Tyr Tyr Arg
    290                 295

<210> SEQ ID NO 3
<211> LENGTH: 1416
<212> TYPE: DNA
<213> ORGANISM: Oryza sativa
<220> FEATURE:
<221> NAME/KEY: promoter
<222> LOCATION: (1)..(1416)
<223> OTHER INFORMATION: OsCA promoter

<400> SEQUENCE: 3
atcttggcta tttcccatgg cttctccgct ctactcttgt ccctgtttgg atgacgccgt    60
ccagaccaag acatcaaaac ggggcgacac tgtgaggtta cggtgtcgcc attcgccaca   120
atgtgctcac catgtcacct tgtcgacatt tcgccgcata caagtcgctg tcgaccgcc    180 aggtgggccc cactgtgagc agcacgagtg tggcgcgtat ataaatttgt cggatggaga   240
ggcagctgaa ggttttttcgc catggcaact gcgtccttcg acatctgcgc gaaggttggg   300
ctcggaattt cgacaggata ctcacagcga aatcaatact ctgctatggc aaatggtacg   360
cactcgtttc gattgttctg ccttcttctg tttatttttt tttcccgtat gtagctgtag   420
ctgctgataa acgtgccatg tattccatct cgttcttgca agcagtttct tagatgagtt   480
aaaatatgta ttccatgtca actgttcact ttagttaggt agaactttct tacattatga   540
```

```
ttagttatct acttactctc tctgtccgat aataattatc gcattgattt tttttataat      600
gtttgatcat tcgtcttatt aaaaaaaatt atagaattat ttttttttatt ttgtttgtga      660 cttgctttat tatcaaaaaa ataatttaaa tatggcatat ctttttttat atttacaata      720
atttttcaaa aaagatgaat ggtcaaacgt tacacgaaaa aatcaaagcg accactattt      780
tggaatggaa gtagtacctg tagagaaaaa ttaaatatta gttcttaagt gagtgtggac      840
cgaaaaaatt ccttatttat cataaacacg ttttccaaac ttttaaatga tatgtttttt      900
taaatatata aatgaacatg ttctttcaaa aatcaaataa atcactttt caagtttgta      960 ctgattaata ctagactaat catttgctaa ttgtttatat tgttttactt gccatcataa     1020
ctcatgccaa attgcttttc caacccacc attagccgct gtggcaagct cagttgctag     1080
cttgaggagg actatacaaa gttgcacaca cgccatggta ctaacgagaa ctggaaaata     1140
tgttgactgg aaaaattgta tcagttcata ttagaaacaa attactgtca gaatgaggaa     1200
aaactcagtc catgccacta aaggcatcag atgcgaattg gcgctccttt ctcctttcaa     1260
ggagtaggca taaacatagg ctctgcagta gtttcatctg agacagtcgg cacgcggggg     1320
cgcgggcgtc tatttgttgc gcgcgcgggc gcggcggcga gacgcgtgtg tagctactgc     1380
tataaggagc gcgccgtgca ccgcctctca catcga                               1416

<210> SEQ ID NO 4
<211> LENGTH: 315
<212> TYPE: DNA
<213> ORGANISM: Oryza sativa
<220> FEATURE:
<221> NAME/KEY: misc_feature
<222> LOCATION: (1)..(315)
<223> OTHER INFORMATION: OsCA 3'UTR

<400> SEQUENCE: 4
gttcatccga ccgtccgtcc gttcagttcg tcagtttacg ccaacgcttt tgcataagta       60
ctacctgagg atatcgtccc cgatcatcga tgtgaacgcg tggagtacta ctacgtacgt      120
accggatggt tcgatatatg tgaatgctgt attaagtaat aacaagaaat atatctcctc      180
tactttttcc tgacgcggag ttgtactgcc tatgatgcat aatttgatcg cagtgtgatc      240
aaaagacatc agctataatg tcttaataat attattatga agagtttacc ttttttactac      300 cttttactct ggtaa                                                       315

<210> SEQ ID NO 5
<211> LENGTH: 1497
<212> TYPE: DNA
<213> ORGANISM: Oryza sativa
<220> FEATURE:
<221> NAME/KEY: promoter
<222> LOCATION: (1)..(1497)
<223> OTHER INFORMATION: OsRbcS promoter

<400> SEQUENCE: 5
gaaccatacg gaattgacgg accaattgtg catacggact tagctaaaat aattgttgat       60
ttttggcaat aagaaaagcg agtagcacat aaaatctaaa gtggatgagt aaagggacaa      120
aattttatac atgttcaggc cttctcgatg agaagtaata ctatactcct gttttgggga      180
ttatatttgt cagatgttgt atcaatctga cgatcgagtt atggttattg ttggcggctg      240
ttaaatatcg attttatgcc atcaataacct gtataattta tacagaaata ataaaacatt      300
caacatagtg gtaggcttta attctaacat attccataag tgttggtgta tatttggatg      360
```

```
caggtaataa accaccgaat taggaggaaa tctagactaa gttgaaggaa attttcatcc    420
atacaagtgt tgggcttttt aactccattt taacaccaaa atgcaagccc aaaaacctgc    480
gaaatggata aggcagactg agaaggaggc ccaggccaaa acttgggcca gttgggccaa    540
gccaggtttc ggccaaatcc tgatcatcgc tgttgatctc agggtttggc atggacgctc    600
ttgatttact cctgatggca gttgcagggc atttccgatc attcgcatgc tctacaacca    660
tcatacctac ttatttaagg agctctcatc ctcacttcat atcacacact ccaatcttga    720
gctgaattat aagaggctct attgtatttt attgtatact agaattaggg aaagattaag    780
gtcgtagaag aaatcggagg aattccggag ttatcggtga tccttttcta tttcttatac    840
tttgttattt gctttaatag aaatatcatt tcaagtaatt aagatttgtt tagtgagaac    900
tattattggc tagttcctaa ttagcgtatg agatcactgt tcactataat ccgttaaaat    960
atagtgattg ctttagtgag ttacaaacac tacagtagtt attgattgct taaacgtggt   1020
gtttagatag ttaatttcta gtggttgctg cgtatcccat agtacgttag aggcgggtgt   1080
agaggtggtg accgccctca agagcactta attcctcctt gtttgtgtac gtggtagagc   1140
gacatctggg aacagtgggt taccagtgcc tgaagtacca tgttaggatt aaaattgtaa   1200
cattgtttct cattagtaaa tcttctctac cctctaccca catttgcttt gtatccttgg   1260
tgaacctgaa gaggaactga acacacacgt tccatgagga agacactcag tactcaagcc   1320
ggaggcagca cactgcaact taagtttttc tatagctcct agcaagctag caatggctcc   1380
ctcggtgatg gcttcgtcgg ccacctccgt ggctcccttc caggggctca agtccactgc   1440
gggcctcccg gtgaaccgcc gctccagcag ctcgagcttt ggcaacgtca gcatcga      1497
```

<210> SEQ ID NO 6
<211> LENGTH: 1429
<212> TYPE: DNA
<213> ORGANISM: Oryza sativa
<220> FEATURE:
<221> NAME/KEY: misc_feature
<222> LOCATION: (1)..(1429)
<223> OTHER INFORMATION: OsRbcS 3'UTR

<400> SEQUENCE: 6

```
gttcgcgctt tcgttccttc gtgcatgttc tttctttttc tttttttttt gtgtgtccgt     60
gttaagctgc acgtaattgt tctctcgcgc tccgacctgc cgttgttgca agagtactac    120
tacaactatc ggtctatcgt tcggtgacgg tgagacaggg cacgtgaatg caagatctcc    180
ggctatacac acgtactcat gtaatatgat gcctagagca tatctgaatc cgtcgacaat    240
gaaattttgg ttttgcaaaa tgctggtatt tgtttatcat cctggcacgt gatatttgcc    300
tagagcatct aaatcacttt tacgaaatgt gcgcgtcaac aaactgatac ggcccaaatg    360
ccagaaatta ccagcatata tagccatatc aacttttgat tcgtatatat gaaggttgat    420
ttagttagag aaattcggtt gtgagagaag gaggctagca agattcggt tgatcaagct    480 gtaccgccag ccaggacgt gctgtgcgcg cggctgtgcc gcttgaccgc agaaccatac    540
ggaattgacg gaccaattgt gcatacggac ttagctaaaa taattgttga ttttggcaa    600 taagaaaagc gagtagcaca taaaatctaa agtggatgag taaagggaca aaattttata    660
catgttcagg ccttctcgat gagaagtaat actatactcc tgttttgggg attatatttg    720
tcagatgttg tatcaatctg acgatcgagt tatggttatt gttggcggct gttaaatatc    780
gattttatgc catcaatacc tgtataattt atacagaaat aataaaacat tcaacatagt    840
ggtaggcttt aattctaaca tattccataa gtgttggtgt atatttggat gcaggtaata    900
```

```
aaccaccgaa ttaggaggaa atctagacta agttgaagga aatttcatc catacaagtg      960 ttgggctttt taactccatt ttaacaccaa aatgcaagcc caaaaacctg cgaaatggat    1020
aaggcagact gagaaggagg cccaggccaa aacttgggcc agttgggcca agccaggttt    1080
cggccaaatc ctgatcatcg ctgttgatct cagggtttgg catggacgct cttgatttac    1140
tcctgatggc agttgcaggg catttccgat cattcgcatg ctctacaacc atcatacctc    1200
cttatttaag gagctctcat cctcacttca tatcacacac tccaatcttg agctgaatta    1260
taagaggctc tattgtattt tattgtatac tagaattagg gaaagattaa ggtcgtagaa    1320
gaaatcggag gaattccgga gttatcggtg atccttttct atttcttata ctttgttatt    1380
tgctttaata gaaatatcat ttcaagtaat taagatttgt ttagtgaga              1429
```

```
<210> SEQ ID NO 7
<211> LENGTH: 525
<212> TYPE: DNA
<213> ORGANISM: Zea mays
<220> FEATURE:
<221> NAME/KEY: misc_feature
<222> LOCATION: (1)..(525)
<223> OTHER INFORMATION: m-type thioredoxin

<400> SEQUENCE: 7
```

```
atggccctcg agacatgctt tagggcctgg gccctccacg ccgcgccagc cgggtccaag       60
gaccgcctcc tcgtgtgttc ctccgggggg aacctcgtcc tgccgtccaa gagggtcgcg      120
gccgcgccac tctccgtcgg cagggtcgcg accgccgcg cccgccatgt gtgccagtcc       180
aaaaatgcgg tcgatgaagt gctcgtcgcg gatgaaaaaa actgggatgg catggtcatg      240
gcgtgtgaga ccccagtgct ggtcgaattc tgggcccccat ggtgtgggcc gtgccgcatg    300
attgcgccgg tcatcgacga gctggcgaag gactatgcgg gcaaaattat gtgttgcaaa     360
gtcaatacag acgacagccc gaatgtcgcg tccacctacg gcattaggtc catcccaaca    420
gtgctcatct ttaaaggcgg cgagaagaaa gagagcgtca ttggcgcggt gccaaaaagc   480
acactcacaa ccctcatcga caaatatatc gggtccagct cctga                  525
```

```
<210> SEQ ID NO 8
<211> LENGTH: 174
<212> TYPE: PRT
<213> ORGANISM: Zea mays
<220> FEATURE:
<221> NAME/KEY: MISC_FEATURE
<222> LOCATION: (1)..(174)
<223> OTHER INFORMATION: m-type thioredoxin

<400> SEQUENCE: 8
```

```
Met Ala Leu Glu Thr Cys Phe Arg Ala Trp Ala Leu His Ala Ala Pro
1               5                   10                  15

Ala Gly Ser Lys Asp Arg Leu Leu Val Cys Ser Ser Gly Gly Asn Leu
            20                  25                  30

Val Leu Pro Ser Lys Arg Val Ala Ala Ala Pro Leu Ser Val Gly Arg
        35                  40                  45

Val Ala Thr Arg Arg Ala Arg His Val Cys Gln Ser Lys Asn Ala Val
    50                  55                  60

Asp Glu Val Leu Val Ala Asp Glu Lys Asn Trp Asp Gly Met Val Met
65                  70                  75                  80

Ala Cys Glu Thr Pro Val Leu Val Glu Phe Trp Ala Pro Trp Cys Gly
                85                  90                  95
```

```
Pro Cys Arg Met Ile Ala Pro Val Ile Asp Glu Leu Ala Lys Asp Tyr
            100                 105                 110

Ala Gly Lys Ile Met Cys Cys Lys Val Asn Thr Asp Asp Ser Pro Asn
        115                 120                 125

Val Ala Ser Thr Tyr Gly Ile Arg Ser Ile Pro Thr Val Leu Ile Phe
        130                 135                 140

Lys Gly Gly Glu Lys Lys Glu Ser Val Ile Gly Ala Val Pro Lys Ser
145                 150                 155                 160

Thr Leu Thr Thr Leu Ile Asp Lys Tyr Ile Gly Ser Ser Ser
                165                 170
```

<210> SEQ ID NO 9
<211> LENGTH: 1647
<212> TYPE: DNA
<213> ORGANISM: Synechococcus sp.
<220> FEATURE:
<221> NAME/KEY: misc_feature
<222> LOCATION: (1)..(1647)
<223> OTHER INFORMATION: RbcS-ictB
<220> FEATURE:
<221> NAME/KEY: sig_peptide
<222> LOCATION: (1)..(339)
<223> OTHER INFORMATION: P. sativum RbcS signal peptide

<400> SEQUENCE: 9

```
atggcttcta tgatttcttc ttctgctgtg acaacagtgt ctagggcttc tagggggccag    60 tctgctgctg tggctccttt cggcggcctc aagtctatga caggcttccc tgtgaagaag   120
gtgaatacag atattacatc tattacatct aatggcggca gggtgaagtg catgcaggtg   180
tggcctccta ttggcaagaa gaagttcgag acactctctt acctccctcc tctcacaagg   240
gatatgacag tgtggcagac actcacattc gctcattacc agcctcagca gtggggccat   300
tcttctttcc tccataggct cttcggctct ctcagggctt ggagggcttc ttctcagctc   360
ctcgtgtggt ctgaggctct cggcggcttc ctcctcgctg tggtgtacgg ctctgctcct   420
ttcgtgcctt cttctgctct cggcctcggc ctcgctgcta ttgctgctta ctgggctctc   480
ctctctctca cagatattga tctcaggcag gctacaccta tcattggct cgtgctcctc   540 tactggggcg tggatgctct cgctacaggc ctctctcctg tgaggctgc tgctctcgtg   600 ggcctcgcta agctcacact ctacctcctc gtgttcgctc tcgctgctag ggtgctcagg   660
aatcctaggc tcaggtctct cctcttctct gtggtggtga ttacatctct cttcgtgtct   720
gtgtacggcc tcaatcagtg gatttacggc gtggaggagc tcgctacatg ggtggatagg   780
aattctgtgg ctgatttcac atctagggtg tactcttacc tggcaatcc taatctcctc   840 gctgcttacc tcgtgcctac aacagctttc tctgctgctg ctattggcgt gtgagggggc   900
tggctcccta agctcctcgc tattgctgct acaggcgctc ttctctctg cctcattctc   960 acatactcta gggcggctg ctcggcttc gtggctatga ttttcgtgtg gctctcctc    1020 ggcctctact ggttccagcc taggctccct gctccttgga ggaggtggct cttccctgtg   1080
gtgctcggcg gcctcgtggc tgtgctcctc gtggctgtgc tcggcctcga gcctctcagg   1140
gtgagggtgc tctctatttt cgtgggcagg gaggattctt ctaataattt caggattaat   1200
gtgtggctcg ctgtgctcca gatgattcag gataggcctt ggctcggcat ggccctggc   1260 aatacagctt tcaatctcgt gtaccctctc taccagcagg ctaggttcac agctctctct   1320
gcttactctg tgcctctcga ggtggctgtg gagggcggcc tcctcggcct cacagctttc   1380
gcttggctcc tcctcgtgac agctgtgaca gctgtgcgcc aggtgtctag gctcaggagg   1440
```

```
gataggaatc ctcaggcttt ctggctcatg gcttctctcg ctggcctcgc tggcatgctc    1500
ggccatggcc tcttcgatac agtgctctac aggcctgagg cttctacact ctggtggctc    1560
tgcattggcg ctattgcttc tttctggcag cctcagcctt ctaagcagct ccctcctgag    1620
gctgagcatt ctgatgagaa gatgtga                                        1647
```

```
<210> SEQ ID NO 10
<211> LENGTH: 580
<212> TYPE: PRT
<213> ORGANISM: Synechococcus sp.
<220> FEATURE:
<221> NAME/KEY: MISC_FEATURE
<222> LOCATION: (1)..(580)
<223> OTHER INFORMATION: RbcS-ictB
<220> FEATURE:
<221> NAME/KEY: MISC_FEATURE
<222> LOCATION: (1)..(113)
<223> OTHER INFORMATION: P. sativum RbcS signal peptide

<400> SEQUENCE: 10

Met Pro Ser Val Trp Gly Ser Leu Leu Gln Asp Asp Pro Ser Lys Gln
1               5                   10                  15

Ala Ser Ser Glu Tyr Ile His Thr Arg Gln Pro Gly Ser Arg Leu Asn
            20                  25                  30

Met Ala Ser Met Ile Ser Ser Ala Val Thr Thr Val Ser Arg Ala
        35                  40                  45

Ser Arg Gly Gln Ser Ala Ala Val Ala Pro Phe Gly Gly Leu Lys Ser
    50                  55                  60

Met Thr Gly Phe Pro Val Lys Lys Val Asn Thr Asp Ile Thr Ser Ile
65                  70                  75                  80

Thr Ser Asn Gly Gly Arg Val Lys Cys Met Gln Val Trp Pro Pro Ile
                85                  90                  95

Gly Lys Lys Lys Phe Glu Thr Leu Ser Tyr Leu Pro Pro Leu Thr Arg
            100                 105                 110

Asp Met Thr Val Trp Gln Thr Leu Thr Phe Ala His Tyr Gln Pro Gln
        115                 120                 125

Gln Trp Gly His Ser Ser Phe Leu His Arg Leu Phe Gly Ser Leu Arg
    130                 135                 140

Ala Trp Arg Ala Ser Ser Gln Leu Leu Val Trp Ser Glu Ala Leu Gly
145                 150                 155                 160

Gly Phe Leu Leu Ala Val Val Tyr Gly Ser Ala Pro Phe Val Pro Ser
                165                 170                 175

Ser Ala Leu Gly Leu Gly Leu Ala Ala Ile Ala Ala Tyr Trp Ala Leu
            180                 185                 190

Leu Ser Leu Thr Asp Ile Asp Leu Arg Gln Ala Thr Pro Ile His Trp
        195                 200                 205

Leu Val Leu Leu Tyr Trp Gly Val Asp Ala Leu Ala Thr Gly Leu Ser
    210                 215                 220

Pro Val Arg Ala Ala Leu Val Gly Leu Ala Lys Leu Thr Leu Tyr
225                 230                 235                 240

Leu Leu Val Phe Ala Leu Ala Ala Arg Val Leu Arg Asn Pro Arg Leu
                245                 250                 255

Arg Ser Leu Leu Phe Ser Val Val Ile Thr Ser Leu Phe Val Ser
            260                 265                 270

Val Tyr Gly Leu Asn Gln Trp Ile Tyr Gly Val Glu Glu Leu Ala Thr
        275                 280                 285

Trp Val Asp Arg Asn Ser Val Ala Asp Phe Thr Ser Arg Val Tyr Ser
```

```
                290                 295                 300
Tyr Leu Gly Asn Pro Asn Leu Ala Ala Tyr Leu Val Pro Thr Thr
305                 310                 315                 320

Ala Phe Ser Ala Ala Ala Ile Gly Val Trp Arg Gly Trp Leu Pro Lys
                325                 330                 335

Leu Leu Ala Ile Ala Ala Thr Gly Ala Ser Ser Leu Cys Leu Ile Leu
                340                 345                 350

Thr Tyr Ser Arg Gly Gly Trp Leu Gly Phe Val Ala Met Ile Phe Val
                355                 360                 365

Trp Ala Leu Leu Gly Leu Tyr Trp Phe Gln Pro Arg Leu Pro Ala Pro
370                 375                 380

Trp Arg Arg Trp Leu Phe Pro Val Val Leu Gly Gly Leu Val Ala Val
385                 390                 395                 400

Leu Leu Val Ala Val Leu Gly Leu Glu Pro Leu Arg Val Arg Val Leu
                405                 410                 415

Ser Ile Phe Val Gly Arg Glu Asp Ser Ser Asn Asn Phe Arg Ile Asn
                420                 425                 430

Val Trp Leu Ala Val Leu Gln Met Ile Gln Asp Arg Pro Trp Leu Gly
                435                 440                 445

Ile Gly Pro Gly Asn Thr Ala Phe Asn Leu Val Tyr Pro Leu Tyr Gln
                450                 455                 460

Gln Ala Arg Phe Thr Ala Leu Ser Ala Tyr Ser Val Pro Leu Glu Val
465                 470                 475                 480

Ala Val Glu Gly Gly Leu Leu Gly Leu Thr Ala Phe Ala Trp Leu Leu
                485                 490                 495

Leu Val Thr Ala Val Thr Ala Val Arg Gln Val Ser Arg Leu Arg Arg
                500                 505                 510

Asp Arg Asn Pro Gln Ala Phe Trp Leu Met Ala Ser Leu Ala Gly Leu
                515                 520                 525

Ala Gly Met Leu Gly His Gly Leu Phe Asp Thr Val Leu Tyr Arg Pro
                530                 535                 540

Glu Ala Ser Thr Leu Trp Trp Leu Cys Ile Gly Ala Ile Ala Ser Phe
545                 550                 555                 560

Trp Gln Pro Gln Pro Ser Lys Gln Leu Pro Pro Glu Ala Glu His Ser
                565                 570                 575

Asp Glu Lys Met
            580

<210> SEQ ID NO 11
<211> LENGTH: 974
<212> TYPE: DNA
<213> ORGANISM: Zea mays
<220> FEATURE:
<221> NAME/KEY: promoter
<222> LOCATION: (1)..(974)
<223> OTHER INFORMATION: ZmRbcS promoter

<400> SEQUENCE: 11 gagctcccctt taatctggcg ctagatctgc atccgcggct tgcaaagata aatggcacat      60
ttagtgtgtt attttgcaat acctttcata gtagatatcc ttaaatgcag ttttaggcat     120
gtttgggtaa ttaaataaca ttttaggag gagttttaga tttacctttc tttcgtgatg      180
actgatgaca gacgtgggga attcaaatgc aactctagcg aaagttcata tattttcat      240 aaatagctga ggctgggta attatttttt ttgtagaaaa atagaatagg tggaatggtt      300
ggggaaggcg taggcgctcg tggacgacgc ccgataaaag acaagaggcg gaattgccat     360
```

```
gaattcgagg tagctaagta aggcgcatat atatgccaaa aaattctact gtcactttcc    420
aatttcaatg cgctgccaaa caagccatcc tggaaactga cttgaattca gcccaattct    480
gtagatccaa acagggccgg cgtcagtgcc tcaggtgaga gagcagcaga cgatgcaaag    540
agccaaaact gcaagcagac gcagccgaag ccgaagccga agcccaagcc caaaactgtt    600
ttgtctttgc ccagaaccgc gacgagccta aactgcgctt cctcctatct acaagtccct    660
ggcacatcac gcatagtcca accatggcgc gcaggcgata aggcgcgcca cggggacgcg    720
acatgtggtg gcggacgcga tcaggatagg gccaggctgg ccgggcgcgg ccacgggaga    780
acggtggcca ctcgtcccac atccgcttcg tcctgtcctg tactgcgtcc tgccccaac    840 gagagccgga gccggccatc ccgtcgcaca ctctcccct ctatatatgc cgtcggtgtg    900
ggggagccta ctacaggacg acccaagcaa gcaagcaagc agcgagtaca tacatactag    960
gcagccaggc agcc                                                     974

<210> SEQ ID NO 12
<211> LENGTH: 439
<212> TYPE: DNA
<213> ORGANISM: Zea mays
<220> FEATURE:
<221> NAME/KEY: misc_feature
<222> LOCATION: (1)..(439)
<223> OTHER INFORMATION: ZmRbcS 3'UTR

<400> SEQUENCE: 12
accgcgcccg ccggccgccc cccgccggct agctagctag ctagctcctg cgtgagctag     60
tagctagtgc catgcgtcgt ctctgtcgtt cggttttgct tcgggtcacc gtgtacccct    120
tgcttgcttg gtttcttctt tccttttttc cttttttttt cttcttttcc ccggccatgg    180
ttcctttgct ttccagcagt tctctgctgg atgtgatgta tccattgttg caatcatggc    240
cttgcattgg ctacctctat acctgctaca aaactactgc aacgcctata tatacttggg    300
gtgaggaaca tgtgaatgca agctccggct atcatataca tgtaatatgg atacaaacta    360
tatatataaa tccgccgagg cgccgacaat actatacgac accgtgttaa gttaatatat    420
aactggtgct ttttattta                                                 439

<210> SEQ ID NO 13
<211> LENGTH: 741
<212> TYPE: DNA
<213> ORGANISM: Sorghum bicolor
<220> FEATURE:
<221> NAME/KEY: promoter
<222> LOCATION: (1)..(741)
<223> OTHER INFORMATION: 4xRGCGR promoter

<400> SEQUENCE: 13
gaagcgagtg gcgcgctggc ggatgaggcg gcgagtggcc cggatgcacc ggcgcaggcg     60
agcgaagcga gtggcgcgct ggcggatgag gcggcgagtg gccccggatgc accggcgcag    120 gcgagcgaag cgagtggcgc gctggcggat gaggcggcga gtggcccgga tgcaccggcg    180
caggcgagcg aagcgagtgg cgcgctggcg gatgaggcgg cgagtggccc ggatgcaccg    240
gcgcaggcga gccgcacgcc gccgcccgcc cggcgctcg cgcgcgcacc gctgccgcct    300
gccgccacac aatgcgagcg cgcgcgcaca cacacacaca ccacccgggc gggggggctg    360
tagtagtaac ggccttgtct tgtcggcacg cgcgcgtccg tgtgtataag gaggcaggcc    420
cgcgacaacg ataagcggca ctcgcacgat caatgtacac attgcccgtc cgcgccacca    480
```

```
catccagcat cgtcgccagc ctcgccaccc ccgcgccgtc ctcctcctcc ggctccggct    540
ccggccgccc caggcccagg ctcatccgga acgccccgt cttcgccgcc ccgccaccg      600 tcgtgtaaac gggacggcgg gcagctgagg agtcaaacga gagagatcga gagaaagaaa   660
gggagggcat ccaccagccg ccggcgataa gaggggagga gagagaggcc agagaagagg   720
aggagaagaa gaagaaatcg a                                             741
```

```
<210> SEQ ID NO 14
<211> LENGTH: 287
<212> TYPE: DNA
<213> ORGANISM: Zea mays
<220> FEATURE:
<221> NAME/KEY: misc_feature
<222> LOCATION: (1)..(287)
<223> OTHER INFORMATION: ZmCA1 3'UTR

<400> SEQUENCE: 14
gttcaaaact agggctacgg caattctacc ggcccgccga ctcctgcatc atcataaata    60
tatatactat actatactac tacgtaccta ccgatatgca cccgagcaat gtgaatgcgt   120
cgagtactat atatctgttt tctgcatcta catatatata ccggatcaat cgcccaatgt   180
gaatgtaata agcaatatca ttttctacca cttttcattc ctaacgctga gcttttatg    240 tactatatct tatatgatga ataataatat gaccgccttg tgatcta                 287
```

```
<210> SEQ ID NO 15
<211> LENGTH: 295
<212> TYPE: PRT
<213> ORGANISM: Sorghum bicolor
<220> FEATURE:
<221> NAME/KEY: MISC_FEATURE
<222> LOCATION: (1)..(295)
<223> OTHER INFORMATION: ABC Transporter

<400> SEQUENCE: 15

Met Met Ala Gly Glu Gly Asn Gly Asp Glu Gly Trp Arg Arg Ser Gly
1               5                   10                  15

Ile Glu Val Ser Ala Leu Gln Phe Gly Tyr Asp Gly Gln Pro Pro Leu
            20                  25                  30

Phe Ala Arg Phe Asn Leu Arg Val Ala Pro Gly Ser Arg Cys Leu Leu
        35                  40                  45

Ile Gly Ala Asn Gly Ser Gly Lys Thr Thr Leu Leu Lys Ile Leu Ala
    50                  55                  60

Gly Lys His Met Val Gly Gly Arg Asp Val Val Arg Val Leu Asn Gly
65                  70                  75                  80

Ser Ala Phe His Asp Thr Gln Leu Val Cys Ser Gly Asp Leu Ser Tyr
                85                  90                  95

Leu Gly Gly Ser Trp Ser Arg Thr Ile Gly Ser Ala Gly Asp Val Pro
            100                 105                 110

Leu Gln Gly Asp Phe Ser Ala Glu His Met Ile Phe Gly Val Asp Gly
        115                 120                 125

Val Asp Pro Val Arg Arg Glu Lys Leu Val Asp Leu Leu Asp Ile Asp
    130                 135                 140

Leu Gln Trp Arg Met His Lys Val Ser Asp Gly Gln Arg Arg Arg Val
145                 150                 155                 160

Gln Ile Cys Met Gly Leu Leu His Pro Tyr Lys Val Leu Leu Leu Asp
                165                 170                 175

Glu Ile Thr Val Asp Leu Asp Val Val Thr Arg Met Asp Leu Leu Asp
            180                 185                 190
```

```
Phe Phe Lys Glu Glu Cys Glu Gln Arg Glu Ala Thr Ile Val Tyr Ala
            195                 200                 205

Thr His Ile Phe Asp Gly Leu Glu Thr Trp Ala Thr Asp Phe Ala Tyr
        210                 215                 220

Ile Gln Glu Gly Glu Leu Arg Arg Ser Gly Arg Tyr Ser Asp Ile Glu
225                 230                 235                 240

Glu Leu Lys Ser Ala Lys Asn Leu Leu Ser Val Val Glu Ser Trp Leu
                245                 250                 255

Arg Ser Glu Thr Lys Leu Pro Lys Lys Glu Leu Pro Arg Pro Glu Thr
                260                 265                 270

Gln Ala Arg Arg Ser Ser Pro Leu Asp Ala Ser Pro Phe Arg Ser Ser
                275                 280                 285

Arg His Met Ala Tyr Tyr Arg
    290                 295

<210> SEQ ID NO 16
<211> LENGTH: 294
<212> TYPE: PRT
<213> ORGANISM: Setaria italica
<220> FEATURE:
<221> NAME/KEY: MISC_FEATURE
<222> LOCATION: (1)..(294)
<223> OTHER INFORMATION: ABC Transporter

<400> SEQUENCE: 16

Met Thr Gly Glu Gly Asn Gly Asp Glu Gly Trp Arg Arg Ser Gly Ile
1               5                   10                  15

Glu Val Ser Ala Leu Gln Phe Gly Tyr Asp Gly Gln Ser Pro Leu Phe
            20                  25                  30

Ala Arg Phe Asn Leu Arg Ile Ala Pro Gly Ser Arg Cys Leu Leu Val
        35                  40                  45

Gly Ala Asn Gly Ser Gly Lys Thr Thr Leu Leu Lys Ile Leu Ala Gly
    50                  55                  60

Lys His Met Val Gly Gly Arg Asp Val Val Arg Val Leu Asn Gly Ser
65                  70                  75                  80

Ala Phe His Asp Thr Gln Leu Val Cys Asn Gly Glu Leu Ser Tyr Leu
                85                  90                  95

Gly Gly Ser Trp Ser Gln Thr Ile Gly Ser Ala Gly Asp Val Pro Leu
            100                 105                 110

Gln Gly Asp Phe Ser Ala Glu His Met Ile Phe Gly Val Asp Gly Val
        115                 120                 125

Asp Pro Val Arg Arg Glu Lys Leu Val Asp Leu Leu Asp Ile Asp Leu
    130                 135                 140

Gln Trp Arg Met His Lys Val Ser Asp Gly Gln Arg Arg Arg Val Gln
145                 150                 155                 160

Ile Cys Met Gly Leu Leu His Pro Tyr Lys Val Leu Leu Leu Asp Glu
                165                 170                 175

Ile Thr Val Asp Leu Asp Val Val Thr Arg Met Asp Leu Leu Asp Phe
            180                 185                 190

Phe Lys Glu Glu Cys Glu Gln Arg Glu Ala Thr Ile Val Tyr Ala Thr
        195                 200                 205

His Ile Phe Asp Gly Leu Glu Thr Trp Ala Thr Asp Ile Ala Tyr Ile
    210                 215                 220

Gln Glu Gly Glu Leu Arg Lys Ser Ala Lys Tyr Ser Asp Ile Glu Glu
225                 230                 235                 240
```

Leu Lys Ser Ala Glu Asn Leu Leu Ser Val Val Glu Ser Trp Leu Arg
                245                 250                 255

Ser Glu Thr Lys Leu Pro Lys Lys Asp Pro Pro Arg Thr Glu Thr Gln
            260                 265                 270

Pro Arg Arg Ser Ser Pro Phe Asp Ser Ser Pro Phe Arg Ser Ser Arg
        275                 280                 285

His Met Ala Tyr Tyr Arg
    290

<210> SEQ ID NO 17
<211> LENGTH: 292
<212> TYPE: PRT
<213> ORGANISM: Oryza sativa
<220> FEATURE:
<221> NAME/KEY: MISC_FEATURE
<222> LOCATION: (1)..(292)
<223> OTHER INFORMATION: ABC Transporter

<400> SEQUENCE: 17

Met Ala Gly Gly Glu Asp Glu Gly Trp Arg Arg Ser Gly Ile Glu Val
1               5                   10                  15

Ser Ala Leu Gln Phe Asp Tyr Asp Gly Gln Pro Pro Leu Phe Ala Arg
            20                  25                  30

Phe Asn Leu Arg Ile Ala Pro Gly Ser Arg Cys Leu Leu Ile Gly Ala
        35                  40                  45

Asn Gly Ser Gly Lys Thr Thr Leu Leu Lys Ile Leu Ala Gly Lys His
    50                  55                  60

Met Val Gly Gly Arg Asp Val Val Arg Val Leu Asn Gly Ser Ala Phe
65                  70                  75                  80

His Asp Thr Gln Leu Val Cys Asn Gly Asp Leu Ser Tyr Leu Gly Gly
                85                  90                  95

Ser Trp Ser Arg Ala Ile Gly Ser Ala Gly Asp Val Pro Leu Gln Gly
            100                 105                 110

Asp Phe Ser Ala Glu His Met Ile Phe Gly Val Asp Gly Val Asp Pro
        115                 120                 125

Val Arg Arg Glu Lys Leu Val Asp Leu Leu Asp Ile Asp Leu Gln Trp
    130                 135                 140

Arg Met His Lys Val Ser Asp Gly Gln Arg Arg Arg Val Gln Ile Cys
145                 150                 155                 160

Met Gly Leu Leu His Pro Tyr Lys Val Leu Leu Leu Asp Glu Ile Thr
                165                 170                 175

Val Asp Leu Asp Val Val Thr Arg Met Asp Leu Leu Asp Phe Phe Lys
            180                 185                 190

Glu Glu Cys Glu Gln Arg Glu Ala Thr Ile Val Tyr Ala Thr His Ile
        195                 200                 205

Phe Asp Gly Leu Glu Ser Trp Ala Thr Asp Ile Ala Tyr Ile Gln Glu
    210                 215                 220

Gly Glu Leu Arg Lys Ser Ala Lys Ser Tyr Ser Asp Val Glu Glu Leu Lys
225                 230                 235                 240

Ser Ala Lys Asn Leu Leu Ser Val Val Glu Ser Trp Leu Arg Ser Glu
                245                 250                 255

Thr Lys Leu Pro Lys Lys Glu His Pro Arg Pro Glu Thr Gln Pro Arg
            260                 265                 270

Arg Ser Ser Pro Phe Asp Ala Ser Pro Phe Arg Ser Ser Arg His Met
        275                 280                 285

Ala Tyr Tyr Arg

<210> SEQ ID NO 18
<211> LENGTH: 298
<212> TYPE: PRT
<213> ORGANISM: Oryza brachyantha
<220> FEATURE:
<221> NAME/KEY: MISC_FEATURE
<222> LOCATION: (1)..(298)
<223> OTHER INFORMATION: ABC Transporter

<400> SEQUENCE: 18

Met Ala Gly Gly Gly Gly Gly Gly Gly Asp Glu Gly Trp Lys
1               5                   10                  15

Arg Ser Gly Ile Glu Val Ser Ala Leu Gln Phe Gly Tyr Asp Gly Gln
            20                  25                  30

Pro Pro Leu Phe Ala Arg Phe Asp Leu Arg Val Ala Pro Gly Ser Arg
        35                  40                  45

Cys Leu Leu Met Gly Ala Asn Gly Ser Gly Lys Thr Thr Leu Leu Lys
    50                  55                  60

Ile Leu Ala Gly Lys His Met Val Gly Gly Arg Asp Val Val Arg Val
65                  70                  75                  80

Leu Asn Gly Ser Ala Phe His Asp Thr Gln Leu Val Cys Asn Gly Asp
                85                  90                  95

Leu Ser Tyr Leu Gly Gly Ser Trp Ser Arg Thr Ile Gly Ser Ala Gly
            100                 105                 110

Asp Val Pro Leu Gln Gly Asp Phe Ser Ala Glu His Met Ile Phe Gly
        115                 120                 125

Val Asp Gly Val Asp Pro Val Arg Arg Glu Lys Leu Val Asp Leu Leu
130                 135                 140

Asp Ile Asp Leu Gln Trp Arg Met His Lys Val Ser Asp Gly Gln Arg
145                 150                 155                 160

Arg Arg Val Gln Ile Cys Met Gly Leu Leu His Pro Tyr Lys Val Leu
                165                 170                 175

Leu Leu Asp Glu Ile Thr Val Asp Leu Asp Val Val Thr Arg Met Asp
            180                 185                 190

Leu Leu Asp Phe Phe Lys Glu Glu Cys Glu Gln Arg Glu Ala Thr Ile
        195                 200                 205

Val Tyr Ala Thr His Ile Phe Asp Gly Leu Glu Ser Trp Ala Thr Asp
210                 215                 220

Ile Ala Tyr Ile Gln Glu Gly Glu Leu Arg Lys Ser Ala Lys Tyr Ser
225                 230                 235                 240

Asp Val Glu Glu Leu Lys Gly Ala Lys Asn Leu Leu Ser Val Val Glu
                245                 250                 255

Ser Trp Leu Arg Ser Glu Thr Lys Leu Pro Lys Lys Glu His Pro Arg
            260                 265                 270

Pro Glu Ile Gln Pro Arg Arg Ser Ser Pro Phe Asp Val Ser Pro Phe
        275                 280                 285

Arg Ser Ser Arg His Met Ala Tyr Tyr Arg
    290                 295

<210> SEQ ID NO 19
<211> LENGTH: 294
<212> TYPE: PRT
<213> ORGANISM: Brachypodium distachyon
<220> FEATURE:
<221> NAME/KEY: MISC_FEATURE
<222> LOCATION: (1)..(294)

<223> OTHER INFORMATION: ABC Transporter

<400> SEQUENCE: 19

```
Met Ala Gly Gly Glu Gly Val Glu Glu Gly Trp Arg Lys Ser Gly Ile
1               5                   10                  15

Glu Val Ser Thr Leu Gln Phe Gly Tyr Asp Gly Gln Ala Pro Leu Phe
            20                  25                  30

Ala Arg Phe Asn Leu Arg Val Ala Pro Gly Ser Arg Cys Leu Leu Val
        35                  40                  45

Gly Ala Asn Gly Ser Gly Lys Thr Thr Leu Leu Lys Ile Leu Ala Gly
    50                  55                  60

Lys His Met Val Gly Gly Arg Asp Val Val Arg Val Leu Asn Gly Ser
65                  70                  75                  80

Ala Phe His Asp Thr Gln Phe Val Cys Ser Gly Asp Leu Ser Tyr Leu
                85                  90                  95

Gly Gly Ser Trp Ser Arg Thr Ile Gly Ser Ala Gly Asp Val Pro Leu
            100                 105                 110

Gln Gly Asp Phe Ser Ala Glu His Met Ile Phe Gly Val Asp Gly Val
        115                 120                 125

Asp Pro Val Arg Arg Glu Lys Leu Ile Asp Leu Leu Asp Ile Asp Leu
    130                 135                 140

Gln Trp Arg Met His Lys Val Ser Asp Gly Gln Arg Arg Val Gln
145                 150                 155                 160

Ile Cys Met Gly Leu Leu His Pro Tyr Lys Val Leu Leu Asp Glu
                165                 170                 175

Ile Thr Val Asp Leu Asp Val Val Thr Arg Met Asp Leu Leu Asp Phe
            180                 185                 190

Phe Lys Glu Glu Cys Glu Gln Arg Glu Ala Thr Ile Val Tyr Ala Thr
        195                 200                 205

His Ile Phe Asp Gly Leu Glu Thr Trp Ala Thr Asp Ile Ala Tyr Ile
    210                 215                 220

Gln Glu Gly Glu Leu Arg Lys Ser Ala Lys Tyr Ser Asp Ile Glu Glu
225                 230                 235                 240

Leu Lys Asn Ala Lys Asn Leu Leu Ser Val Val Glu Ser Trp Leu Lys
                245                 250                 255

Ser Glu Thr Lys Leu Pro Lys Lys Glu Pro Ile Arg Ala Glu Ser Gln
            260                 265                 270

Pro Arg Arg Ser Ser Pro Phe Asp Ala Ser Pro Phe Arg Ser Ser Arg
        275                 280                 285

His Met Ala Tyr Tyr Arg
    290
```

<210> SEQ ID NO 20
<211> LENGTH: 291
<212> TYPE: PRT
<213> ORGANISM: Triticum urartu
<220> FEATURE:
<221> NAME/KEY: MISC_FEATURE
<222> LOCATION: (1)..(291)
<223> OTHER INFORMATION: ABC Transporter

<400> SEQUENCE: 20

```
Met Ala Gly Gly Glu Glu Gly Trp Arg Arg Ser Gly Ile Glu Val Ser
1               5                   10                  15

Thr Leu Gln Phe Gly Tyr Asp Gly Glu Ala Pro Leu Phe Ala Arg Phe
            20                  25                  30
```

-continued

```
Asn Leu Arg Val Ala Pro Gly Ser Arg Cys Leu Leu Val Gly Ala Asn
             35                  40                  45

Gly Ser Gly Lys Thr Thr Leu Leu Lys Ile Leu Ala Gly Lys His Met
 50                  55                  60

Val Gly Gly Lys Asp Val Val Arg Val Leu Asn Gly Ser Ala Phe His
 65                  70                  75                  80

Asp Thr Gln Phe Val Cys Ser Gly Asp Leu Ser Tyr Leu Gly Gly Ser
                 85                  90                  95

Trp Ser Arg Asn Val Ser Ser Val Gly Asp Val Pro Leu Gln Gly Asp
                100                 105                 110

Phe Ser Ala Glu His Met Ile Phe Gly Val Asp Gly Val Asp Pro Val
            115                 120                 125

Arg Arg Glu Lys Leu Ile Asp Leu Leu Asp Ile Asp Leu Gln Trp Arg
130                 135                 140

Met His Lys Val Ser Asp Gly Gln Arg Arg Val Gln Ile Cys Met
145                 150                 155                 160

Gly Leu Leu His Pro Tyr Lys Val Leu Leu Asp Glu Ile Thr Val
                165                 170                 175

Asp Leu Asp Val Val Thr Arg Met Asp Leu Leu Asp Phe Phe Lys Glu
            180                 185                 190

Glu Cys Glu Gln Arg Glu Ala Thr Ile Val Tyr Ala Thr His Ile Phe
        195                 200                 205

Asp Gly Leu Glu Thr Trp Ala Thr Asp Ile Ala Tyr Ile Gln Glu Gly
    210                 215                 220

Glu Leu Lys Lys Ser Ala Lys Tyr Ser Asp Ile Glu Glu Leu Lys Thr
225                 230                 235                 240

Ala Lys Asn Leu Leu Thr Val Val Glu Ser Trp Leu Lys Ser Glu Thr
                245                 250                 255

Lys Leu Pro Lys Lys Glu Pro Ala Arg Val Glu Ser Gln Pro Arg Arg
            260                 265                 270

Ser Ser Pro Phe Asp Ala Ser Pro Phe Arg Ala Ser Arg His Met Ala
        275                 280                 285

Tyr Tyr Arg
    290

<210> SEQ ID NO 21
<211> LENGTH: 291
<212> TYPE: PRT
<213> ORGANISM: Hordeum vulgare
<220> FEATURE:
<221> NAME/KEY: MISC_FEATURE
<222> LOCATION: (1)..(291)
<223> OTHER INFORMATION: ABC Transporter

<400> SEQUENCE: 21

Met Ala Gly Gly Glu Glu Gly Trp Arg Arg Ser Gly Ile Glu Val Ser
 1               5                  10                  15

Thr Leu Gln Phe Gly Tyr Asp Gly Glu Ala Pro Leu Phe Ala Arg Phe
             20                  25                  30

Asn Leu Arg Val Ala Pro Gly Ser Arg Cys Leu Leu Val Gly Ala Asn
             35                  40                  45

Gly Ser Gly Lys Thr Thr Leu Leu Lys Ile Leu Ala Gly Lys His Met
 50                  55                  60

Val Gly Gly Lys Asp Val Val Arg Val Leu Asn Gly Ser Ala Phe His
 65                  70                  75                  80

Asp Thr Gln Phe Val Cys Ser Gly Asp Leu Ser Tyr Leu Gly Gly Ser
```

```
                    85                  90                  95
Trp Ser Arg Thr Val Ser Ser Val Gly Asp Val Pro Leu Gln Gly Asp
                100                 105                 110
Phe Ser Ala Glu His Met Ile Phe Gly Val Asp Gly Val Asp Pro Val
                115                 120                 125
Arg Arg Asp Lys Leu Ile Asp Leu Leu Asp Ile Asp Leu Gln Trp Arg
    130                 135                 140
Met His Lys Val Ser Asp Gly Gln Arg Arg Val Gln Ile Cys Met
145                 150                 155                 160
Gly Leu Leu His Pro Tyr Lys Val Leu Leu Asp Glu Ile Thr Val
                165                 170                 175
Asp Leu Asp Val Val Thr Arg Met Asp Leu Leu Asp Phe Phe Lys Glu
                180                 185                 190
Glu Cys Glu Gln Arg Glu Ala Thr Ile Val Tyr Ala Thr His Ile Phe
                195                 200                 205
Asp Gly Leu Glu Thr Trp Ala Thr Asp Ile Ala Tyr Ile Gln Glu Gly
                210                 215                 220
Glu Leu Lys Arg Ser Ala Lys Tyr Ser Asp Ile Glu Glu Leu Lys Thr
225                 230                 235                 240
Ala Lys Asn Leu Leu Ser Val Val Glu Ser Trp Leu Lys Ser Glu Thr
                    245                 250                 255
Lys Leu Pro Lys Lys Glu Pro Ala Leu Val Glu Thr Gln Pro Arg Arg
                260                 265                 270
Pro Ser Pro Phe Asp Ala Ser Pro Phe Arg Ala Ser Arg His Met Ala
                275                 280                 285
Tyr Tyr Arg
    290

<210> SEQ ID NO 22
<211> LENGTH: 291
<212> TYPE: PRT
<213> ORGANISM: Aegilops tauschii
<220> FEATURE:
<221> NAME/KEY: MISC_FEATURE
<222> LOCATION: (1)..(291)
<223> OTHER INFORMATION: ABC Transporter

<400> SEQUENCE: 22

Met Ala Gly Gly Glu Glu Gly Trp Arg Arg Ser Gly Ile Glu Val Ser
1               5                   10                  15
Thr Leu Gln Phe Gly Tyr Asp Gly Glu Ala Pro Leu Phe Ala Arg Phe
                20                  25                  30
Asn Leu Arg Val Ala Pro Gly Ser Arg Cys Leu Leu Val Gly Ala Asn
            35                  40                  45
Gly Ser Gly Lys Thr Thr Leu Leu Lys Ile Leu Ala Gly Lys His Met
        50                  55                  60
Val Gly Gly Lys Asp Val Val Arg Val Leu Asn Gly Ser Ala Phe His
65                  70                  75                  80
Asp Thr Gln Phe Val Cys Ser Gly Asp Leu Ser Tyr Leu Gly Ser
                85                  90                  95
Trp Ser Arg Asn Val Ser Ser Val Gly Asp Val Pro Leu Gln Gly Asp
                100                 105                 110
Phe Ser Ala Glu His Met Ile Phe Gly Val Asp Gly Val Asp Pro Val
                115                 120                 125
Arg Arg Glu Lys Leu Ile Asp Leu Leu Asp Ile Asp Leu Gln Trp Arg
    130                 135                 140
```

```
Met His Lys Val Ser Asp Gly Gln Arg Arg Val Gln Ile Cys Met
145                 150                 155                 160

Gly Leu Leu His Pro Tyr Lys Val Leu Leu Asp Glu Ile Thr Val
                165                 170                 175

Asp Leu Asp Val Val Thr Arg Met Asp Leu Leu Asp Phe Phe Lys Glu
            180                 185                 190

Glu Cys Glu Gln Arg Glu Ala Thr Ile Val Tyr Ala Thr His Ile Phe
            195                 200                 205

Asp Gly Leu Glu Thr Trp Ala Thr Asp Ile Ala Tyr Ile Gln Glu Gly
            210                 215                 220

Glu Leu Lys Lys Ser Ala Lys Tyr Ser Asp Ile Glu Glu Leu Lys Thr
225                 230                 235                 240

Ala Lys Asn Leu Leu Ser Val Val Glu Ser Trp Leu Lys Ser Glu Ala
                245                 250                 255

Lys Leu Pro Lys Lys Glu Pro Ala Arg Val Glu Ser Gln Pro Arg Arg
            260                 265                 270

Pro Ser Pro Phe Asp Ala Ser Pro Phe Arg Ala Ser Arg His Met Ala
            275                 280                 285

Tyr Tyr Arg
    290

<210> SEQ ID NO 23
<211> LENGTH: 286
<212> TYPE: PRT
<213> ORGANISM: Elaeis guineensis
<220> FEATURE:
<221> NAME/KEY: MISC_FEATURE
<222> LOCATION: (1)..(286)
<223> OTHER INFORMATION: ABC Transporter

<400> SEQUENCE: 23

Met Ala Glu Ser Thr Gly Gly Ile Glu Val Ser Gly Leu Gln Phe Ala
1               5                   10                  15

Tyr Glu Gly Gln Pro Leu Leu Phe Thr Lys Phe Asn Leu Glu Ile Ser
                20                  25                  30

Pro Gly Ser Arg Cys Leu Leu Ile Gly Ala Asn Gly Ser Gly Lys Thr
            35                  40                  45

Thr Leu Leu Lys Ile Leu Ala Gly Lys His Met Val Gly Gly Arg Asp
        50                  55                  60

Val Val Arg Val Leu Asn Cys Ser Ala Phe His Asp Thr Gln Leu Val
65                  70                  75                  80

Cys Ser Gly Asp Leu Ala Tyr Leu Gly Gly Ser Trp Ser Lys Thr Ile
                85                  90                  95

Gly Ser Ala Gly Asp Val Pro Leu Gln Gly Asp Phe Ser Ala Glu His
            100                 105                 110

Met Ile Phe Gly Val Glu Gly Ile Asp Pro Val Arg Arg Glu Lys Leu
        115                 120                 125

Ile Asp Leu Leu Asp Ile Asp Leu Gln Trp Arg Met His Lys Val Ser
    130                 135                 140

Asp Gly Gln Arg Arg Val Gln Ile Cys Met Gly Leu Leu His Pro
145                 150                 155                 160

Tyr Lys Val Leu Leu Leu Asp Glu Val Thr Val Asp Leu Asp Val Val
                165                 170                 175

Thr Arg Leu Asp Leu Leu Asp Phe Phe Arg Glu Glu Cys Glu Glu Arg
            180                 185                 190
```

```
Gly Ala Thr Ile Val Tyr Ala Thr His Ile Phe Asp Gly Leu Glu Thr
            195                 200                 205

Trp Ala Thr Asp Val Ala Tyr Val Gln Asp Gly Glu Leu Arg Arg Ser
    210                 215                 220

Gly Lys Leu Ser Asp Ile His Glu Leu Lys Gly Ser Asn Asn Leu Leu
225                 230                 235                 240

Ser Val Val Glu Ser Trp Leu Arg Ser Glu Ser Lys Asn Pro Arg Lys
                245                 250                 255

Gln Ser Ile Ile Ser Ser Val Gln Leu Ser Arg Gly Ser Pro Phe Asp
            260                 265                 270

Ser Ser Pro Phe Arg Ser Ser Arg His Met Ala Tyr Tyr Arg
        275                 280                 285

<210> SEQ ID NO 24
<211> LENGTH: 283
<212> TYPE: PRT
<213> ORGANISM: Asparagus officinalis
<220> FEATURE:
<221> NAME/KEY: MISC_FEATURE
<222> LOCATION: (1)..(283)
<223> OTHER INFORMATION: ABC Transporter

<400> SEQUENCE: 24

Met Gly Gly Gly Ile Glu Val Ser Gly Leu Gln Phe Ala Tyr Asp Gly
1               5                   10                  15

Gln Pro Pro Ile Phe Ala Gln Phe Asn Leu Asn Ile Ala Pro Gly Ser
            20                  25                  30

Arg Cys Leu Leu Ile Gly Ala Asn Gly Ser Gly Lys Thr Thr Leu Leu
        35                  40                  45

Lys Ile Leu Ala Gly Lys His Met Val Gly Arg Asp Val Val Gln
50                  55                  60

Val Leu Ser Cys Ser Ala Phe His Asp Thr Gln Leu Val Cys Ser Gly
65                  70                  75                  80

Asp Leu Ala Tyr Leu Gly Glu Ser Trp Ser Lys Thr Val Ser Ala Ala
                85                  90                  95

Gly Asp Val Pro Leu Gln Gly Asp Phe Ser Ala Glu His Met Ile Phe
            100                 105                 110

Gly Val Glu Gly Ile Asp Pro Leu Arg Arg Glu Lys Leu Ile Asp Leu
        115                 120                 125

Leu Asp Ile Asp Leu Gln Trp Arg Met His Lys Val Ser Asp Gly Gln
130                 135                 140

Arg Arg Arg Val Gln Ile Cys Met Gly Leu Leu His Pro Tyr Lys Val
145                 150                 155                 160

Leu Leu Leu Asp Glu Val Thr Val Asp Leu Asp Val Val Thr Arg Met
                165                 170                 175

Asp Leu Leu Glu Phe Phe Lys Glu Glu Cys Glu Gln Arg Gly Ala Thr
            180                 185                 190

Ile Val Tyr Cys Thr His Ile Phe Asp Gly Leu Glu Thr Trp Ala Thr
        195                 200                 205

His Leu Ala Tyr Ile Gln Glu Gly Glu Leu Arg Arg Cys Thr Lys Met
    210                 215                 220

Glu Asp Ile His Glu Leu Glu Lys Ala Asp Asn Leu Leu Ser Val Val
225                 230                 235                 240

Glu Ser Trp Leu Arg Ser Glu Thr Lys Leu Pro Lys Lys Glu Pro Ile
                245                 250                 255

Lys Ser Ser Ile Leu Ser Arg Gly Ala Ser Pro Phe Asp Ser Ser Pro
```

```
                        260                 265                 270
Phe Lys Ser Ser Arg His Met Ala Tyr Tyr Arg
        275                 280

<210> SEQ ID NO 25
<211> LENGTH: 286
<212> TYPE: PRT
<213> ORGANISM: Phoenix dactylifera
<220> FEATURE:
<221> NAME/KEY: MISC_FEATURE
<222> LOCATION: (1)..(286)
<223> OTHER INFORMATION: ABC Transporter

<400> SEQUENCE: 25

Met Val Glu Ser Thr Gly Gly Ile Glu Val Ser Gly Leu Gln Phe Ala
1               5                   10                  15

Tyr Glu Gly Gln Pro Pro Leu Phe Thr Lys Phe Asn Leu Glu Ile Ser
            20                  25                  30

Pro Gly Asp Arg Cys Leu Leu Ile Gly Ala Asn Gly Ser Gly Lys Thr
        35                  40                  45

Thr Leu Leu Lys Ile Leu Ala Gly Lys His Met Val Gly Gly Arg Asp
    50                  55                  60

Val Val Arg Val Leu Asn Arg Ser Ala Phe His Asp Thr Gln Leu Val
65                  70                  75                  80

Cys Ser Gly Asp Leu Ala Tyr Leu Gly Gly Ser Trp Ser Lys Thr Ile
                85                  90                  95

Gly Ser Ala Gly Asp Val Pro Leu Gln Gly Asp Phe Ser Ala Glu His
            100                 105                 110

Met Ile Phe Gly Val Glu Gly Ile Asp Pro Ala Arg Arg Glu Lys Leu
        115                 120                 125

Val Ser Leu Leu Asp Ile Asp Leu Gln Trp Arg Met His Arg Val Ser
    130                 135                 140

Asp Gly Gln Arg Arg Val Gln Ile Cys Met Gly Leu Leu His Pro
145                 150                 155                 160

Tyr Lys Val Leu Leu Leu Asp Glu Val Thr Val Asp Leu Asp Val Val
                165                 170                 175

Thr Arg Met Asp Leu Leu Asp Phe Phe Lys Glu Glu Cys Glu Gln Arg
            180                 185                 190

Gly Ala Thr Ile Val Tyr Ala Thr His Ile Phe Asp Gly Leu Glu Thr
        195                 200                 205

Trp Ala Thr Asp Val Ala Tyr Ile Gln Asp Gly Glu Leu Arg Arg Phe
    210                 215                 220

Gly Lys Leu Ser Gly Ile His Glu Leu Lys Gly Ser Asn Asn Leu Leu
225                 230                 235                 240

Ser Val Val Glu Ser Trp Leu Leu Ser Glu Ser Lys Asn Pro Arg Lys
                245                 250                 255

Gln Pro Val Asn Ser Ser Val Gln Ser Ser Arg Gly Ser Pro Phe Asp
            260                 265                 270

Ser Ser Pro Phe Arg Ser Ser Arg His Met Ala Tyr Tyr Arg
        275                 280                 285

<210> SEQ ID NO 26
<211> LENGTH: 291
<212> TYPE: PRT
<213> ORGANISM: Ananas comosus
<220> FEATURE:
<221> NAME/KEY: MISC_FEATURE
<222> LOCATION: (1)..(291)
```

-continued

<223> OTHER INFORMATION: ABC Transporter

<400> SEQUENCE: 26

Met Val Glu Glu Gly Trp Arg Arg Ser Gly Ile Glu Val Arg Gly
1               5                   10                  15

Leu His Phe Ala Tyr Asp Gly Gln Pro Pro Leu Phe Val Ser Phe Asp
            20                  25                  30

Leu Glu Val Ala Pro Gly Ser Arg Cys Leu Leu Ile Gly Ala Asn Gly
        35                  40                  45

Ser Gly Lys Thr Thr Leu Leu Lys Ile Leu Ala Gly Lys His Met Val
    50                  55                  60

Gly Gly Arg Asp Val Val Arg Val Leu Asn Ser Ala Phe His Asp
65                  70                  75                  80

Thr Glu Leu Val Cys Asn Gly Asp Leu Ala Tyr Leu Gly Gly Ser Trp
                85                  90                  95

Ser Lys Thr Ile Gly Ser Ala Gly Asp Val Pro Leu Gln Gly Asp Phe
            100                 105                 110

Ser Ala Glu His Met Ile Phe Gly Val Glu Gly Val Asp Pro Val Arg
        115                 120                 125

Arg Glu Lys Leu Ile Asp Leu Leu Asp Ile Asp Leu Asp Trp Arg Met
    130                 135                 140

His Lys Val Ser Asp Gly Gln Arg Arg Val Gln Ile Cys Met Gly
145                 150                 155                 160

Leu Leu His Pro Tyr Lys Val Leu Leu Leu Asp Glu Val Thr Val Asp
                165                 170                 175

Leu Asp Val Val Thr Arg Met Asp Leu Leu Asp Phe Phe Lys Glu Glu
            180                 185                 190

Cys Glu Gln Arg Glu Ala Thr Ile Val Tyr Ala Thr His Ile Phe Asp
        195                 200                 205

Gly Leu Glu Ser Trp Ala Thr His Val Ala Tyr Ile Gln Asp Gly Glu
    210                 215                 220

Leu Arg Arg Ser Ala Lys Met Ser Asp Val His Glu Leu Lys Ser Ala
225                 230                 235                 240

Glu Asn Leu Leu Ser Val Val Glu Ser Trp Leu His Ser Glu Val Lys
                245                 250                 255

Arg Pro Ile Glu Lys Glu Ser Val Asn Ser Thr Leu Gln Ser Leu Lys
            260                 265                 270

Ser Ser Pro Phe Asp Gln Ser Pro Phe Arg Ser Ser Arg His Met Ala
        275                 280                 285

Tyr Tyr Arg
    290

<210> SEQ ID NO 27
<211> LENGTH: 287
<212> TYPE: PRT
<213> ORGANISM: Musa acuminata
<220> FEATURE:
<221> NAME/KEY: MISC_FEATURE
<222> LOCATION: (1)..(287)
<223> OTHER INFORMATION: ABC Transporter

<400> SEQUENCE: 27

Met Glu Gly Gly Gly Ile Glu Val Ser Ser Leu Asn Phe Ala Tyr Glu
1               5                   10                  15

Gly Leu Pro Pro Leu Phe Thr Arg Phe Asn Leu Asp Val Ser Pro Gly
            20                  25                  30

Ser Arg Cys Leu Leu Val Gly Ala Asn Gly Ser Gly Lys Thr Thr Leu
        35                  40                  45

Leu Lys Ile Leu Ala Gly Lys His Met Val Gly Gly Arg Asp Val Val
 50                  55                  60

Arg Val Leu Asn Ala Ser Ala Phe His Asp Thr Arg Leu Val Cys Ser
 65                  70                  75                  80

Gly Asp Leu Ala Tyr Leu Gly Gly Ser Trp Ser Lys Thr Val Gly Ser
                 85                  90                  95

Ala Gly Asp Ile Pro Leu Gln Gly Asp Phe Ser Ala Glu His Met Ile
             100                 105                 110

Phe Gly Val Glu Gly Ile Asp Pro Ala Arg Arg Glu Lys Leu Ile Asp
         115                 120                 125

Leu Leu Asp Ile Asn Leu Gln Trp Arg Met His Lys Val Ser Asp Gly
130                 135                 140

Gln Arg Arg Arg Val Gln Ile Cys Met Gly Leu Leu Tyr Pro Tyr Lys
145                 150                 155                 160

Val Leu Leu Leu Asp Glu Val Thr Val Asp Leu Asp Val Thr Arg
                 165                 170                 175

Met Asp Leu Leu Glu Phe Phe Thr Glu Glu Cys Glu Gln Arg Gly Val
             180                 185                 190

Ile Ile Val Tyr Ala Thr His Ile Phe Asp Gly Leu Glu Thr Trp Ala
         195                 200                 205

Thr His Val Ala Tyr Ile Gln Asp Gly Asp Leu Lys Arg Ser Gly Lys
     210                 215                 220

Leu Ser Asp Ile Ile Glu Leu Lys Ser Ala Asn Asn Leu Leu Ser Val
225                 230                 235                 240

Val Glu Ser Trp Leu Arg Ser Glu Ser Lys Leu Pro Lys Lys Glu Leu
                 245                 250                 255

Ile Lys Pro Ile Ser Ala Val Ala Arg Ser Ser Thr Leu Ser Pro Phe
             260                 265                 270

Asp Ser Ser Pro Phe Arg Ser Ser Arg His Met Ala Tyr Tyr Arg
         275                 280                 285

<210> SEQ ID NO 28
<211> LENGTH: 286
<212> TYPE: PRT
<213> ORGANISM: Phalaenopsis equestris
<220> FEATURE:
<221> NAME/KEY: MISC_FEATURE
<222> LOCATION: (1)..(286)
<223> OTHER INFORMATION: ABC Transporter

<400> SEQUENCE: 28

Met Ala Glu Thr Gly Gly Gly Ile Glu Val Thr Gly Met Gln Phe Ala
1               5                   10                  15

Tyr Asp Gly Arg Gln Arg Ile Phe Ala Arg Phe Ser Leu Glu Val Ser
             20                  25                  30

Pro Gly Ser Arg Cys Leu Leu Ile Gly Ala Asn Gly Ser Gly Lys Thr
         35                  40                  45

Thr Leu Leu Arg Ile Leu Ala Gly Lys His Met Val Gly Gly Arg Asn
 50                  55                  60

Val Val Arg Val Leu Asn Cys Ser Ala Phe His Asp Thr His Leu Val
 65                  70                  75                  80

Cys Ser Gly Asp Leu Ala Tyr Leu Gly Glu Ser Trp Ser Lys Thr Val
                 85                  90                  95

Gly Ser Val Gly Asp Val Pro Leu Gln Gly Asp Phe Ser Ala Glu His

```
            100                 105                 110
Met Ile Phe Gly Val Glu Gly Ala Asp Pro Leu Arg Arg Glu Lys Leu
            115                 120                 125

Ile Asp Leu Leu Asp Ile Asn Leu Gln Trp Arg Met His Lys Val Ser
            130                 135                 140

Asp Gly Gln Arg Arg Arg Val Gln Ile Cys Met Gly Leu Leu Arg Pro
145                 150                 155                 160

Tyr Lys Val Leu Leu Leu Asp Glu Val Thr Val Asp Leu Asp Val Val
                    165                 170                 175

Thr Arg Met Asp Leu Leu Asp Phe Phe Lys Glu Glu Cys Glu Gln Arg
                180                 185                 190

Gly Ala Thr Ile Val Tyr Ala Thr His Ile Phe Asp Gly Leu Glu Thr
            195                 200                 205

Trp Ala Thr Asp Leu Ala Tyr Ile Gln Glu Gly Glu Leu Lys Arg Leu
            210                 215                 220

Ala Lys Leu Ala Glu Ile Lys Glu Leu Lys Glu Ala Lys Asn Leu Leu
225                 230                 235                 240

Ser Val Val Glu Ser Trp Leu Arg Ser Glu Thr Lys Leu Pro Lys Lys
                    245                 250                 255

Glu Pro Phe Leu Ser Pro Ala Gln Thr Thr Val Ser Ser Pro Phe Asp
                260                 265                 270

Ala Ser Pro Phe Arg Ser Ser Arg His Met Ala Tyr Tyr Arg
            275                 280                 285

<210> SEQ ID NO 29
<211> LENGTH: 287
<212> TYPE: PRT
<213> ORGANISM: Dendrobium catenatum
<220> FEATURE:
<221> NAME/KEY: MISC_FEATURE
<222> LOCATION: (1)..(287)
<223> OTHER INFORMATION: ABC Transporter

<400> SEQUENCE: 29

Met Ala Glu Ser Gly Gly Gly Ile Glu Val Thr Ser Met Gln Phe Ala
1               5                   10                  15

Tyr Asp Gly Arg Gln Pro Ile Phe Ala Arg Phe Ser Leu Lys Val Ser
                20                  25                  30

Pro Gly Ser Arg Cys Leu Leu Ile Gly Ala Asn Gly Ser Gly Lys Thr
            35                  40                  45

Thr Leu Leu Arg Ile Leu Ala Gly Lys His Met Val Gly Gly Arg Asp
        50                  55                  60

Val Val Arg Val Leu Asn Cys Ser Ala Phe His Asp Thr His Leu Val
65                  70                  75                  80

Cys Ser Gly Asp Leu Ala Tyr Leu Gly Glu Ser Trp Ser Lys Thr Val
                85                  90                  95

Gly Ser Thr Gly Asp Val Pro Leu Gln Gly Asp Phe Ser Ala Glu His
            100                 105                 110

Met Ile Phe Gly Val Glu Gly Ala Asp Pro Leu Arg Arg Glu Lys Leu
            115                 120                 125

Ile Asp Leu Leu Asp Ile Asn Leu Gln Trp Arg Met His Lys Val Ser
            130                 135                 140

Asp Gly Gln Arg Arg Arg Val Gln Ile Cys Ile Gly Leu Leu Gln Pro
145                 150                 155                 160

Tyr Lys Val Leu Leu Leu Asp Glu Val Thr Val Asp Leu Asp Val Val
                    165                 170                 175
```

```
Thr Arg Met Asp Leu Leu Asp Phe Phe Lys Glu Glu Cys Glu Gln Arg
            180                 185                 190

Gly Ala Thr Ile Val Tyr Ala Thr His Ile Phe Asp Gly Leu Glu Ala
        195                 200                 205

Trp Ala Thr Asp Leu Ala Tyr Ile Gln Glu Gly Glu Leu Arg Arg Leu
    210                 215                 220

Ala Lys Val Ala Asp Ile Gln Glu Leu Lys Asp Ala Lys Asn Leu Leu
225                 230                 235                 240

Ser Val Val Glu Ser Trp Leu Arg Ser Glu Thr Lys Leu Pro Lys Lys
                245                 250                 255

Glu Leu Ile Gly Phe His Ala Lys Ser Thr Gly Ser Ser Pro Phe
            260                 265                 270

Asp Ala Ser Pro Phe Arg Ser Ser Arg His Met Ala Tyr Tyr Arg
            275                 280                 285
```

<210> SEQ ID NO 30
<211> LENGTH: 289
<212> TYPE: PRT
<213> ORGANISM: Daucus carota
<220> FEATURE:
<221> NAME/KEY: MISC_FEATURE
<222> LOCATION: (1)..(289)
<223> OTHER INFORMATION: ABC Transporter

<400> SEQUENCE: 30

```
Met Ala Arg Glu Gly Asp Glu Ser Asn Gly Ile Arg Val Lys Gly Met
1               5                   10                  15

Gln Phe Gly Tyr Asp Ile Gln Ile Pro Leu Phe Val Asp Phe Thr Leu
                20                  25                  30

Asp Ile Ser Pro Gly Ser Arg Cys Leu Leu Val Gly Ala Asn Gly Ser
            35                  40                  45

Gly Lys Thr Thr Leu Leu Lys Ile Leu Ala Gly Lys His Met Val Gly
        50                  55                  60

Gly Arg Asp Val Val Gln Val Leu Asn Cys Ser Ala Phe His Asp Thr
65                  70                  75                  80

His Leu Val Cys Ser Gly Asp Leu Ser Tyr Leu Gly Ser Trp Thr
                85                  90                  95

Lys Thr Val Gly Ser Ala Gly Glu Ile Pro Leu Gln Gly Asp Phe Ser
            100                 105                 110

Ala Glu His Met Ile Phe Gly Val Glu Gly Ile Asp Pro Val Arg Arg
        115                 120                 125

Glu Lys Leu Ile Asp Leu Leu Asp Ile Asp Leu Arg Trp Arg Met His
    130                 135                 140

Lys Val Ser Asp Gly Gln Arg Arg Val Gln Ile Cys Met Gly Leu
145                 150                 155                 160

Leu His Pro Phe Gln Val Leu Leu Asp Glu Val Thr Val Asp Leu
                165                 170                 175

Asp Val Val Ala Arg Met Asp Leu Leu Asp Phe Phe Lys Glu Glu Cys
            180                 185                 190

Glu Gln Arg Gly Ala Thr Ile Val Tyr Ala Thr His Ile Phe Asp Gly
        195                 200                 205

Leu Glu Thr Trp Ala Thr Asp Leu Ala Tyr Ile Gln Asp Gly Glu Leu
    210                 215                 220

Arg Arg Thr Asp Lys Leu Ser Glu Leu Ala Glu Leu Lys His Ala Ala
225                 230                 235                 240
```

```
Asn Leu Leu Ser Val Val Glu Ser Trp Leu Arg Ser Glu Thr Lys Ile
                245                 250                 255

Glu Lys Lys Lys Pro Val Ser Asn Ser Ser Gln Val Arg Lys Ser Ser
            260                 265                 270

Pro Phe Asp Ser Ser Pro Phe Arg Ser Thr Arg His Met Ala Tyr Tyr
            275                 280                 285

Arg

<210> SEQ ID NO 31
<211> LENGTH: 287
<212> TYPE: PRT
<213> ORGANISM: Camellia sinensis
<220> FEATURE:
<221> NAME/KEY: MISC_FEATURE
<222> LOCATION: (1)..(287)
<223> OTHER INFORMATION: ABC Transporter

<400> SEQUENCE: 31

Met Glu Glu Lys Asn Trp Ser Ser Ile Glu Val Ser Gly Met Gln Phe
1               5                   10                  15

Gly Tyr Asp Gly Gln Ser Pro Val Phe Ile Asp Phe Thr Leu Lys Ile
            20                  25                  30

Leu Pro Gly Ser Arg Cys Leu Leu Val Gly Ala Asn Gly Ser Gly Lys
        35                  40                  45

Thr Thr Leu Leu Lys Ile Leu Ala Gly Lys His Met Val Gly Gly Arg
    50                  55                  60

Asp Val Val Arg Val Leu Asn Cys Ser Ala Phe His Asp Thr His Leu
65                  70                  75                  80

Val Cys Ser Gly Asp Leu Ser Tyr Leu Gly Ser Trp Ser Lys Thr
                85                  90                  95

Val Gly Ser Ala Gly Glu Ile Pro Leu Gln Gly Asp Phe Ser Ala Glu
            100                 105                 110

His Met Ile Phe Gly Val Glu Gly Val Asp Pro Val Arg Arg Glu Lys
        115                 120                 125

Leu Ile Glu Leu Leu Asp Ile Asp Leu Gln Trp Arg Met His Lys Val
    130                 135                 140

Ser Asp Gly Gln Arg Arg Val Gln Ile Cys Met Gly Leu Leu His
145                 150                 155                 160

Pro Phe Gln Val Leu Leu Leu Asp Glu Val Thr Val Asp Leu Asp Val
                165                 170                 175

Val Ala Arg Leu Asp Leu Leu Asp Phe Phe Lys Glu Glu Cys Glu Gln
            180                 185                 190

Arg Gly Ala Thr Ile Val Tyr Ala Thr His Ile Phe Asp Gly Leu Glu
        195                 200                 205

Thr Trp Ala Thr Asp Leu Ala Tyr Ile His Ala Gly Glu Leu Lys Arg
    210                 215                 220

Thr Asp Lys Leu Ser Glu Leu Gly Glu Leu Lys Asn Ser Ala Asn Leu
225                 230                 235                 240

Leu Ser Val Val Glu Ser Trp Leu Arg Ser Glu Thr Asn Thr Glu Lys
                245                 250                 255

Lys Lys Pro Thr Asn Pro Pro Val Glu Asn Gln Lys Thr Ser Pro Phe
            260                 265                 270

Asp Ser Ser Pro Phe Arg Ser Ser Arg His Met Ala Tyr Tyr Arg
            275                 280                 285

<210> SEQ ID NO 32
```

```
<211> LENGTH: 291
<212> TYPE: PRT
<213> ORGANISM: Vitis vinifera
<220> FEATURE:
<221> NAME/KEY: MISC_FEATURE
<222> LOCATION: (1)..(291)
<223> OTHER INFORMATION: ABC Transporter

<400> SEQUENCE: 32

Met Ala Ile Gln Ser Ser Ser Ser Asn Ser Ile Lys Val Asn Gly
1               5                   10                  15

Leu Gln Phe Ala Tyr Glu Gly Gln Pro Pro Leu Phe Leu Asp Phe Asn
                20                  25                  30

Leu Gln Ile Ser Pro Gly Ser Arg Cys Leu Leu Val Gly Ala Asn Gly
                35                  40                  45

Ser Gly Lys Thr Thr Leu Leu Arg Ile Leu Ala Gly Lys His Met Val
        50                  55                  60

Gly Gly Arg Asp Val Val Gln Val Leu Asn Cys Ser Ala Phe His Asp
65              70                  75                  80

Thr His Leu Val Cys Ser Gly Asp Leu Ser Tyr Leu Gly Gly Ser Trp
                85                  90                  95

Ser Lys Asn Ile Gly Ser Ala Gly Glu Val Pro Leu Gln Gly Asp Phe
                100                 105                 110

Ser Ala Glu His Met Ile Phe Gly Val Glu Gly Ile Asn Pro Val Arg
                115                 120                 125

Arg Asp Lys Leu Val Asp Leu Leu Asp Ile Asp Leu Gln Trp Arg Met
130             135                 140

His Lys Val Ser Asp Gly Gln Arg Arg Val Gln Ile Cys Met Gly
145             150                 155                 160

Leu Leu His Pro Phe Gln Val Leu Leu Leu Asp Glu Val Thr Val Asp
                165                 170                 175

Leu Asp Val Val Ala Arg Met Asp Leu Leu Glu Phe Phe Lys Glu Glu
                180                 185                 190

Cys Asp Gln Arg Gly Ala Thr Ile Val Tyr Ala Thr His Ile Phe Asp
                195                 200                 205

Gly Leu Glu Thr Trp Ala Thr Asp Leu Ala Tyr Val Gln Glu Gly Asp
        210                 215                 220

Leu Arg Lys Ile Glu Lys Leu Ser Glu Leu Asp Glu Leu Lys Thr Ser
225             230                 235                 240

Ala Asn Leu Leu Ser Val Val Glu Ser Trp Leu Arg Ser Glu Thr Lys
                245                 250                 255

Cys Glu Lys Lys Lys Pro Ile Asn Pro Pro Ala Gln Ile Gln Arg Thr
                260                 265                 270

Pro Ser Pro Phe Asp Ser Ser Pro Phe Arg Ser Arg His Met Ala
                275                 280                 285

Tyr Tyr Arg
    290

<210> SEQ ID NO 33
<211> LENGTH: 299
<212> TYPE: PRT
<213> ORGANISM: Theobroma cacao
<220> FEATURE:
<221> NAME/KEY: MISC_FEATURE
<222> LOCATION: (1)..(299)
<223> OTHER INFORMATION: ABC Transporter

<400> SEQUENCE: 33
```

```
Met Ala Glu Gln Ala Cys Cys Lys Ser Arg Glu Glu Gly Asn Gly
1               5                   10                  15

Glu Ser Lys Gly Ile Arg Val Cys Gly Met Gln Phe Ala Tyr Glu Leu
            20                  25                  30

Gln Pro Pro Leu Phe Val Asp Phe Asp Val Asp Ile Ala Pro Gly Ser
        35                  40                  45

Arg Cys Leu Leu Val Gly Ala Asn Gly Ser Gly Lys Thr Thr Leu Leu
    50                  55                  60

Lys Ile Leu Ala Gly Lys His Met Val Gly Arg Asp Val Val Arg
65                  70                  75                  80

Val Leu Asn Arg Ser Ala Phe His Asp Thr Gln Leu Val Cys Ser Gly
                85                  90                  95

Asp Leu Ala Tyr Leu Gly Gly Ser Trp Ser Lys Thr Ile Gly Ser Ala
            100                 105                 110

Gly Glu Val Pro Leu Gln Gly Asp Phe Ser Ala Glu His Met Ile Phe
            115                 120                 125

Gly Val Glu Gly Ile Asp Pro Val Arg Arg Gly Lys Leu Ile Glu Leu
        130                 135                 140

Leu Asp Ile Asp Leu Gln Trp Arg Met His Lys Val Ser Asp Gly Gln
145                 150                 155                 160

Arg Arg Arg Val Gln Ile Cys Met Gly Leu Leu His Pro Phe Gln Val
                165                 170                 175

Leu Leu Leu Asp Glu Val Thr Val Asp Leu Asp Val Val Ala Arg Met
            180                 185                 190

Asp Leu Leu Asp Phe Phe Lys Glu Glu Cys Glu Gln Arg Gly Ala Thr
            195                 200                 205

Ile Val Tyr Ala Thr His Ile Phe Asp Gly Leu Glu Thr Trp Ala Thr
    210                 215                 220

His Leu Ala Tyr Ile Gln Asp Gly Glu Leu Lys Arg Ser Glu Lys Leu
225                 230                 235                 240

Thr Glu Val Asn Glu Leu Lys Ser Ser Glu Asn Leu Leu Ser Val Val
                245                 250                 255

Glu Ala Trp Leu Arg Ser Glu Thr Lys Cys Glu Lys Lys Lys Pro Ile
            260                 265                 270

Lys Thr Pro Ala Gln Val Gln Lys Ala Ser Pro Phe Gly Ile Ser Pro
        275                 280                 285

Phe Met Ser Ser Arg His Met Ala Tyr Tyr Arg
        290                 295

<210> SEQ ID NO 34
<211> LENGTH: 299
<212> TYPE: PRT
<213> ORGANISM: Corchorus capsularis
<220> FEATURE:
<221> NAME/KEY: MISC_FEATURE
<222> LOCATION: (1)..(299)
<223> OTHER INFORMATION: ABC Transporter

<400> SEQUENCE: 34

Met Ala Glu Gln Thr Phe Cys Lys Ser Arg Glu Gly Asp Glu Asn Ala
1               5                   10                  15

Glu Ser Lys Ser Ile Arg Val Cys Gly Met Gln Phe Ala Tyr Glu Leu
            20                  25                  30

Gln His Pro Leu Phe Val Asp Phe Asn Leu Glu Ile Ala Pro Gly Ser
        35                  40                  45

Arg Cys Leu Leu Val Gly Ala Asn Gly Ser Gly Lys Thr Thr Leu Leu
```

```
            50                  55                  60
Lys Ile Leu Ala Gly Lys His Met Val Gly Gly Arg Asp Val Val Arg
 65                  70                  75                  80

Val Leu Asn Arg Ser Ala Phe His Asp Thr Gln Leu Val Cys Gly Gly
                 85                  90                  95

Asp Leu Ala Tyr Leu Gly Gly Ser Trp Ser Lys Thr Ile Gly Ser Ala
            100                 105                 110

Gly Glu Val Pro Leu Gln Gly Asp Phe Ser Ala Glu His Met Ile Phe
        115                 120                 125

Gly Val Glu Gly Ile Asp Pro Val Arg Arg Glu Lys Leu Ile Glu Leu
    130                 135                 140

Leu Asp Ile Asp Leu Gln Trp Arg Met His Lys Val Ser Asp Gly Gln
145                 150                 155                 160

Arg Arg Arg Val Gln Ile Cys Met Gly Leu Leu His Pro Phe Gln Val
                165                 170                 175

Leu Leu Leu Asp Glu Val Thr Val Asp Leu Asp Val Val Ala Arg Met
            180                 185                 190

Asp Leu Leu Asp Phe Phe Lys Glu Glu Cys Glu Gln Arg Gly Ala Thr
        195                 200                 205

Val Val Tyr Ala Thr His Ile Phe Asp Gly Leu Glu Thr Trp Ala Thr
    210                 215                 220

His Leu Ala Tyr Ile Gln Asp Gly Glu Leu Lys Lys Ser Glu Lys Leu
225                 230                 235                 240

Thr Glu Ile Asn Glu Leu Lys Ser Ser Glu Asn Leu Leu Ser Val Val
                245                 250                 255

Glu Ala Trp Leu Arg Ser Glu Thr Lys Cys Glu Lys Lys Lys Ala Val
            260                 265                 270

Asn Asn Pro Ala Gln Val Gln Lys Thr Ser Pro Phe Gly Thr Ser Pro
        275                 280                 285

Phe Met Ser Ser Arg His Met Ala Tyr Tyr Arg
    290                 295

<210> SEQ ID NO 35
<211> LENGTH: 295
<212> TYPE: PRT
<213> ORGANISM: Morus notabilis
<220> FEATURE:
<221> NAME/KEY: MISC_FEATURE
<222> LOCATION: (1)..(295)
<223> OTHER INFORMATION: ABC Transporter

<400> SEQUENCE: 35

Met Ala Asp Gly Glu Glu Asp Gln Arg Asp Glu Arg Ser Ser Gly Ile
 1               5                  10                  15

Lys Val Tyr Gly Leu Gln Phe Val Tyr Asp Gly Gln Pro Pro Leu Phe
                20                  25                  30

Ala Glu Phe Asn Leu Asp Ile Ser Pro Gly Ser Arg Cys Leu Leu Val
            35                  40                  45

Gly Ala Asn Gly Ser Gly Lys Thr Thr Leu Leu Lys Ile Leu Ala Gly
        50                  55                  60

Lys His Met Val Gly Gly Arg Asp Val Val Gln Val Leu Asn Gly Ser
 65                  70                  75                  80

Ala Phe His Asp Thr His Leu Val Cys Ser Gly Asp Leu Ala Tyr Leu
                85                  90                  95

Gly Gly Ser Trp Ser Lys Thr Val Gly Ser Val Gly Glu Ile Pro Leu
            100                 105                 110
```

Gln Gly Asp Phe Ser Ala Glu His Met Ile Phe Gly Val Glu Gly Ala
            115                 120                 125

Asp Pro Val Arg Arg Glu Arg Leu Ile Glu Leu Leu Asp Ile Asp Leu
        130                 135                 140

Arg Trp Arg Met His Lys Val Ser Asp Gly Gln Arg Arg Val Gln
145                 150                 155                 160

Ile Cys Met Gly Leu Leu Gln Pro Phe Lys Val Leu Leu Asp Glu
                165                 170                 175

Val Thr Val Asp Leu Asp Val Val Ala Arg Leu Asp Leu Leu Asn Phe
            180                 185                 190

Phe Lys Glu Glu Cys Asp Glu Arg Gly Gly Thr Ile Val Tyr Ala Thr
            195                 200                 205

His Ile Phe Asp Gly Leu Glu Thr Trp Ala Thr His Leu Ala Tyr Ile
        210                 215                 220

Gln Asp Gly Glu Leu Arg Arg Ala Glu Lys Leu Ser Glu Ile Gly Glu
225                 230                 235                 240

Leu Lys Asn Ser Ala Asn Leu Ser Val Val Glu Ser Trp Leu Arg
                245                 250                 255

Ser Glu Ile Lys Leu Glu Lys Lys Lys Pro Val Asn Pro Pro Ala Ala
            260                 265                 270

Gln Ile Gln Lys Thr Ser Pro Phe Gly Thr Ser Pro Phe Val Ser Ser
        275                 280                 285

Arg His Met Ala Tyr Tyr Arg
        290                 295

<210> SEQ ID NO 36
<211> LENGTH: 299
<212> TYPE: PRT
<213> ORGANISM: Populus euphratica
<220> FEATURE:
<221> NAME/KEY: MISC_FEATURE
<222> LOCATION: (1)..(299)
<223> OTHER INFORMATION: ABC Transporter

<400> SEQUENCE: 36

Met Ala Glu Lys Ala Ser Gln Ser Ile Glu Lys Gly Gly Glu Asn Glu
1               5                   10                  15

Lys Ala Asn Ser Ile Ser Ile Trp Gly Met Gln Phe Ala Tyr Ala Gly
            20                  25                  30

Gln His Pro Leu Phe Tyr Asp Phe Asn Leu Asn Ile Ser Pro Gly Ser
        35                  40                  45

Arg Cys Leu Leu Val Gly Ala Asn Gly Ser Gly Lys Thr Thr Leu Leu
    50                  55                  60

Lys Ile Met Ala Gly Lys His Met Val Gly Gly Arg Asp Val Val Arg
65                  70                  75                  80

Val Ile Asn Gly Ser Ala Phe His Asp Thr Gln Leu Val Cys Ser Gly
                85                  90                  95

Asp Leu Ala Tyr Leu Gly Gly Ser Trp Ser Lys Thr Val Gly Ser Ala
            100                 105                 110

Gly Glu Ile Pro Leu Gln Gly Asp Phe Ser Ala Glu His Met Ile Phe
        115                 120                 125

Gly Val Glu Gly Thr Asp Pro Val Arg Arg Glu Lys Leu Ile Asp Leu
    130                 135                 140

Leu Asp Ile Asp Leu Gln Trp Arg Met His Lys Val Ser Asp Gly Gln
145                 150                 155                 160

```
Arg Arg Arg Val Gln Ile Cys Met Gly Leu Leu His Pro Phe Lys Val
            165                 170                 175

Leu Leu Leu Asp Glu Val Thr Val Asp Leu Asp Val Val Ala Arg Met
        180                 185                 190

Asp Leu Leu Glu Phe Phe Lys Glu Glu Cys Asp Gln Arg Gly Ala Thr
            195                 200                 205

Ile Val Tyr Ala Thr His Ile Phe Asp Gly Leu Glu Thr Trp Ala Thr
    210                 215                 220

His Leu Ala Tyr Ile Gln Asp Gly Glu Leu Arg Arg Ala Glu Lys Leu
225                 230                 235                 240

Thr Glu Val His Glu Leu Lys Ser Ser Ala Asn Leu Leu Ser Val Val
                245                 250                 255

Glu Ser Trp Leu Arg His Glu Thr Lys Ser Glu Lys Lys Lys Pro Thr
            260                 265                 270

Asn Pro Pro Ala Gln Asn Gln Lys Thr Ser Pro Leu Gly Ser Ser Pro
        275                 280                 285

Phe Met Ser Ser Arg His Met Ala Tyr Tyr Arg
    290                 295

<210> SEQ ID NO 37
<211> LENGTH: 300
<212> TYPE: PRT
<213> ORGANISM: Manihot esculenta
<220> FEATURE:
<221> NAME/KEY: MISC_FEATURE
<222> LOCATION: (1)..(300)
<223> OTHER INFORMATION: ABC Transporter

<400> SEQUENCE: 37

Met Ala Glu Lys Ala Trp Lys Ser Arg Glu Ser Glu Asp Asp Glu Asn
1               5                   10                  15

Gly Lys Gln Asn Ser Ile Ser Val Arg Gly Met Gln Phe Ala Tyr Glu
            20                  25                  30

Gly Gln His Pro Leu Phe Tyr Asp Phe Asn Leu Asn Ile Pro Pro Gly
        35                  40                  45

Ser Arg Cys Leu Leu Val Gly Ala Asn Gly Ser Gly Lys Thr Thr Leu
    50                  55                  60

Leu Lys Ile Leu Ala Gly Lys His Met Val Gly Gly Arg Asp Val Val
65              70                  75                  80

Arg Val Leu Asn Arg Ser Ala Phe His Asp Thr Gln Leu Val Cys Gly
                85                  90                  95

Gly Asp Leu Ala Tyr Leu Gly Gly Ser Trp Ser Lys Thr Val Gly Ser
            100                 105                 110

Ala Gly Glu Ile Pro Leu Gln Gly Asp Phe Ser Ala Glu His Met Ile
        115                 120                 125

Phe Gly Val Glu Gly Val Asp Pro Ala Arg Arg Glu Lys Leu Ile Asp
    130                 135                 140

Leu Leu Asp Ile Asp Leu Glu Trp Arg Met His Lys Val Ser Asp Gly
145                 150                 155                 160

Gln Arg Arg Arg Val Gln Ile Cys Met Gly Leu Leu Val Pro Phe Lys
                165                 170                 175

Val Leu Leu Leu Asp Glu Val Thr Val Asp Leu Asp Val Val Ala Arg
            180                 185                 190

Met Asp Leu Leu Glu Phe Phe Arg Glu Glu Cys Glu Gln Arg Gly Ala
        195                 200                 205

Thr Leu Val Tyr Ala Thr His Ile Phe Asp Gly Leu Glu Thr Trp Ala
    210                 215                 220
```

```
                  210                 215                 220
Thr His Leu Ala Tyr Ile Gln Asp Gly Glu Leu Arg Lys Ser Glu Lys
225                 230                 235                 240

Leu Thr Asp Val His Glu Leu Lys Ser Ser Ala Asn Leu Leu Ser Val
                245                 250                 255

Val Glu Ser Trp Leu Arg Ser Glu Thr Lys His Glu Lys Lys Lys Pro
            260                 265                 270

Thr Asn Pro Pro Ala Gln Asn Gln Lys Thr Ser Pro Phe Gly Thr Ser
        275                 280                 285

Pro Phe Met Ser Ser Arg His Met Ala Tyr Tyr Arg
    290                 295                 300

<210> SEQ ID NO 38
<211> LENGTH: 294
<212> TYPE: PRT
<213> ORGANISM: Cicer arietinum
<220> FEATURE:
<221> NAME/KEY: MISC_FEATURE
<222> LOCATION: (1)..(294)
<223> OTHER INFORMATION: ABC Transporter

<400> SEQUENCE: 38

Met Ala Ile Glu Gln Glu Gln Glu Asn Ala Asn Ser Asn Gly Ile Arg
1               5                   10                  15

Val Gln Gly Met Gln Phe Ser Tyr Asp Gly Leu Gln Gln Pro Pro Leu
            20                  25                  30

Phe Leu Asp Phe Asn Leu Gln Val Ser Pro Gly Ser Arg Cys Leu Leu
        35                  40                  45

Val Gly Ala Asn Gly Ser Gly Lys Thr Thr Leu Leu Lys Ile Leu Ala
    50                  55                  60

Gly Lys His Met Val Gly Gly Lys Asp Val Val Arg Val Leu Asn Cys
65                  70                  75                  80

Ser Ala Phe His Asp Thr Gln Leu Val Cys Ser Gly Asp Leu Ala Tyr
                85                  90                  95

Leu Gly Gly Ser Trp Ser Lys Asn Val Gly Ser Ala Gly Asp Ile Pro
            100                 105                 110

Leu Gln Gly Asp Phe Ser Ala Glu His Met Ile Phe Gly Val Glu Gly
        115                 120                 125

Val Asn Pro Asp Arg Arg Asp Lys Leu Ile Glu Leu Leu Asp Ile Asp
    130                 135                 140

Leu Gln Trp Arg Met His Lys Val Ser Asp Gly Gln Arg Arg Arg Val
145                 150                 155                 160

Gln Ile Cys Leu Gly Leu Leu His Pro Tyr Lys Val Leu Leu Leu Asp
                165                 170                 175

Glu Val Thr Val Asp Leu Asp Val Val Thr Arg Met Asp Leu Leu Glu
            180                 185                 190

Phe Phe Lys Glu Glu Cys Glu Gln Arg Glu Ala Thr Ile Val Tyr Ala
        195                 200                 205

Thr His Ile Phe Asp Gly Leu Glu Thr Trp Ala Thr His Leu Ala Tyr
    210                 215                 220

Ile Gln Glu Gly Glu Leu Arg Arg Ala Glu Lys Leu Ser Asp Val Asn
225                 230                 235                 240

Glu Leu Lys Ser Ser Ile Asn Leu Leu Ser Val Val Glu Ser Trp Leu
                245                 250                 255

Arg Ala Glu Thr Lys Leu Glu Lys Lys Pro Val Leu Asn Thr Ser
            260                 265                 270
```

```
Gln Ser Gln Gly Asn Ser Phe Ala Ser Ser Pro Phe Ala Ser Arg
        275                 280                 285

His Met Ala Tyr Tyr Arg
    290

<210> SEQ ID NO 39
<211> LENGTH: 299
<212> TYPE: PRT
<213> ORGANISM: Corchorus olitorius
<220> FEATURE:
<221> NAME/KEY: MISC_FEATURE
<222> LOCATION: (1)..(299)
<223> OTHER INFORMATION: ABC Transporter

<400> SEQUENCE: 39

Met Ala Glu Gln Thr Phe Cys Lys Ser Arg Glu Gly Asp Glu Asn Ala
1               5                   10                  15

Glu Ser Lys Ser Ile Arg Val Cys Gly Met Gln Phe Ala Tyr Glu Leu
            20                  25                  30

Gln His Pro Leu Phe Val Asp Phe Asn Leu Glu Ile Ala Pro Gly Ser
        35                  40                  45

Arg Cys Leu Leu Val Gly Ala Asn Gly Ser Gly Lys Thr Thr Leu Leu
    50                  55                  60

Lys Ile Leu Ala Gly Lys His Met Val Gly Arg Asp Val Arg
65                  70                  75                  80

Val Leu Asn Arg Ser Ala Phe His Asp Thr Gln Leu Val Cys Gly Gly
                85                  90                  95

Asp Leu Ala Tyr Leu Gly Gly Ser Trp Ser Lys Thr Ile Gly Ser Ala
            100                 105                 110

Gly Glu Val Pro Leu Gln Gly Asp Phe Ser Ala Glu His Met Ile Phe
        115                 120                 125

Gly Val Glu Gly Ile Asp Pro Val Arg Arg Glu Lys Leu Ile Glu Leu
    130                 135                 140

Leu Asp Ile Asp Leu Gln Trp Arg Met His Lys Val Ser Asp Gly Gln
145                 150                 155                 160

Arg Arg Arg Val Gln Ile Cys Met Gly Leu Leu His Pro Phe Gln Val
                165                 170                 175

Leu Leu Leu Asp Glu Val Thr Val Asp Leu Asp Val Val Ala Arg Met
            180                 185                 190

Asp Leu Leu Asp Phe Phe Lys Glu Glu Cys Glu Gln Arg Gly Ala Thr
        195                 200                 205

Val Val Tyr Ala Thr His Ile Phe Asp Gly Leu Glu Thr Trp Ala Thr
    210                 215                 220

His Leu Ala Tyr Ile Gln Asp Gly Glu Leu Lys Lys Ser Glu Lys Ser
225                 230                 235                 240

Thr Glu Ile Asn Glu Leu Lys Ser Ser Glu Asn Leu Leu Ser Val Val
                245                 250                 255

Glu Ala Trp Leu Arg Ser Glu Thr Lys Cys Glu Lys Lys Lys Ala Ile
            260                 265                 270

Asn Asn Ser Ala Gln Val Gln Lys Thr Ser Pro Phe Gly Thr Ser Pro
        275                 280                 285

Phe Met Ser Ser Arg His Met Ala Tyr Tyr Arg
    290                 295

<210> SEQ ID NO 40
<211> LENGTH: 300
```

```
<212> TYPE: PRT
<213> ORGANISM: Hevea brasiliensis
<220> FEATURE:
<221> NAME/KEY: MISC_FEATURE
<222> LOCATION: (1)..(300)
<223> OTHER INFORMATION: ABC Transporter

<400> SEQUENCE: 40

Met Ala Glu Lys Arg Trp Lys Ser Arg Glu Ser Glu Asp Glu Asn
1               5                   10                  15

Asp Lys Gln Tyr Ser Ile Ser Val Cys Gly Met Gln Phe Ala Tyr Glu
            20                  25                  30

Gly Gln Pro Pro Leu Phe Tyr Asp Phe Asn Leu Asn Ile Pro Pro Gly
        35                  40                  45

Ser Arg Cys Leu Leu Val Gly Ala Asn Gly Ser Gly Lys Thr Thr Leu
    50                  55                  60

Leu Lys Ile Leu Ala Gly Lys His Met Val Gly Gly Arg Asp Val Val
65                  70                  75                  80

Arg Val Leu Asn Leu Ser Ala Phe His Asp Thr Gln Leu Val Cys Gly
                85                  90                  95

Gly Asp Leu Ala Tyr Leu Gly Gly Ser Trp Thr Lys Thr Val Gly Ser
            100                 105                 110

Ala Gly Glu Ile Pro Leu Gln Gly Asp Phe Ser Ala Glu His Met Ile
        115                 120                 125

Phe Gly Val Glu Gly Ile Asp Pro Ala Arg Arg Glu Lys Leu Ile Asp
    130                 135                 140

Leu Leu Asp Ile Asp Leu Gln Trp Arg Met His Lys Val Ser Asp Gly
145                 150                 155                 160

Gln Arg Arg Arg Val Gln Ile Cys Met Gly Leu Leu Val Pro Phe Lys
                165                 170                 175

Val Leu Leu Leu Asp Glu Val Thr Val Asp Leu Asp Val Val Ala Arg
            180                 185                 190

Leu Asp Leu Leu Glu Phe Phe Lys Glu Glu Cys Glu Gln Arg Gly Ala
        195                 200                 205

Thr Leu Val Tyr Ala Thr His Ile Phe Asp Gly Leu Glu Thr Trp Ala
    210                 215                 220

Thr His Leu Ala Tyr Ile Gln Asp Gly Glu Leu Arg Arg Ser Glu Lys
225                 230                 235                 240

Leu Thr Glu Val His Glu Leu Lys Ser Ser Ala Asn Leu Leu Ser Val
                245                 250                 255

Val Glu Ser Trp Leu Arg Ser Glu Thr Arg His Glu Lys Lys Pro
            260                 265                 270

Thr Asn Pro Pro Ala Gln Asn Gln Lys Thr Ser Pro Phe Gly Thr Ser
        275                 280                 285

Pro Phe Met Ser Ser Arg His Met Ala Tyr Tyr Arg
    290                 295                 300

<210> SEQ ID NO 41
<211> LENGTH: 298
<212> TYPE: PRT
<213> ORGANISM: Populus euphratica
<220> FEATURE:
<221> NAME/KEY: MISC_FEATURE
<222> LOCATION: (1)..(298)
<223> OTHER INFORMATION: ABC Transporter

<400> SEQUENCE: 41

Met Ala Glu Lys Ala Ser Gln Ser Asp Gly Gly Gly Glu Asn Glu Lys
```

```
                1               5                   10                  15
        Glu Asn Ser Ile Ser Ile Cys Gly Met Gln Tyr Ala Tyr Pro Gly Gln
                        20                  25                  30

His Pro Leu Phe Tyr Glu Phe Asn Leu Asn Ile Ser Pro Gly Ser Arg
                        35                  40                  45

Cys Leu Leu Val Gly Ala Asn Gly Ser Gly Lys Thr Thr Leu Leu Lys
                        50                  55                  60

Ile Met Ala Gly Lys His Met Val Gly Arg Asp Val Val Arg Val
         65                 70                  75                  80

Ile Asn Gly Ser Ala Phe His Asp Thr Gln Leu Val Cys Ser Gly Asp
                        85                  90                  95

Leu Ala Tyr Leu Gly Gly Ser Trp Ser Lys Thr Val Gly Ser Ala Gly
                        100                 105                 110

Glu Ile Pro Leu Gln Gly Asp Phe Ser Ala Glu His Met Ile Phe Gly
                        115                 120                 125

Val Glu Gly Thr Asp Pro Val Arg Arg Glu Lys Leu Ile Glu Leu Leu
                        130                 135                 140

Asp Ile Asp Leu Lys Trp Arg Met His Lys Val Ser Asp Gly Gln Arg
        145                 150                 155                 160

Arg Arg Val Gln Ile Cys Met Gly Leu Leu His Pro Phe Lys Val Leu
                        165                 170                 175

Leu Leu Asp Glu Val Thr Val Asp Leu Asp Val Val Ala Arg Met Asp
                        180                 185                 190

Leu Leu Glu Phe Phe Lys Glu Glu Cys Asp Gln Arg Gly Ala Thr Ile
                        195                 200                 205

Val Tyr Ala Thr His Ile Phe Asp Gly Leu Glu Thr Trp Ala Thr His
                        210                 215                 220

Leu Ala Tyr Ile Gln Asp Gly Glu Leu Lys Arg Ala Lys Lys Leu Thr
        225                 230                 235                 240

Glu Ile His Glu Leu Lys Asn Ser Ala Thr Leu Leu Ser Val Val Glu
                        245                 250                 255

Ser Trp Leu Arg Ser Glu Thr Lys Asn Glu Lys Lys Lys Pro Ala Asn
                        260                 265                 270

Pro Pro Ala Gln Asn Gln Lys Thr Ser Pro Phe Gly Ser Ser Pro Phe
                        275                 280                 285

Met Ser Ser Arg His Met Ala Phe Tyr Arg
                        290                 295

<210> SEQ ID NO 42
        <211> LENGTH: 301
        <212> TYPE: PRT
        <213> ORGANISM: Prunus mume
        <220> FEATURE:
        <221> NAME/KEY: MISC_FEATURE
        <222> LOCATION: (1)..(301)
        <223> OTHER INFORMATION: ABC Transporter

<400> SEQUENCE: 42

Met Ala Gly Arg Val Ser Glu Thr Ser Asn Pro Arg Ala Glu Gly Glu
        1               5                   10                  15

Gly Glu Thr Ser Ser Gly Ile Arg Val His Gly Met Gln Phe Ser Tyr
                        20                  25                  30

Asp Ala Gln Pro Pro Leu Phe Cys Asp Phe Asn Leu Asn Ile Ala Pro
                        35                  40                  45

Gly Ser Arg Cys Leu Leu Val Gly Ala Asn Gly Ser Gly Lys Thr Thr
                        50                  55                  60
```

Leu Leu Lys Ile Leu Ala Gly Lys Gln Met Val Gly Arg Asp Val
65                  70                  75                  80

Val Arg Val Leu Asn Cys Ser Ala Phe His Asp Thr His Leu Val Cys
                85                  90                  95

Ser Gly Asp Leu Ala Tyr Leu Gly Gly Ser Trp Ser Lys Ser Val Gly
            100                 105                 110

Ser Ala Gly Glu Leu Pro Leu Gln Gly Asp Phe Ser Ala Glu His Met
        115                 120                 125

Ile Phe Gly Val Glu Gly Thr Asp Pro Val Arg Arg Asp Lys Leu Ile
130                 135                 140

Glu Leu Leu Asp Ile Asn Leu Gln Trp Arg Met His Lys Val Ser Asp
145                 150                 155                 160

Gly Gln Arg Arg Arg Val Gln Ile Cys Met Gly Leu Leu His Pro Phe
                165                 170                 175

Lys Val Leu Leu Leu Asp Glu Val Thr Val Asp Leu Asp Val Val Ala
            180                 185                 190

Arg Leu Asp Leu Leu Asp Phe Phe Lys Glu Glu Cys Glu Gln Arg Gly
        195                 200                 205

Ala Thr Ile Val Tyr Ala Thr His Ile Phe Asp Gly Leu Glu Thr Trp
210                 215                 220

Ala Thr His Leu Ala Tyr Ile Gln Asp Gly Glu Leu Lys Arg Ala Glu
225                 230                 235                 240

Lys Leu Ser Glu Val Asn Glu Leu Lys Ser Ser Ala Asn Leu Leu Ser
                245                 250                 255

Val Val Glu Ser Trp Leu Arg Ala Glu Thr Lys His Glu Lys Lys Arg
            260                 265                 270

Ser Thr Asn Pro Pro Ala Gln Thr Gln Lys Thr Ser Pro Phe Ala Thr
        275                 280                 285

Ser Pro Phe Met Ser Ser Arg His Met Ala Tyr Tyr Arg
    290                 295                 300

<210> SEQ ID NO 43
<211> LENGTH: 300
<212> TYPE: PRT
<213> ORGANISM: Gossypium raimondii
<220> FEATURE:
<221> NAME/KEY: MISC_FEATURE
<222> LOCATION: (1)..(300)
<223> OTHER INFORMATION: ABC Transporter

<400> SEQUENCE: 43

Met Ala Glu Gln Ala Cys Cys Arg Ser Gly Glu Gly Lys Glu Asn Gly
1               5                   10                  15

Gly Asp Ser Gln Gly Ile Thr Val Cys Gly Met Gln Phe Ala Tyr Glu
            20                  25                  30

Leu Gln His Pro Leu Phe Phe Asp Phe Asn Leu Asp Ile Ala Arg Gly
        35                  40                  45

Ser Arg Cys Leu Leu Val Gly Ala Asn Gly Ser Gly Lys Thr Thr Leu
    50                  55                  60

Leu Lys Ile Leu Ala Gly Lys His Met Val Gly Gly Arg Glu Val Val
65                  70                  75                  80

Arg Val Leu Asn Arg Ser Ala Phe His Asp Thr Gln Leu Val Cys Gly
                85                  90                  95

Gly Asp Leu Ala Tyr Leu Gly Gly Ser Trp Ser Lys Thr Ile Gly Ser
            100                 105                 110

```
Ala Gly Glu Val Pro Leu Gln Gly Asp Phe Ser Ala Glu His Met Ile
            115                 120                 125

Phe Gly Val Glu Gly Ile Asp Pro Val Arg Arg Asp Lys Leu Ile Glu
130                 135                 140

Leu Leu Asp Ile Asp Leu Gln Trp Arg Met His Lys Val Ser Asp Gly
145                 150                 155                 160

Gln Arg Arg Arg Val Gln Ile Cys Met Gly Leu Leu His Pro Phe Gln
                165                 170                 175

Val Leu Leu Asp Glu Val Thr Val Asp Leu Asp Val Val Ala Arg
            180                 185                 190

Met Asp Leu Leu Asp Phe Phe Lys Glu Glu Cys Glu Gln Arg Gly Ala
            195                 200                 205

Thr Val Val Tyr Ala Thr His Ile Phe Asp Gly Leu Glu Thr Trp Ala
            210                 215                 220

Thr His Leu Ala Tyr Ile Gln Asp Gly Gln Leu Lys Arg Ser Glu Lys
225                 230                 235                 240

Leu Thr Glu Ile Asn Glu Leu Lys Ser Ser Glu Asn Leu Leu Ser Val
                245                 250                 255

Val Glu Ala Trp Leu Arg Ser Glu Thr Lys Cys Glu Lys Lys Lys Pro
            260                 265                 270

Ser Asn Ser Pro Ala Gln Val Gln Lys Ser Ser Pro Phe Gly Thr Ser
            275                 280                 285

Pro Phe Met Ser Ser Arg His Met Ala Tyr Tyr Arg
            290                 295                 300

<210> SEQ ID NO 44
<211> LENGTH: 300
<212> TYPE: PRT
<213> ORGANISM: Ziziphus jujuba
<220> FEATURE:
<221> NAME/KEY: MISC_FEATURE
<222> LOCATION: (1)..(300)
<223> OTHER INFORMATION: ABC Transporter

<400> SEQUENCE: 44

Met Glu Asp Arg Gly Ser Leu Lys Pro Glu Glu Glu Gly Ser Lys Tyr
1               5                   10                  15

Glu Ser Ser Ser Ile Lys Val Tyr Gly Met Gln Phe Ser Tyr Asp
                20                  25                  30

Gly Gln Thr Pro Leu Phe Ala Asp Phe Asn Leu Asp Ile Ser Pro Gly
            35                  40                  45

Ser Arg Cys Leu Leu Val Gly Ala Asn Gly Ser Gly Lys Thr Thr Leu
    50                  55                  60

Leu Lys Ile Leu Ala Gly Lys His Met Val Gly Glu Arg Asp Val Val
65                  70                  75                  80

Arg Val Leu Asn Tyr Ser Ala Phe His Asp Thr His Leu Val Cys Ser
                85                  90                  95

Gly Asp Leu Ala Tyr Leu Gly Gly Ser Trp Ser Lys Thr Val Gly Ser
            100                 105                 110

Ala Gly Glu Ile Pro Leu Gln Gly Asp Phe Ser Ala Glu His Met Ile
            115                 120                 125

Phe Gly Val Glu Gly Ala Asp Pro Val Arg Arg Asp Lys Leu Ile Glu
130                 135                 140

Leu Leu Asp Ile Asp Leu Gln Trp Arg Met His Lys Val Ser Asp Gly
145                 150                 155                 160

Gln Arg Arg Arg Val Gln Ile Cys Met Gly Leu Leu His Pro Phe Lys
```

```
                165                 170                 175
Val Leu Leu Leu Asp Glu Val Thr Val Asp Leu Asp Val Val Ala Arg
            180                 185                 190

Met Asp Leu Leu Glu Phe Phe Lys Glu Glu Cys Asp Gln Arg Gly Ala
            195                 200                 205

Thr Ile Val Tyr Ala Thr His Ile Phe Asp Gly Leu Glu Thr Trp Ala
            210                 215                 220

Thr His Leu Ala Tyr Ile Gln Asp Gly Asp Leu Arg Arg Ala Glu Lys
225                 230                 235                 240

Leu Ser Glu Val Asn Glu Leu Lys Asn Ser Ala Asn Leu Leu Ser Val
            245                 250                 255

Val Glu Ser Trp Leu Arg Ser Glu Ile Lys His Glu Lys Lys Lys Pro
            260                 265                 270

Ile Asn Pro Pro Ser Gln Ile Arg Lys Thr Ser Pro Phe Gly Thr Ser
            275                 280                 285

Pro Phe Val Ser Ser Arg His Met Ala Tyr Tyr Arg
            290                 295                 300

<210> SEQ ID NO 45
<211> LENGTH: 294
<212> TYPE: PRT
<213> ORGANISM: Citrus clementina
<220> FEATURE:
<221> NAME/KEY: MISC_FEATURE
<222> LOCATION: (1)..(294)
<223> OTHER INFORMATION: ABC Transporter

<400> SEQUENCE: 45

Met Ala Asp Gly Met Asn Glu Asn Glu Lys Leu Asn Ser Ile Lys Val
1               5                   10                  15

Cys Gly Met Gln Phe Ser Tyr Glu Gly Asn Asp Lys Pro Pro Leu Phe
            20                  25                  30

Tyr Asp Phe Asn Leu Asp Ile Ser Pro Gly Ser Arg Cys Leu Leu Val
            35                  40                  45

Gly Ala Asn Gly Ser Gly Lys Thr Thr Leu Leu Lys Ile Leu Ala Gly
        50                  55                  60

Lys His Met Val Gly Gly Arg Asp Val Val Gln Val Leu Asn Arg Ser
65                  70                  75                  80

Ser Phe His Asp Thr Gln Leu Val Cys Ser Gly Asp Leu Ser Tyr Leu
                85                  90                  95

Gly Gly Ser Trp Ser Lys Thr Val Gly Ser Ala Gly Glu Ile Pro Leu
            100                 105                 110

Gln Gly Asp Phe Ser Ala Glu His Met Ile Phe Gly Val Glu Gly Ser
            115                 120                 125

Asp Pro Val Arg Arg Glu Arg Leu Ile Glu Leu Asp Ile Asp Leu
        130                 135                 140

Gln Trp Arg Met His Lys Val Ser Asp Gly Gln Arg Arg Val Gln
145                 150                 155                 160

Ile Cys Met Gly Leu Leu His Pro Phe Lys Val Leu Leu Asp Glu
            165                 170                 175

Ile Thr Val Asp Leu Asp Val Val Ala Arg Met Asp Leu Leu Asp Phe
            180                 185                 190

Phe Lys Asp Glu Cys Glu Gln Arg Gly Ala Thr Ile Val Tyr Ala Thr
            195                 200                 205

His Ile Phe Asp Gly Leu Glu Thr Trp Ala Thr His Leu Ala Tyr Ile
            210                 215                 220
```

Gln Asp Gly Glu Leu Arg Arg Ala Glu Lys Leu Ala Glu Leu Asp Glu
225                 230                 235                 240

Leu Arg Asn Ser Thr Asn Leu Leu Ser Val Val Glu Ser Trp Leu Arg
            245                 250                 255

Ser Glu Thr Lys Leu Glu Lys Lys Arg Pro Val Asp Pro Pro Lys Gln
            260                 265                 270

Val Gln Lys Thr Ser Pro Phe Gly Ser Ser Pro Phe Met Ser Ser Arg
            275                 280                 285

His Met Ala Tyr Tyr Arg
        290

<210> SEQ ID NO 46
<211> LENGTH: 336
<212> TYPE: PRT
<213> ORGANISM: Ipomoea nil
<220> FEATURE:
<221> NAME/KEY: MISC_FEATURE
<222> LOCATION: (1)..(336)
<223> OTHER INFORMATION: ABC Transporter

<400> SEQUENCE: 46

Met Phe Ser Arg Arg Val Asn Ile Gln Ser Leu Glu Glu Val Val Glu
1               5                   10                  15

Val Val Arg Glu Glu Thr Leu Arg Arg Leu Leu Tyr Asn Thr Pro
            20                  25                  30

Pro Glu Thr Pro Leu Ile Glu Tyr Arg Arg Pro Arg Glu Lys Glu Thr
            35                  40                  45

Lys Met Ala Ala Glu Ser Asn Ser Ile Gln Val Ser Gly Met Gln Phe
    50                  55                  60

Gly Tyr Asp Phe Gln Thr Pro Leu Phe Phe Asp Phe Ser Leu Lys Val
65                  70                  75                  80

Ser Pro Gly Ser Arg Cys Leu Leu Val Gly Ala Asn Gly Ser Gly Lys
                85                  90                  95

Thr Thr Leu Leu Arg Ile Leu Ala Gly Lys His Leu Val Gly Gly Lys
            100                 105                 110

Asp Val Val Arg Val Leu Asn Phe Ser Ala Phe His Asp Thr His Leu
            115                 120                 125

Val Cys Ser Gly Asp Leu Ala Tyr Leu Gly Glu Ser Trp Ser Lys Asn
130                 135                 140

Val Gly Ser Ala Gly Glu Ile Pro Leu Gln Gly Asp Phe Ser Ala Glu
145                 150                 155                 160

His Met Ile Phe Gly Val Asp Gly Val Asp Pro Ile Arg Arg Glu Lys
                165                 170                 175

Leu Ile Glu Leu Leu Asp Ile Asp Leu Gln Trp Arg Met His Lys Val
            180                 185                 190

Ser Asp Gly Gln Arg Arg Arg Val Gln Ile Cys Met Gly Leu Leu His
            195                 200                 205

Pro Tyr Lys Val Leu Leu Leu Asp Glu Val Thr Val Asp Leu Asp Val
        210                 215                 220

Val Ala Arg Met Asp Leu Leu Asp Phe Phe Lys Glu Glu Cys Glu Gln
225                 230                 235                 240

Arg Gly Ala Thr Val Val Tyr Ala Thr His Ile Phe Asp Gly Leu Glu
                245                 250                 255

Thr Trp Ala Thr Asp Leu Val Tyr Val Gln Asp Gly Val Leu Lys Arg
            260                 265                 270

```
Ser Glu Lys Leu Ser Glu Leu Ala Glu Leu Lys Thr Lys Pro Asn Leu
            275                 280                 285

Leu Ser Val Val Glu Thr Trp Leu Arg Ser Glu Thr Pro Ile Glu Lys
        290                 295                 300

Lys Lys Ala Ser Lys Asn Pro Ser Ala Val Lys Thr Thr Ser Ser Pro
305                 310                 315                 320

Phe Asp Ala Ser Pro Phe Arg Ser Ser Arg His Met Ala Tyr Tyr Arg
                325                 330                 335

<210> SEQ ID NO 47
<211> LENGTH: 301
<212> TYPE: PRT
<213> ORGANISM: Prunus persica
<220> FEATURE:
<221> NAME/KEY: MISC_FEATURE
<222> LOCATION: (1)..(301)
<223> OTHER INFORMATION: ABC Transporter

<400> SEQUENCE: 47

Met Ala Gly Arg Val Ser Glu Thr Ser Asn Pro Arg Ala Glu Gly Glu
1               5                   10                  15

Gly Glu Thr Ser Ser Gly Ile Arg Val His Gly Met Gln Phe Ser Tyr
            20                  25                  30

Asp Ala Gln Pro Pro Leu Phe Cys Asp Phe Asn Leu Asn Ile Ala Pro
        35                  40                  45

Gly Ser Arg Cys Leu Leu Val Gly Ala Asn Gly Ser Gly Lys Thr Thr
    50                  55                  60

Leu Leu Lys Ile Leu Ala Gly Lys Gln Met Val Gly Gly Arg Asp Val
65                  70                  75                  80

Val Arg Val Leu Asn Cys Ser Ala Phe His Asp Thr His Leu Val Cys
                85                  90                  95

Ser Gly Asp Leu Ala Tyr Leu Gly Gly Ser Trp Ser Lys Ser Val Gly
            100                 105                 110

Ser Ala Gly Glu Leu Pro Leu Gln Gly Asp Phe Ser Ala Glu His Met
        115                 120                 125

Ile Phe Gly Val Glu Gly Thr Asp Pro Val Arg Arg Asp Lys Leu Ile
    130                 135                 140

Glu Leu Leu Asp Ile Asn Leu Gln Trp Arg Met His Lys Val Ser Asp
145                 150                 155                 160

Gly Gln Arg Arg Arg Val Gln Ile Cys Met Gly Leu Leu His Pro Phe
                165                 170                 175

Lys Val Leu Leu Leu Asp Glu Val Thr Val Asp Leu Asp Val Val Ala
            180                 185                 190

Arg Leu Asp Leu Leu Asp Phe Phe Lys Glu Glu Cys Glu Gln Arg Arg
        195                 200                 205

Ala Thr Ile Val Tyr Ala Thr His Ile Phe Asp Gly Leu Glu Thr Trp
    210                 215                 220

Ala Thr His Leu Ala Tyr Ile Gln Asp Gly Glu Leu Lys Arg Ala Glu
225                 230                 235                 240

Lys Leu Ser Glu Val Asn Glu Leu Lys Ser Ser Ala Asn Leu Leu Ser
                245                 250                 255

Val Val Glu Ser Trp Leu Arg Ala Glu Thr Lys His Glu Lys Lys Arg
            260                 265                 270

Ser Thr Asn Pro Pro Ala Gln Thr Gln Lys Thr Ser Ala Phe Ala Thr
        275                 280                 285

Ser Pro Phe Met Ser Ser Arg His Met Ala Tyr Tyr Arg
    290                 295                 300
```

```
<210> SEQ ID NO 48
<211> LENGTH: 300
<212> TYPE: PRT
<213> ORGANISM: Gossypium hirsutum
<220> FEATURE:
<221> NAME/KEY: MISC_FEATURE
<222> LOCATION: (1)..(300)
<223> OTHER INFORMATION: ABC Transporter

<400> SEQUENCE: 48

Met Ala Glu Gln Ala Cys Cys Arg Ser Gly Glu Gly Lys Glu Asn Gly
1               5                   10                  15

Gly Asp Leu Gln Gly Ile Thr Val Cys Gly Met Gln Phe Ala Tyr Glu
            20                  25                  30

Leu Gln His Pro Leu Phe Phe Asp Phe Asn Leu Asp Ile Ala Arg Gly
        35                  40                  45

Ser Arg Cys Leu Leu Val Gly Ala Asn Gly Ser Gly Lys Thr Thr Leu
    50                  55                  60

Leu Lys Ile Leu Ala Gly Lys His Met Val Gly Gly Arg Asp Val Val
65                  70                  75                  80

Arg Val Leu Asn Arg Ser Ala Phe His Asp Thr Gln Leu Val Cys Gly
                85                  90                  95

Gly Asp Leu Ala Tyr Leu Gly Gly Ser Trp Ser Lys Thr Ile Gly Ser
            100                 105                 110

Ala Gly Glu Val Pro Leu Gln Gly Asp Phe Ser Ala Glu His Met Ile
        115                 120                 125

Phe Gly Val Glu Gly Ile Asp Pro Val Arg Arg Asp Lys Leu Ile Glu
    130                 135                 140

Leu Leu Asp Ile Asp Leu Gln Trp Arg Met His Lys Val Ser Asp Gly
145                 150                 155                 160

Gln Arg Arg Arg Val Gln Ile Cys Met Gly Leu Leu His Pro Phe Gln
                165                 170                 175

Val Leu Leu Leu Asp Glu Val Thr Val Asp Leu Asp Val Val Ala Arg
            180                 185                 190

Met Asp Leu Leu Asp Phe Phe Lys Glu Glu Cys Glu Gln Arg Gly Ala
        195                 200                 205

Thr Val Val Tyr Ala Thr His Ile Phe Asp Gly Leu Glu Thr Trp Ala
    210                 215                 220

Thr His Leu Ala Tyr Ile Gln Asp Gly Gln Leu Lys Arg Ser Glu Lys
225                 230                 235                 240

Leu Thr Glu Ile Asn Glu Leu Lys Ser Ser Glu Asn Leu Leu Ser Val
                245                 250                 255

Val Glu Ala Trp Leu Arg Ser Glu Thr Lys Cys Glu Lys Lys Lys Ser
            260                 265                 270

Ser Asn Ser Pro Ala Gln Val Gln Lys Ser Ser Pro Phe Gly Thr Ser
        275                 280                 285

Pro Phe Met Ser Ser Arg His Met Ala Tyr Tyr Arg
    290                 295                 300

<210> SEQ ID NO 49
<211> LENGTH: 274
<212> TYPE: PRT
<213> ORGANISM: Populus trichocarpa
<220> FEATURE:
<221> NAME/KEY: MISC_FEATURE
<222> LOCATION: (1)..(274)
```

<223> OTHER INFORMATION: ABC Transporter

<400> SEQUENCE: 49

Met Gln Phe Ala Tyr Ala Gly Gln His Pro Leu Phe Tyr Asp Phe Asn
1               5                   10                  15

Leu Asn Ile Ser Pro Gly Ser Arg Cys Leu Leu Val Gly Ala Asn Gly
            20                  25                  30

Ser Gly Lys Thr Thr Leu Leu Lys Ile Met Ala Gly Lys His Met Val
        35                  40                  45

Gly Gly Lys Asp Val Val Arg Val Ile Asn Gly Ser Ala Phe His Asp
    50                  55                  60

Thr Gln Leu Val Cys Ser Gly Asp Leu Ala Tyr Leu Gly Gly Ser Trp
65                  70                  75                  80

Ser Lys Thr Val Gly Ser Ala Gly Glu Ile Pro Leu Gln Gly Asp Phe
                85                  90                  95

Ser Ala Glu His Met Ile Phe Gly Val Glu Gly Thr Asp Pro Val Arg
            100                 105                 110

Arg Glu Lys Leu Ile Asp Leu Asp Ile Asp Leu Gln Trp Arg Met
        115                 120                 125

His Lys Val Ser Asp Gly Gln Arg Arg Val Gln Ile Cys Met Gly
    130                 135                 140

Leu Leu His Pro Phe Lys Val Leu Leu Asp Glu Val Thr Val Asp
145                 150                 155                 160

Leu Asp Val Val Ala Arg Met Asp Leu Leu Glu Phe Phe Lys Glu Glu
                165                 170                 175

Cys Asp Gln Arg Gly Ala Thr Ile Val Tyr Ala Thr His Ile Phe Asp
            180                 185                 190

Gly Leu Glu Thr Trp Ala Thr His Leu Ala Tyr Ile Gln Asp Gly Glu
        195                 200                 205

Leu Arg Arg Ala Glu Lys Leu Thr Glu Val His Glu Leu Lys Ser Ser
    210                 215                 220

Ala Asn Leu Leu Ser Val Val Glu Ser Trp Leu Arg His Glu Thr Lys
225                 230                 235                 240

Ser Glu Lys Lys Lys Pro Thr Asn Pro Pro Ala Gln Asn Gln Lys Thr
                245                 250                 255

Ser Pro Leu Gly Ser Ser Pro Phe Met Ser Ser Arg His Met Ala Tyr
            260                 265                 270

Tyr Arg

<210> SEQ ID NO 50
<211> LENGTH: 287
<212> TYPE: PRT
<213> ORGANISM: Pyrus x bretschneideri
<220> FEATURE:
<221> NAME/KEY: MISC_FEATURE
<222> LOCATION: (1)..(287)
<223> OTHER INFORMATION: ABC Transporter

<400> SEQUENCE: 50

Met Ala Glu Glu Ala Ser Ser Gly Ile Arg Val Gln Gly Met Gln Phe
1               5                   10                  15

Ala Tyr Asp Ala Gln Pro Pro Leu Phe Cys Asp Phe Asn Leu Glu Ile
            20                  25                  30

Thr Pro Gly Ser Arg Cys Leu Leu Ile Gly Ala Asn Gly Ser Gly Lys
        35                  40                  45

Thr Thr Leu Leu Lys Ile Leu Ala Gly Lys Gln Met Val Gly Gly Arg

```
                50                  55                  60
Asp Val Val Arg Val Leu Asn Cys Ser Ala Phe His Asp Thr His Leu
 65                  70                  75                  80

Val Cys Ser Gly Asp Leu Ala Tyr Leu Gly Gly Ser Trp Thr Lys Thr
                 85                  90                  95

Val Gly Ser Ala Gly Glu Leu Pro Leu Gln Gly Asp Phe Ser Ala Glu
                100                 105                 110

His Met Ile Phe Gly Val Glu Gly Thr Asp Pro Val Arg Arg Asp Lys
                115                 120                 125

Leu Ile Glu Leu Leu Asp Ile Asp Leu Arg Trp Arg Met His Lys Val
            130                 135                 140

Ser Asp Gly Gln Arg Arg Val Gln Ile Cys Met Gly Leu Leu His
145                 150                 155                 160

Pro Phe Lys Val Leu Leu Leu Asp Glu Val Thr Val Asp Leu Asp Val
                165                 170                 175

Val Ala Arg Met Asp Leu Leu Asp Phe Phe Lys Glu Glu Cys Glu Gln
                180                 185                 190

Arg Gly Ala Thr Ile Val Tyr Ala Thr His Ile Phe Asp Gly Leu Glu
                195                 200                 205

Thr Trp Ala Thr His Leu Ala Tyr Ile Gln Asp Gly Glu Leu Lys Arg
            210                 215                 220

Ala Glu Lys Leu Ser Glu Val Asn Glu Leu Lys Ser Ser Val Asn Leu
225                 230                 235                 240

Leu Ser Val Val Glu Ser Trp Leu Arg Ala Glu Thr Lys Ser Asp Lys
                245                 250                 255

Lys Lys Ser Ser Asn Pro Pro Ala Gln Met Lys Lys Ala Ser Pro Phe
                260                 265                 270

Ala Ser Ser Pro Phe Thr Ser Ser Arg His Met Ala Tyr Tyr Arg
            275                 280                 285

<210> SEQ ID NO 51
<211> LENGTH: 286
<212> TYPE: PRT
<213> ORGANISM: Cynara cardunculus
<220> FEATURE:
<221> NAME/KEY: MISC_FEATURE
<222> LOCATION: (1)..(286)
<223> OTHER INFORMATION: ABC Transporter

<400> SEQUENCE: 51

Met Glu Val Glu Ser Ser Ile Lys Val Asn Gly Met Gln Phe Gly
 1               5                  10                  15

Tyr Ser Gly Glu Asn Pro Ile Phe Val Asp Phe Asn Leu Lys Ile Ser
                 20                  25                  30

Pro Arg Ser Arg Cys Leu Leu Val Gly Ala Asn Gly Ser Gly Lys Thr
             35                  40                  45

Thr Leu Leu Lys Ile Leu Ala Gly Lys His Met Val Gly Gly Arg Asn
         50                  55                  60

Val Val Arg Val Leu Asp Phe Ser Ser Phe His Asp Thr His Leu Val
 65                  70                  75                  80

Cys Ser Gly Asp Leu Ser Tyr Leu Gly Gly Ser Trp Thr Lys Thr Ile
                 85                  90                  95

Gly Ser Ala Gly Glu Val Pro Leu Gln Gly Asp Phe Ser Ala Glu His
                100                 105                 110

Met Ile Phe Gly Val Glu Gly Ile Asp Pro Val Arg Arg Glu Lys Leu
            115                 120                 125
```

```
Ile Asp Leu Leu Asp Ile Asp Leu Gln Trp Arg Met His Lys Val Ser
    130                 135                 140

Asp Gly Gln Arg Arg Arg Val Gln Ile Cys Leu Gly Leu Leu His Pro
145                 150                 155                 160

Phe Gln Val Leu Leu Asp Glu Val Thr Val Asp Leu Asp Val Val
                165                 170                 175

Ala Arg Met Asp Leu Leu Glu Phe Phe Lys Glu Glu Cys Glu Gln Arg
            180                 185                 190

Gly Ala Thr Ile Val Tyr Ala Thr His Ile Phe Asp Gly Leu Glu Ser
            195                 200                 205

Trp Ala Thr Asp Leu Ala Tyr Ile Gln Asp Gly Glu Leu Lys Arg Tyr
    210                 215                 220

Glu Lys Leu Ala Asp Leu Pro Glu Met Lys Asn Ser Ser Asn Leu Leu
225                 230                 235                 240

Ser Val Val Glu Ser Trp Leu Arg Ala Glu Thr Lys Asn Pro Lys Lys
                245                 250                 255

Lys Pro Val Asn Pro Ser Pro Leu Ile Pro Lys Thr Ser Pro Phe Asp
            260                 265                 270

Ser Ser Pro Phe Arg Ser Ser Arg His Met Ala Tyr Tyr Arg
            275                 280                 285

<210> SEQ ID NO 52
<211> LENGTH: 286
<212> TYPE: PRT
<213> ORGANISM: Sesamum indicum
<220> FEATURE:
<221> NAME/KEY: MISC_FEATURE
<222> LOCATION: (1)..(286)
<223> OTHER INFORMATION: ABC Transporter

<400> SEQUENCE: 52

Met Gly Glu Glu Ser His Ser Ile Gln Val Ser Gly Met Gln Phe Ser
1               5                   10                  15

Tyr Asp Ala Asn Ser Pro Leu Phe Phe Asp Phe Ser Leu Asn Ile Tyr
            20                  25                  30

Pro Gly Ser Arg Cys Leu Leu Val Gly Ala Asn Gly Ser Gly Lys Thr
        35                  40                  45

Thr Leu Leu Arg Ile Leu Ala Gly Lys His Met Val Gly Gly Arg Asp
    50                  55                  60

Val Val Arg Val Leu Asn Cys Ser Ala Phe His Asp Thr Ser Leu Val
65                  70                  75                  80

Cys Ser Gly Asp Leu Ala Tyr Leu Gly Glu Ser Trp Ser Lys Thr Val
                85                  90                  95

Gly Ser Ala Gly Glu Leu Pro Leu Gln Gly Asp Phe Ser Ala Glu His
            100                 105                 110

Met Ile Phe Gly Val Glu Gly Val Asp Pro Val Arg Arg Asp Lys Leu
            115                 120                 125

Ile Glu Leu Leu Asp Ile Asp Leu His Trp Arg Met His Lys Val Ser
    130                 135                 140

Asp Gly Gln Arg Arg Arg Val Gln Ile Cys Met Gly Leu Leu His Pro
145                 150                 155                 160

Tyr Lys Val Leu Leu Leu Asp Glu Val Thr Val Asp Leu Asp Val Val
                165                 170                 175

Ala Arg Met Asp Leu Leu Glu Phe Phe Lys Glu Glu Cys Glu Gln Arg
            180                 185                 190
```

```
Arg Ala Thr Ile Val Tyr Ala Thr His Ile Phe Asp Gly Leu Glu Thr
            195                 200                 205

Trp Ala Thr Asp Leu Val Tyr Val Gln Glu Gly Val Leu Lys Arg Ser
    210                 215                 220

Asp Lys Leu Ala Asp Leu Lys Glu Leu Lys Asn Asn Met Asn Leu Leu
225                 230                 235                 240

Ser Val Val Glu Ser Trp Leu Arg Thr Glu Thr Lys Ile Glu Lys Lys
                245                 250                 255

Lys Pro Val Asn Ser Pro Ser Pro Leu Gln Lys Ser Ser Pro Phe Asp
                260                 265                 270

Asn Ser Pro Phe Arg Ser Ser Arg His Met Ala Tyr Tyr Arg
            275                 280                 285

<210> SEQ ID NO 53
<211> LENGTH: 300
<212> TYPE: PRT
<213> ORGANISM: Gossypium hirsutum
<220> FEATURE:
<221> NAME/KEY: MISC_FEATURE
<222> LOCATION: (1)..(300)
<223> OTHER INFORMATION: ABC Transporter

<400> SEQUENCE: 53

Met Ala Glu Gln Ala Cys Cys Arg Ser Gly Glu Gly Lys Glu Asn Gly
1               5                   10                  15

Gly Asp Ser Gln Gly Ile Thr Val Cys Asp Met Gln Phe Ala Tyr Glu
            20                  25                  30

Leu Gln His Pro Leu Phe Phe Asp Phe Asn Leu Asp Ile Ala Arg Gly
        35                  40                  45

Ser Arg Cys Leu Leu Val Gly Ala Asn Gly Ser Gly Lys Thr Thr Leu
    50                  55                  60

Leu Lys Ile Leu Ala Gly Lys His Met Val Gly Gly Arg Glu Val Val
65              70                  75                  80

Arg Val Leu Asn Arg Ser Ala Phe His Asp Thr Gln Leu Val Cys Gly
                85                  90                  95

Gly Asp Leu Ala Tyr Leu Gly Gly Ser Trp Ser Lys Thr Ile Gly Ser
            100                 105                 110

Ala Gly Glu Val Pro Leu Gln Gly Asp Phe Ser Ala Glu His Met Ile
        115                 120                 125

Phe Gly Val Glu Gly Ile Asp Pro Val Arg Arg Asp Lys Leu Ile Glu
    130                 135                 140

Leu Leu Asp Ile Asp Leu Gln Trp Arg Met His Lys Val Ser Asp Gly
145                 150                 155                 160

Gln Arg Arg Arg Val Gln Ile Cys Met Gly Leu Leu Gln Pro Phe Gln
                165                 170                 175

Val Leu Leu Leu Asp Glu Val Thr Val Asp Leu Asp Val Val Ala Arg
            180                 185                 190

Met Asp Leu Leu Asp Phe Phe Lys Glu Glu Cys Glu Gln Arg Gly Ala
        195                 200                 205

Thr Val Val Tyr Ala Thr His Ile Phe Asp Gly Leu Glu Thr Trp Ala
    210                 215                 220

Thr His Leu Ala Tyr Ile Gln Asp Gly Gln Leu Lys Arg Ser Ala Lys
225                 230                 235                 240

Leu Thr Glu Ile Asn Glu Leu Lys Ser Ser Glu Asn Leu Leu Ser Val
                245                 250                 255

Val Glu Ala Trp Leu Arg Ser Glu Thr Lys Cys Glu Lys Lys Lys Pro
```

```
                260                 265                 270
Ser Asn Ser Pro Ala Gln Val Gln Lys Ser Ser Pro Phe Gly Thr Ser
            275                 280                 285

Pro Phe Met Ser Ser Arg His Met Ala Tyr Tyr Arg
        290                 295                 300

<210> SEQ ID NO 54
<211> LENGTH: 292
<212> TYPE: PRT
<213> ORGANISM: Beta vulgaris
<220> FEATURE:
<221> NAME/KEY: MISC_FEATURE
<222> LOCATION: (1)..(292)
<223> OTHER INFORMATION: ABC Transporter

<400> SEQUENCE: 54

Met Val Gln Glu Met Lys Asn Val Glu Ser Ser Thr Ser Ile Lys Val
1               5                   10                  15

Gln Ala Met Gln Phe Ala Tyr Pro Gly Gln Pro Pro Ile Phe Ala Asp
            20                  25                  30

Phe Ser Leu Asp Ile Ser Ala Gly Ser Arg Cys Leu Leu Val Gly Ala
        35                  40                  45

Asn Gly Ser Gly Lys Thr Thr Leu Leu Lys Ile Leu Ala Gly Lys His
    50                  55                  60

Met Val Gly Gly Arg Asp Val Val Gln Val Leu Asn Ser Ser Ala Phe
65                  70                  75                  80

His Asp Thr Arg Leu Val Cys Ser Gly Asp Leu Ala Tyr Leu Gly Gly
                85                  90                  95

Ser Trp Ser Lys Thr Ile Gly Ser Ala Gly Glu Val Pro Leu Gln Gly
            100                 105                 110

Asp Phe Ser Ala Glu Gln Met Ile Phe Gly Val Glu Gly Ser Asp Pro
        115                 120                 125

Asp Arg Arg Ala Lys Leu Ile Glu Leu Leu Asp Ile Asp Leu Gln Trp
    130                 135                 140

Arg Met His Lys Val Ser Asp Gly Gln Arg Arg Val Gln Ile Cys
145                 150                 155                 160

Met Gly Leu Leu His Pro Phe Lys Ile Leu Leu Leu Asp Glu Val Thr
                165                 170                 175

Val Asp Leu Asp Val Val Ala Arg Met Asp Leu Leu Glu Phe Leu Lys
            180                 185                 190

Glu Glu Cys Asp Gln Arg Gly Ala Thr Ile Val Tyr Ala Thr His Ile
        195                 200                 205

Phe Asp Gly Leu Glu Thr Trp Ala Thr His Leu Ala Tyr Ile Gln Glu
    210                 215                 220

Gly Asp Leu Arg Lys Ile Glu Lys Leu Ser Glu Leu His Glu Leu Lys
225                 230                 235                 240

Thr Ser Asn Asn Leu Leu Ser Val Val Glu Ser Trp Leu Arg Ser Glu
                245                 250                 255

Thr Lys Ile Glu Lys Lys Pro Ala Thr Thr Ala Thr Gln Asn Gln
            260                 265                 270

Lys Ser Ser Gly Phe Asp Ala Ser Pro Phe Arg Ser Ser Arg His Met
        275                 280                 285

Ala Tyr Tyr Arg
    290

<210> SEQ ID NO 55
```

```
<211> LENGTH: 294
<212> TYPE: PRT
<213> ORGANISM: Citrus sinensis
<220> FEATURE:
<221> NAME/KEY: MISC_FEATURE
<222> LOCATION: (1)..(294)
<223> OTHER INFORMATION: ABC Transporter

<400> SEQUENCE: 55
```

Met Ala Asp Gly Met Asn Glu Asn Glu Lys Leu Asn Ser Ile Lys Val
1               5                   10                  15

Cys Gly Met Gln Phe Ser Tyr Glu Gly Asn Asp Lys Pro Pro Leu Phe
            20                  25                  30

Tyr Asp Phe Asn Leu Gly Ile Ser Pro Gly Ser Arg Cys Leu Leu Val
        35                  40                  45

Gly Ala Asn Gly Ser Gly Lys Thr Thr Leu Leu Lys Ile Leu Ala Gly
    50                  55                  60

Lys His Met Val Gly Gly Arg Asp Val Val Gln Val Leu Asn Arg Ser
65                  70                  75                  80

Ser Phe His Asp Thr Gln Leu Val Cys Ser Gly Asp Leu Ser Tyr Leu
                85                  90                  95

Gly Gly Ser Trp Ser Lys Thr Val Gly Ser Ala Gly Glu Ile Pro Leu
            100                 105                 110

Gln Gly Asp Phe Ser Ala Glu His Met Ile Phe Gly Val Glu Gly Ser
        115                 120                 125

Asp Pro Val Arg Arg Glu Arg Leu Ile Glu Leu Leu Asp Ile Asp Leu
    130                 135                 140

Gln Trp Arg Met His Lys Val Ser Asp Gly Gln Arg Arg Arg Val Gln
145                 150                 155                 160

Ile Cys Met Gly Leu Leu His Pro Phe Lys Val Leu Leu Leu Asp Glu
                165                 170                 175

Ile Thr Val Asp Leu Asp Val Val Ala Arg Met Asp Leu Leu Asp Phe
            180                 185                 190

Phe Lys Asp Glu Cys Glu Gln Arg Gly Ala Thr Ile Val Tyr Ala Thr
        195                 200                 205

His Ile Phe Asp Gly Leu Glu Thr Trp Ala Thr His Leu Ala Tyr Ile
    210                 215                 220

Gln Asp Gly Glu Leu Arg Arg Ala Glu Lys Leu Ala Glu Leu Asp Glu
225                 230                 235                 240

Leu Arg Asn Ser Thr Asn Leu Leu Ser Val Val Glu Ser Trp Leu Arg
                245                 250                 255

Ser Glu Thr Lys Leu Glu Lys Lys Arg Pro Val Asp Pro Pro Lys Gln
            260                 265                 270

Val Gln Lys Thr Ser Pro Phe Gly Ser Ser Pro Phe Met Ser Ser Arg
        275                 280                 285

His Met Ala Tyr Asn Arg
    290

```
<210> SEQ ID NO 56
<211> LENGTH: 295
<212> TYPE: PRT
<213> ORGANISM: Amborella trichopoda
<220> FEATURE:
<221> NAME/KEY: MISC_FEATURE
<222> LOCATION: (1)..(295)
<223> OTHER INFORMATION: ABC Transporter

<400> SEQUENCE: 56
```

Met Gly Phe Glu Lys Glu Ala Leu Gln Phe Gln Leu Thr Asn Ser Ile
1               5                   10                  15

Glu Val Ser Ala Leu Gln Phe Ser Tyr Asp Asp Gln Pro Pro Leu Phe
            20                  25                  30

Ser Asn Phe Asn Leu His Ile Ser Pro Gly Ser Arg Cys Leu Leu Ile
            35                  40                  45

Gly Ala Asn Gly Ser Gly Lys Thr Thr Leu Leu Arg Ile Leu Ala Gly
    50                  55                  60

Lys His Met Val Gly Arg Asp Val Val Val Ile Gly His Ser
65                  70                  75                  80

Ala Phe His Asp Thr Gln Leu Val Cys Ser Gly Glu Leu Ala Tyr Leu
                85                  90                  95

Gly Gly Ser Trp Ser Lys Thr Val Gly Ser Ala Gly Glu Ile Pro Leu
            100                 105                 110

Gln Gly Asp Phe Ser Ala Glu His Met Ile Phe Gly Val Glu Gly Val
            115                 120                 125

Asp Pro Glu Arg Arg Glu Lys Leu Ile Asp Leu Leu Asp Ile Asp Leu
    130                 135                 140

Gln Trp Arg Met His Lys Val Ser Asp Gly Gln Arg Arg Val Gln
145                 150                 155                 160

Ile Cys Met Gly Leu Leu His Pro Phe Gln Val Leu Leu Asp Glu
                165                 170                 175

Val Thr Val Asp Leu Asp Val Val Ala Arg Met Asp Leu Leu Asp Phe
                180                 185                 190

Phe Lys Glu Glu Cys Gly Gly Arg Gly Ala Thr Ile Val Tyr Ala Thr
            195                 200                 205

His Ile Phe Asp Gly Leu Glu Ser Trp Ala Thr His Val Ala Tyr Ile
    210                 215                 220

Gln Asp Gly Glu Leu Arg Arg Ser Glu Lys Leu Ala Asp Val Asn Glu
225                 230                 235                 240

Met Lys Ser Ala Lys Asn Leu Tyr Ser Val Val Glu Ser Trp Leu Arg
                245                 250                 255

Ser Glu Thr Lys Thr Met Thr Lys Lys Ala Phe Asn Pro Ala Ser His
                260                 265                 270

Val Arg Arg Val Pro Thr Val Asn Asp Ala Ser Pro Phe Arg Ser Ser
            275                 280                 285

Arg His Met Ala Tyr Tyr Arg
    290                 295

<210> SEQ ID NO 57
<211> LENGTH: 301
<212> TYPE: PRT
<213> ORGANISM: Gossypium raimondii
<220> FEATURE:
<221> NAME/KEY: MISC_FEATURE
<222> LOCATION: (1)..(301)
<223> OTHER INFORMATION: ABC Transporter

<400> SEQUENCE: 57

Met Ala Glu Gln Ala Cys Cys Arg Ser Gly Glu Gly Lys Glu Asn Gly
1               5                   10                  15

Gly Asp Ser Gln Gly Ile Thr Val Cys Gly Met Gln Phe Ala Tyr Glu
            20                  25                  30

Leu Gln His Pro Leu Phe Phe Asp Phe Asn Leu Asp Ile Ala Arg Gly
            35                  40                  45

Ser Arg Cys Leu Leu Val Gly Ala Asn Gly Ser Ala Gly Lys Thr Thr

```
            50                  55                  60
Leu Leu Lys Ile Leu Ala Gly Lys His Met Val Gly Gly Arg Glu Val
 65                  70                  75                  80

Val Arg Val Leu Asn Arg Ser Ala Phe His Asp Thr Gln Leu Val Cys
                 85                  90                  95

Gly Gly Asp Leu Ala Tyr Leu Gly Gly Ser Trp Ser Lys Thr Ile Gly
                100                 105                 110

Ser Ala Gly Glu Val Pro Leu Gln Gly Asp Phe Ser Ala Glu His Met
            115                 120                 125

Ile Phe Gly Val Glu Gly Ile Asp Pro Val Arg Arg Asp Lys Leu Ile
130                 135                 140

Glu Leu Leu Asp Ile Asp Leu Gln Trp Arg Met His Lys Val Ser Asp
145                 150                 155                 160

Gly Gln Arg Arg Val Gln Ile Cys Met Gly Leu Leu His Pro Phe
                165                 170                 175

Gln Val Leu Leu Leu Asp Glu Val Thr Val Asp Leu Asp Val Val Ala
            180                 185                 190

Arg Met Asp Leu Leu Asp Phe Phe Lys Glu Glu Cys Glu Gln Arg Gly
            195                 200                 205

Ala Thr Val Val Tyr Ala Thr His Ile Phe Asp Gly Leu Glu Thr Trp
            210                 215                 220

Ala Thr His Leu Ala Tyr Ile Gln Asp Gly Gln Leu Lys Arg Ser Glu
225                 230                 235                 240

Lys Leu Thr Glu Ile Asn Glu Leu Lys Ser Ser Glu Asn Leu Leu Ser
                245                 250                 255

Val Val Glu Ala Trp Leu Arg Ser Glu Thr Lys Cys Glu Lys Lys Lys
            260                 265                 270

Pro Ser Asn Ser Pro Ala Gln Val Gln Lys Ser Ser Pro Phe Gly Thr
            275                 280                 285

Ser Pro Phe Met Ser Ser Arg His Met Ala Tyr Tyr Arg
            290                 295                 300

<210> SEQ ID NO 58
<211> LENGTH: 300
<212> TYPE: PRT
<213> ORGANISM: Juglans regia
<220> FEATURE:
<221> NAME/KEY: MISC_FEATURE
<222> LOCATION: (1)..(300)
<223> OTHER INFORMATION: ABC Transporter

<400> SEQUENCE: 58

Met Ala Asp Lys Glu Thr Ser Lys Pro Ile Val Glu Glu Val Glu Ser
 1               5                  10                  15

Glu Asp Leu Asn Ser Ile Arg Val Cys Gly Met Gln Phe Ala Tyr Glu
                20                  25                  30

Gly Glu Pro Pro Leu Phe Ala Asp Phe Asn Leu Lys Ile Pro Pro Gly
            35                  40                  45

Ser Arg Cys Leu Leu Val Gly Ala Asn Gly Ser Gly Lys Thr Thr Leu
 50                  55                  60

Leu Lys Ile Leu Ala Gly Lys His Met Val Gly Gly Arg Asp Val Val
 65                  70                  75                  80

Arg Val Leu Asn Asn Ser Ala Phe His Asp Thr Lys Leu Val Cys Ser
                 85                  90                  95

Gly Asp Leu Ala Tyr Leu Gly Gly Ser Trp Ser Lys Thr Val Gly Ser
                100                 105                 110
```

```
Ala Gly Glu Ile Pro Leu Gln Gly Asp Phe Ser Ala Glu His Met Ile
            115                 120                 125

Phe Gly Val Glu Gly Val Asp Pro Asp Arg Arg Leu Asn Leu Ile Glu
            130                 135                 140

Leu Leu Asp Ile Asp Leu Gln Trp Arg Met His Lys Val Ser Asp Gly
145                 150                 155                 160

Gln Arg Arg Arg Val Gln Ile Cys Met Gly Leu Leu His Pro Phe Lys
                165                 170                 175

Val Leu Leu Leu Asp Glu Val Thr Val Asp Leu Asp Val Val Ala Arg
                180                 185                 190

Leu Asp Leu Leu Asp Phe Phe Lys Glu Glu Cys Asp Gln Arg Gly Ala
                195                 200                 205

Thr Ile Val Tyr Ala Thr His Ile Phe Asp Gly Leu Glu Thr Trp Ala
            210                 215                 220

Thr His Leu Ala Tyr Ile Gln Asp Gly Glu Leu Arg Arg Val Gln Lys
225                 230                 235                 240

Leu Ser Glu Val Asn Glu Leu Lys Asn Ser Ala Asn Leu Leu Ser Val
                245                 250                 255

Val Glu Ser Trp Leu Arg Ala Glu Thr Lys Arg Glu Lys Lys Lys Pro
                260                 265                 270

Thr Asn Pro Pro Ala Gln Ile Gln Lys Thr Ser Pro Phe Gly Ser Ser
            275                 280                 285

Pro Phe Met Ser Ser Arg His Met Ala Tyr Phe Arg
            290                 295                 300

<210> SEQ ID NO 59
<211> LENGTH: 274
<212> TYPE: PRT
<213> ORGANISM: Populus trichocarpa
<220> FEATURE:
<221> NAME/KEY: MISC_FEATURE
<222> LOCATION: (1)..(274)
<223> OTHER INFORMATION: ABC Transporter

<400> SEQUENCE: 59

Met Gln Phe Ala Tyr Pro Gly Gln His Pro Leu Phe Tyr Glu Phe Asn
1               5                   10                  15

Leu Asn Ile Ser Pro Gly Ser Arg Cys Leu Leu Val Gly Ala Asn Gly
            20                  25                  30

Ser Gly Lys Thr Thr Leu Leu Lys Ile Met Ala Gly Lys His Met Val
        35                  40                  45

Gly Gly Arg Asp Val Val Arg Val Ile Asn Gly Ser Ala Phe His Asp
    50                  55                  60

Thr Gln Leu Val Cys Ser Gly Asp Leu Ala Tyr Leu Gly Gly Ser Trp
65                  70                  75                  80

Ser Lys Thr Val Gly Ser Ala Gly Glu Ile Pro Leu Gln Gly Asp Phe
                85                  90                  95

Ser Ala Glu His Met Ile Phe Gly Val Glu Gly Thr Asp Pro Val Arg
            100                 105                 110

Arg Glu Lys Leu Ile Glu Leu Leu Asp Ile Asp Leu Lys Trp Arg Met
            115                 120                 125

His Lys Val Ser Asp Gly Gln Arg Arg Arg Val Gln Ile Cys Met Gly
        130                 135                 140

Leu Leu His Pro Phe Lys Val Leu Leu Leu Asp Glu Val Thr Val Asp
145                 150                 155                 160
```

```
Leu Asp Val Val Ala Arg Met Asp Leu Leu Glu Phe Phe Lys Glu Glu
            165                 170                 175

Cys Asp Gln Arg Gly Ala Thr Ile Val Tyr Ala Thr His Ile Phe Asp
        180                 185                 190

Gly Leu Glu Thr Trp Ala Thr His Leu Ala Tyr Ile Gln Asp Gly Glu
        195                 200                 205

Leu Lys Arg Val Lys Lys Leu Thr Glu Val His Glu Leu Lys Asn Ser
210                 215                 220

Ala Thr Leu Leu Ser Val Val Glu Ser Trp Leu Arg Ser Glu Thr Lys
225                 230                 235                 240

Asn Glu Lys Lys Lys Pro Thr Asn Pro Pro Ala Gln Asn Gln Lys Thr
                245                 250                 255

Ser Pro Phe Gly Ser Ser Pro Phe Met Ser Ser Arg His Met Ala Tyr
            260                 265                 270

Tyr Arg

<210> SEQ ID NO 60
<211> LENGTH: 299
<212> TYPE: PRT
<213> ORGANISM: Medicago truncatula
<220> FEATURE:
<221> NAME/KEY: MISC_FEATURE
<222> LOCATION: (1)..(299)
<223> OTHER INFORMATION: ABC Transporter

<400> SEQUENCE: 60

Met Ala Ile Glu Gln Lys Gln Gln Glu Asn Glu Asp Ser Ser Asn Gly
1               5                   10                  15

Ile Arg Val Gln Gly Met Gln Phe Ser Tyr Asn Asp Ile Gln Gln Gln
            20                  25                  30

Gln Pro Pro Leu Phe Val Asp Phe Asn Leu Gln Val Ser Pro Gly Ser
        35                  40                  45

Arg Cys Leu Leu Val Gly Ala Asn Gly Ser Gly Lys Thr Thr Leu Leu
    50                  55                  60

Lys Ile Leu Ala Gly Lys His Met Val Gly Gly Lys Asp Val Val Arg
65                  70                  75                  80

Val Leu Asn Cys Ser Ala Phe His Asp Thr Gln Leu Val Cys Ser Gly
                85                  90                  95

Asp Leu Ala Tyr Leu Gly Gly Ser Trp Ser Lys Asn Val Gly Cys Ala
            100                 105                 110

Gly Asp Ile Pro Leu Gln Gly Asp Phe Ser Ala Glu His Met Ile Phe
        115                 120                 125

Gly Val Glu Gly Val Asp Pro Glu Arg Arg Asp Lys Leu Ile Glu Leu
    130                 135                 140

Leu Asp Ile Asp Leu Gln Trp Arg Met His Lys Val Ser Asp Gly Gln
145                 150                 155                 160

Arg Arg Arg Val Gln Ile Cys Leu Gly Leu Leu His Pro Tyr Lys Val
                165                 170                 175

Leu Leu Leu Asp Glu Val Thr Val Asp Leu Asp Val Val Thr Arg Met
            180                 185                 190

Asp Leu Leu Glu Phe Phe Lys Glu Glu Cys Glu Gln Arg Glu Ala Thr
        195                 200                 205

Val Val Tyr Ala Thr His Ile Phe Asp Gly Leu Glu Thr Trp Ala Thr
    210                 215                 220

His Leu Ala Tyr Ile Gln Glu Gly Glu Leu Arg Arg Ala Glu Lys Ile
225                 230                 235                 240
```

-continued

```
Ser Asp Val Asn Glu Leu Lys Ser Ser Ile Asn Leu Ser Val Val
            245                 250                 255

Glu Ser Trp Leu Arg Ala Glu Thr Lys Leu Glu Lys Lys Pro Val
        260                 265                 270

Gln Asn Thr Ser His Ala Gln Gly Asn Ser Phe Thr Asn Ser Pro Phe
        275                 280                 285

Ser Ser Ser Ser Arg His Met Ala Tyr Tyr Arg
        290                 295
```

<210> SEQ ID NO 61
<211> LENGTH: 294
<212> TYPE: PRT
<213> ORGANISM: Spinacia oleracea
<220> FEATURE:
<221> NAME/KEY: MISC_FEATURE
<222> LOCATION: (1)..(294)
<223> OTHER INFORMATION: ABC Transporter

<400> SEQUENCE: 61

```
Met Val Gln Glu Asn Gly Asn Val Ser Gly Asn Ser Ser Ser Ile
1               5                  10                  15

Lys Val Gln Ala Met Gln Phe Ala Tyr Pro Gly Gln Pro Ile Phe
            20                  25                  30

Val Asp Phe Ser Leu Gln Ile Ala Pro Gly Ser Arg Cys Leu Leu Val
        35                  40                  45

Gly Ala Asn Gly Ser Gly Lys Thr Thr Leu Leu Lys Ile Leu Ala Gly
    50                  55                  60

Lys His Met Val Gly Gly Arg Asp Val Val Gln Val Leu Asn Ser Ser
65                  70                  75                  80

Ala Phe His Asp Thr His Leu Val Cys Gly Gly Asp Leu Ala Tyr Leu
                85                  90                  95

Gly Gly Ser Trp Ser Lys Thr Ile Gly Cys Ala Gly Asp Val Pro Leu
            100                 105                 110

Gln Gly Asp Ile Ser Ala Glu Gln Met Leu Phe Gly Val Glu Gly Thr
        115                 120                 125

Asp Pro Asp Arg Arg Asp Lys Leu Ile Glu Leu Asp Ile Asp Leu
        130                 135                 140

Gln Trp Arg Met His Lys Val Ser Asp Gly Gln Arg Arg Val Gln
145                 150                 155                 160

Ile Cys Met Gly Leu Leu His Pro Phe Lys Val Leu Leu Asp Glu
                165                 170                 175

Val Thr Val Asp Leu Asp Val Val Ala Arg Met Asp Leu Leu Glu Phe
            180                 185                 190

Leu Lys Glu Glu Cys Asp Gln Arg Gly Ala Thr Ile Val Tyr Ala Thr
        195                 200                 205

His Ile Phe Asp Gly Leu Glu Thr Trp Ala Thr His Leu Ala Tyr Ile
    210                 215                 220

Gln Glu Gly Glu Leu Arg Lys Val Glu Lys Met Ser Glu Leu His Glu
225                 230                 235                 240

Leu Lys Asn Ser Thr Asn Leu Leu Ser Val Val Glu Ala Trp Leu Arg
                245                 250                 255

Ser Glu Thr Lys Leu Glu Lys Lys Pro Val Ala Thr Ile Thr Asn
            260                 265                 270

Asn Gln Lys Ser Ser Gly Phe Asp Ala Ser Pro Phe Arg Ser Ser Arg
        275                 280                 285
```

His Met Ala Tyr Tyr Arg
    290

<210> SEQ ID NO 62
<211> LENGTH: 296
<212> TYPE: PRT
<213> ORGANISM: Glycine max
<220> FEATURE:
<221> NAME/KEY: MISC_FEATURE
<222> LOCATION: (1)..(296)
<223> OTHER INFORMATION: ABC Transporter

<400> SEQUENCE: 62

Met Asn Ser Ser Leu Ser Gly Asn Gly Ser Thr Thr Met Ala Ala
1               5                   10                  15

Glu Asn Glu Asp Ser Cys Gly Ile Arg Val Thr Gly Met Gln Phe Ser
            20                  25                  30

Tyr Asp Val Gln Gln Pro Pro Leu Phe Leu Asp Phe Asn Leu Asn Val
        35                  40                  45

Ser Pro Gly Ser Arg Cys Leu Leu Val Gly Ala Asn Gly Ser Gly Lys
    50                  55                  60

Thr Thr Leu Leu Lys Ile Leu Ala Gly Lys His Met Val Gly Gly Arg
65                  70                  75                  80

Asp Val Val Arg Val Leu Ser Gly Ser Ala Phe His Asp Thr Gln Leu
                85                  90                  95

Val Cys Ser Gly Asp Leu Ala Tyr Leu Gly Gly Ser Trp Ser Lys Asn
            100                 105                 110

Val Gly Ser Ala Gly Glu Ile Pro Leu Gln Gly Asp Phe Ser Ala Glu
        115                 120                 125

His Met Ile Phe Gly Val Glu Gly Ala Asp Pro Glu Arg Arg Asp Lys
    130                 135                 140

Leu Ile Glu Leu Leu Asp Ile Asp Leu Gln Trp Arg Met His Lys Val
145                 150                 155                 160

Ser Asp Gly Gln Arg Arg Arg Val Gln Ile Cys Leu Gly Leu Leu His
                165                 170                 175

Pro Tyr Lys Val Leu Leu Leu Asp Glu Val Thr Val Asp Leu Asp Val
            180                 185                 190

Val Thr Arg Met Asp Leu Leu Asp Phe Phe Lys Glu Glu Cys Glu Gln
        195                 200                 205

Arg Glu Ala Ile Ile Val Tyr Ala Thr His Ile Phe Asp Gly Leu Glu
    210                 215                 220

Thr Trp Ala Thr His Leu Ala Tyr Ile Gln Asp Gly Glu Leu Arg Arg
225                 230                 235                 240

Ala Glu Lys Ile Ser Asn Val Lys Glu Leu Lys Ser Ser Thr Asn Leu
                245                 250                 255

Leu Ser Val Val Glu Ala Trp Leu Arg Ala Glu Thr Lys Leu Glu Lys
            260                 265                 270

Lys Asn Pro Val Gln Lys Thr Ser Val Ala Ser Ser Pro Phe Phe Ser
        275                 280                 285

Ser Arg His Met Ala Tyr Tyr Arg
    290                 295

<210> SEQ ID NO 63
<211> LENGTH: 287
<212> TYPE: PRT
<213> ORGANISM: Malus domestica
<220> FEATURE:
<221> NAME/KEY: MISC_FEATURE
<222> LOCATION: (1)..(287)
<223> OTHER INFORMATION: ABC Transporter
<220> FEATURE:
<221> NAME/KEY: MISC_FEATURE
<222> LOCATION: (236)..(236)
<223> OTHER INFORMATION: Xaa = any amino acid

<400> SEQUENCE: 63

Met Ala Glu Glu Ala Ser Ser Gly Ile Arg Val Gln Gly Met Gln Phe
1               5                   10                  15

Ala Tyr Asp Ala Gln Pro Pro Leu Phe Cys Asp Phe Ser Leu Glu Ile
            20                  25                  30

Thr Pro Gly Ser Arg Cys Leu Leu Ile Gly Ala Asn Gly Ser Gly Lys
        35                  40                  45

Thr Thr Leu Leu Lys Ile Leu Ala Gly Lys Gln Met Val Gly Gly Arg
50                  55                  60

Asp Val Val Arg Val Leu Asn Cys Ser Ala Phe His Asp Thr His Leu
65                  70                  75                  80

Val Cys Ser Gly Asp Leu Ala Tyr Leu Gly Gly Ser Trp Thr Lys Thr
                85                  90                  95

Val Gly Ser Ala Gly Glu Leu Pro Leu Gln Gly Asp Phe Ser Ala Glu
            100                 105                 110

His Met Ile Phe Gly Val Glu Gly Thr Asp Pro Val Arg Arg Asp Lys
        115                 120                 125

Leu Ile Glu Leu Leu Asp Ile Asp Leu Arg Trp Arg Met His Lys Val
130                 135                 140

Ser Asp Gly Gln Arg Arg Arg Val Gln Ile Cys Met Gly Leu Leu His
145                 150                 155                 160

Pro Phe Lys Val Leu Leu Leu Asp Glu Val Thr Val Asp Leu Asp Val
                165                 170                 175

Val Ala Arg Met Asp Leu Leu Asp Phe Phe Lys Glu Glu Cys Glu Gln
            180                 185                 190

Arg Gly Ala Thr Ile Val Tyr Ala Thr His Ile Phe Asp Gly Leu Glu
        195                 200                 205

Thr Trp Ala Thr His Leu Ala Tyr Ile Gln Asp Gly Glu Leu Lys Arg
210                 215                 220

Ala Glu Lys Leu Ser Glu Val Asn Glu Leu Lys Xaa Ser Val Asn Leu
225                 230                 235                 240

Leu Ser Val Val Glu Ser Trp Leu Arg Ala Glu Thr Lys Ser Asp Lys
                245                 250                 255

Lys Lys Ser Ser Asn Pro Pro Ala Gln Ile Lys Lys Thr Ser Pro Phe
            260                 265                 270

Ala Ser Ser Ala Phe Thr Ser Ser Arg His Met Ala Tyr Tyr Arg
        275                 280                 285

<210> SEQ ID NO 64
<211> LENGTH: 296
<212> TYPE: PRT
<213> ORGANISM: Glycine soja
<220> FEATURE:
<221> NAME/KEY: MISC_FEATURE
<222> LOCATION: (1)..(296)
<223> OTHER INFORMATION: ABC Transporter

<400> SEQUENCE: 64

Met Asn Ser Ser Leu Ser Gly Asn Gly Gly Ser Thr Thr Met Ala Ala
1               5                   10                  15

Glu Asn Glu Asp Ser Cys Gly Ile Arg Val Thr Gly Met Gln Phe Ser

```
                20                  25                  30
Tyr Asp Val Gln Gln Pro Pro Leu Phe Leu Asp Phe Asn Leu Asn Val
            35                  40                  45
Ser Pro Gly Ser Arg Cys Leu Leu Val Gly Ala Asn Gly Ser Gly Lys
 50                  55                  60
Thr Thr Leu Leu Lys Ile Leu Ala Gly Lys His Met Val Gly Gly Arg
 65                  70                  75                  80
Asp Val Val Arg Val Leu Ser Gly Ser Ala Phe His Asp Thr Gln Leu
                85                  90                  95
Val Cys Ser Gly Asp Leu Ala Tyr Leu Gly Gly Ser Trp Ser Lys Asn
            100                 105                 110
Val Gly Ser Ala Gly Glu Ile Pro Leu Gln Gly Asp Phe Ser Ala Glu
        115                 120                 125
His Met Ile Phe Gly Val Glu Gly Ala Asp Pro Glu Arg Arg Asp Lys
        130                 135                 140
Leu Ile Glu Leu Leu Asp Ile Asp Leu Gln Trp Arg Met His Lys Val
145                 150                 155                 160
Ser Asp Gly Gln Arg Arg Val Gln Ile Cys Leu Gly Leu Leu His
                165                 170                 175
Pro Tyr Lys Val Leu Leu Asp Glu Val Thr Val Asp Leu Asp Val
            180                 185                 190
Val Thr Arg Met Asp Leu Leu Asp Phe Phe Lys Glu Glu Cys Glu Gln
        195                 200                 205
Arg Glu Ala Ile Ile Val Tyr Ala Thr His Ile Phe Asp Gly Leu Glu
    210                 215                 220
Thr Trp Ala Thr His Leu Ala Tyr Ile Gln Asp Gly Glu Leu Arg Arg
225                 230                 235                 240
Ala Glu Lys Ile Ser Asn Val Asn Glu Leu Lys Ser Ser Thr Asn Leu
                245                 250                 255
Leu Ser Val Val Glu Ala Trp Leu Arg Ala Glu Thr Lys Leu Glu Lys
            260                 265                 270
Lys Asn Pro Val Gln Lys Thr Ser Val Ala Ser Ser Pro Phe Phe Ser
        275                 280                 285
Ser Arg His Met Ala Tyr Tyr Arg
        290                 295

<210> SEQ ID NO 65
<211> LENGTH: 286
<212> TYPE: PRT
<213> ORGANISM: Coffea canephora
<220> FEATURE:
<221> NAME/KEY: MISC_FEATURE
<222> LOCATION: (1)..(286)
<223> OTHER INFORMATION: ABC Transporter

<400> SEQUENCE: 65

Met Glu Glu Ser Ser Cys Ser Ile Gln Val Asn Gly Met Gln Phe Ala
  1               5                  10                  15

Tyr Glu Ile Gln Thr Pro Leu Phe Phe Asp Phe Thr Ile Asn Ile Ser
                20                  25                  30

Pro Gly Ser Arg Cys Leu Leu Val Gly Ser Asn Gly Ser Gly Lys Thr
            35                  40                  45

Thr Leu Leu Lys Ile Leu Ala Gly Lys His Met Val Gly Gly Arg Asp
 50                  55                  60

Val Val Arg Val Leu Asn Phe Ser Ala Phe His Asp Thr Asn Leu Val
 65                  70                  75                  80
```

```
Cys Gly Gly Asp Leu Ala Tyr Leu Gly Asp Ser Trp Ser Lys Asn Val
                85                  90                  95

Gly Ser Ala Gly Glu Ile Pro Leu Gln Gly Asp Phe Ser Ala Glu His
            100                 105                 110

Met Ile Phe Gly Val Glu Gly Val Asp Pro Val Arg Arg Glu Lys Leu
        115                 120                 125

Ile Glu Leu Leu Asp Ile Asp Leu His Trp Arg Met His Lys Val Ser
    130                 135                 140

Asp Gly Gln Arg Arg Val Gln Ile Cys Met Gly Leu Leu His Pro
145                 150                 155                 160

Phe Lys Val Leu Leu Asp Glu Val Thr Val Asp Leu Asp Val Val
                165                 170                 175

Ala Arg Met Asp Leu Leu Asp Phe Phe Arg Glu Glu Cys Glu Gln Arg
            180                 185                 190

Gly Ala Thr Ile Val Tyr Ala Thr His Ile Phe Asp Gly Leu Glu Thr
        195                 200                 205

Trp Ala Thr Asp Ile Val Tyr Ile Gln Glu Gly Ile Leu Lys Arg His
    210                 215                 220

Glu Lys Leu Ser Asp Leu Ser Glu Leu Lys Ala Ser Pro Asn Leu Leu
225                 230                 235                 240

Ser Val Val Glu Ser Trp Leu Arg Ser Glu Thr Lys Val Glu Lys Lys
                245                 250                 255

Lys His Ile Thr Ala Gln Ser Pro Val Arg Lys Ser Ser Pro Phe Asp
            260                 265                 270

Ala Ser Pro Phe Arg Ser Ser Arg His Met Ala Tyr Tyr Arg
        275                 280                 285

<210> SEQ ID NO 66
<211> LENGTH: 297
<212> TYPE: PRT
<213> ORGANISM: Jatropha curcas
<220> FEATURE:
<221> NAME/KEY: MISC_FEATURE
<222> LOCATION: (1)..(297)
<223> OTHER INFORMATION: ABC Transporter

<400> SEQUENCE: 66

Met Ala Glu Lys Ala Trp Lys Asn Glu Glu Ser Glu Asn Glu Lys Gln
1               5                   10                  15

Asn Ser Ile Ser Val Val Gly Met Gln Phe Ala Tyr Glu Gly Gln Ser
            20                  25                  30

Pro Leu Phe Tyr Gly Phe Asn Leu Asn Thr Leu Pro Gly Ser Arg Tyr
        35                  40                  45

Leu Leu Val Gly Ala Asn Gly Ser Gly Lys Thr Thr Leu Leu Arg Ile
    50                  55                  60

Leu Ala Gly Lys His Met Val Gly Gly Arg Asp Val Val Gln Val Leu
65                  70                  75                  80

Asn Arg Ser Ala Phe His Asp Thr Gln Leu Val Cys Ser Gly Glu Leu
                85                  90                  95

Ala Tyr Leu Gly Gly Ser Trp Ser Lys Thr Val Gly Ser Ala Gly Glu
            100                 105                 110

Ile Pro Leu Gln Gly Asp Phe Ser Ala Glu Gln Met Ile Phe Gly Val
        115                 120                 125

Glu Gly Ile Asp Pro Ala Arg Arg Glu Lys Leu Ile Asp Leu Leu Asp
    130                 135                 140
```

```
Ile Asp Leu Gln Trp Arg Met His Lys Val Ser Asp Gly Gln Arg Arg
145                 150                 155                 160

Arg Val Gln Ile Cys Met Gly Leu Leu Val Pro Phe Lys Val Leu Leu
            165                 170                 175

Leu Asp Glu Val Thr Val Asp Leu Asp Val Val Ala Arg Ile Asp Leu
        180                 185                 190

Leu Glu Phe Phe Lys Gln Glu Cys Glu Gln Arg Gly Ala Thr Ile Val
    195                 200                 205

Tyr Ala Thr His Ile Phe Asp Gly Leu Glu Thr Trp Ala Thr His Leu
        210                 215                 220

Ala Tyr Ile Gln Asp Gly Glu Leu Arg Arg Ala Lys Lys Leu Thr Glu
225                 230                 235                 240

Val Ser Glu Leu Arg Ser Ser Ala Asn Leu Leu Ser Val Val Glu Ser
            245                 250                 255

Trp Leu Arg Ser Glu Thr Lys Ser Glu Lys Glu Lys Pro Thr Asn Pro
        260                 265                 270

Pro Pro Glu Lys Gln Lys Thr Ser Pro Phe Gly Ala Ser Pro Phe Met
    275                 280                 285

Ser Ser Arg His Met Ala Tyr Tyr Arg
    290                 295
```

<210> SEQ ID NO 67
<211> LENGTH: 290
<212> TYPE: PRT
<213> ORGANISM: Arachis duranensis
<220> FEATURE:
<221> NAME/KEY: MISC_FEATURE
<222> LOCATION: (1)..(290)
<223> OTHER INFORMATION: ABC Transporter

<400> SEQUENCE: 67

```
Met Ala Val Glu Glu Lys Glu Gly Ser Met Gly Ile Arg Val His
1               5                   10                  15

Gly Met Gln Phe Ser Tyr Glu Trp Gln Ser Pro Leu Phe Val Asp Phe
            20                  25                  30

Lys Leu Asn Val Ser Pro Gly Ser Arg Cys Leu Leu Leu Gly Ala Asn
        35                  40                  45

Gly Ser Gly Lys Thr Thr Leu Leu Lys Ile Leu Ala Gly Lys His Met
    50                  55                  60

Val Gly Gly Arg Asp Val Val Arg Val Leu Asn Gly Ser Ala Phe His
65                  70                  75                  80

Asp Thr His Leu Val Cys Ser Gly Asp Leu Ala Tyr Leu Gly Gly Ser
            85                  90                  95

Trp Ser Lys Thr Ile Gly Ser Ala Gly Asp Val Pro Leu Gln Gly Asp
        100                 105                 110

Phe Ser Ala Glu His Met Ile Phe Gly Val Glu Gly Ala Asp Pro Asp
    115                 120                 125

Arg Arg Asn Lys Leu Ile Glu Leu Leu Asp Ile Asp Leu Gln Trp Arg
130                 135                 140

Met His Lys Val Ser Asp Gly Gln Arg Arg Val Gln Ile Cys Leu
145                 150                 155                 160

Gly Leu Leu His Pro Phe Lys Val Leu Leu Leu Asp Glu Val Thr Val
            165                 170                 175

Asp Leu Asp Val Val Thr Arg Met Asp Leu Leu Glu Phe Phe Lys Glu
        180                 185                 190

Glu Cys Glu Gln Arg Gln Ala Thr Ile Val Tyr Ala Thr His Ile Phe
    195                 200                 205
```

```
                195                 200                 205
Asp Gly Leu Glu Thr Trp Ala Thr His Leu Ala Tyr Ile Gln Ala Gly
    210                 215                 220

Glu Leu Arg Arg Ala Glu Lys Leu Ser Asp Val Asp Glu Leu Lys Ser
225                 230                 235                 240

Ser Ala Asn Leu Leu Ser Val Val Glu Thr Trp Leu Arg Ala Glu Thr
                245                 250                 255

Arg Asn Glu Lys Lys Lys Pro Val Gln Asn Thr Ala Gln Thr Gln Lys
            260                 265                 270

Thr Ser Val Ala Ser Ser Pro Phe Phe Ser Ser Arg His Met Ala Tyr
        275                 280                 285

Tyr Arg
    290

<210> SEQ ID NO 68
<211> LENGTH: 290
<212> TYPE: PRT
<213> ORGANISM: Arachis ipaensis
<220> FEATURE:
<221> NAME/KEY: MISC_FEATURE
<222> LOCATION: (1)..(290)
<223> OTHER INFORMATION: ABC Transporter

<400> SEQUENCE: 68

Met Ala Val Glu Glu Lys Glu Gly Ser Met Gly Ile Arg Val His
1               5                   10                  15

Gly Met Gln Phe Ser Tyr Glu Trp Gln Ser Pro Leu Phe Val Asp Phe
                20                  25                  30

Lys Leu Asn Val Ser Pro Gly Ser Arg Cys Leu Leu Leu Gly Ala Asn
            35                  40                  45

Gly Ser Gly Lys Thr Thr Leu Leu Lys Ile Leu Ala Gly Lys His Met
    50                  55                  60

Val Gly Gly Arg Asp Val Val Arg Val Leu Asn Gly Ser Ala Phe His
65                  70                  75                  80

Asp Thr His Leu Val Cys Ser Gly Asp Leu Ala Tyr Leu Gly Gly Ser
                85                  90                  95

Trp Ser Lys Thr Ile Gly Ser Ala Gly Asp Val Pro Leu Gln Gly Asp
            100                 105                 110

Phe Ser Ala Glu His Met Ile Phe Gly Val Gly Ala Asp Pro Asp
        115                 120                 125

Arg Arg Asn Lys Leu Ile Glu Leu Leu Asp Ile Asp Leu Gln Trp Arg
    130                 135                 140

Met His Lys Val Ser Asp Gly Gln Arg Arg Val Gln Ile Cys Leu
145                 150                 155                 160

Gly Leu Leu His Pro Phe Lys Val Leu Leu Asp Glu Val Thr Val
                165                 170                 175

Asp Leu Asp Val Val Thr Arg Met Asp Leu Leu Glu Phe Phe Lys Glu
            180                 185                 190

Glu Cys Glu Gln Arg Gln Ala Thr Ile Val Tyr Ala Thr His Ile Phe
        195                 200                 205

Asp Gly Leu Glu Thr Trp Ala Thr His Leu Ala Tyr Ile Gln Ala Gly
    210                 215                 220

Glu Leu Arg Lys Ala Glu Lys Leu Ser Asp Val Asp Glu Leu Lys Ser
225                 230                 235                 240

Ser Ala Asn Leu Leu Ser Val Val Glu Thr Trp Leu Arg Ala Glu Thr
                245                 250                 255
```

-continued

Arg Asn Glu Lys Lys Pro Val Gln Asn Thr Ala Gln Thr Gln Lys
              260             265                 270

Thr Ser Val Ala Ser Ser Pro Phe Phe Ser Ser Arg His Met Ala Tyr
    275                 280                 285

Tyr Arg
    290

<210> SEQ ID NO 69
<211> LENGTH: 290
<212> TYPE: PRT
<213> ORGANISM: Brassica napus
<220> FEATURE:
<221> NAME/KEY: MISC_FEATURE
<222> LOCATION: (1)..(290)
<223> OTHER INFORMATION: ABC Transporter

<400> SEQUENCE: 69

Met Ala Ala Lys Asp Gln Ala Thr Thr Ser Asp Asp Ala Ile Arg Val
1               5                   10                  15

Ser Gly Met Glu Phe Ser Tyr Glu Ala Glu Asp Pro Ile Phe Phe Asp
            20                  25                  30

Phe Asn Leu Asp Leu Pro Ala Gly Ser Arg Cys Leu Leu Val Gly Ala
        35                  40                  45

Asn Gly Ser Gly Lys Thr Thr Leu Leu Arg Ile Leu Ala Gly Lys His
50                  55                  60

Met Val Gly Gly Lys Asn Val Val Gln Val Leu Ser Arg Ser Ala Phe
65              70                  75                  80

His Asp Thr Gln Leu Val Cys Ser Gly Asp Leu Ser Tyr Leu Gly Gly
                85                  90                  95

Ser Trp Ser Lys Thr Val Gly Ser Ala Gly Glu Val Pro Leu Gln Gly
            100                 105                 110

Asp Phe Ser Ala Glu His Met Ile Phe Gly Val Glu Gly Ile Asp Pro
        115                 120                 125

Val Arg Arg Glu Lys Leu Ile Asp Leu Leu Asp Ile Asn Leu Gln Trp
130                 135                 140

Arg Met His Lys Val Ser Asp Gly Gln Lys Arg Arg Val Gln Ile Cys
145                 150                 155                 160

Met Gly Leu Leu His Pro Phe Lys Val Leu Leu Leu Asp Glu Val Thr
                165                 170                 175

Val Asp Leu Asp Val Val Ala Arg Met Asp Leu Leu Glu Phe Phe Lys
            180                 185                 190

Glu Glu Cys Asp Gln Arg Gly Ala Thr Ile Val Tyr Ala Thr His Ile
        195                 200                 205

Phe Asp Gly Leu Glu Thr Trp Ala Thr His Leu Ala Tyr Ile Gln Asn
    210                 215                 220

Gly Glu Leu Asn Arg Ser Ser Lys Met Ala Asp Ile Ser Glu Met Lys
225                 230                 235                 240

Thr Ser Pro Asn Leu Leu Ser Val Val Glu Ser Trp Leu Arg Ser Glu
                245                 250                 255

Thr Lys Ile Asp Lys Lys Lys Glu Pro Val Pro Ala Trp Lys Pro
            260                 265                 270

Thr Pro Phe Asp Asn Ser Pro Phe Arg Ser Ser Arg His Met Ala Tyr
        275                 280                 285

Tyr Arg
    290

```
<210> SEQ ID NO 70
<211> LENGTH: 286
<212> TYPE: PRT
<213> ORGANISM: Nicotiana sylvestris
<220> FEATURE:
<221> NAME/KEY: MISC_FEATURE
<222> LOCATION: (1)..(286)
<223> OTHER INFORMATION: ABC Transporter

<400> SEQUENCE: 70

Met Glu Gly Lys Ser Ser Ser Ile Gln Val Asn Gly Met Gln Phe Ser
1               5                   10                  15

Tyr Asp Phe Gln Ser Pro Ile Phe Phe Asp Phe Ser Leu Lys Ile Ser
            20                  25                  30

Pro Gly Ser Arg Cys Leu Leu Val Gly Ala Asn Gly Ser Gly Lys Thr
        35                  40                  45

Thr Leu Leu Arg Ile Leu Ala Gly Lys His Met Val Gly Gly Arg Asp
    50                  55                  60

Val Val Lys Val Leu Asn Phe Ser Ala Phe His Asp Thr His Leu Val
65                  70                  75                  80

Cys Asp Gly Asp Leu Ala Tyr Leu Gly Glu Ser Trp Ser Lys Asn Val
                85                  90                  95

Gly Ser Ala Gly Glu Ile Pro Leu Gln Gly Asp Phe Ser Ala Glu His
            100                 105                 110

Met Ile Phe Gly Val Glu Gly Val Asp Pro Val Arg Arg Glu Lys Leu
        115                 120                 125

Ile Glu Leu Leu Asp Ile Asp Leu Gln Trp Arg Met His Lys Val Ser
    130                 135                 140

Asp Gly Gln Arg Arg Arg Val Gln Ile Cys Met Gly Leu Leu His Pro
145                 150                 155                 160

Tyr Lys Val Leu Leu Leu Asp Glu Val Thr Val Asp Leu Asp Val Val
                165                 170                 175

Ala Arg Met Asp Leu Leu Asp Phe Phe Lys Glu Glu Cys Glu Gln Arg
            180                 185                 190

Gly Ala Thr Ile Val Tyr Ala Thr His Ile Phe Asp Gly Leu Glu Ser
        195                 200                 205

Trp Ala Thr Asp Leu Val Tyr Ile Gln Asp Gly Val Leu Lys Arg Ser
    210                 215                 220

Glu Lys Leu Pro Glu Leu Pro Glu Leu Lys Ser Ser Pro Asn Leu Leu
225                 230                 235                 240

Ser Val Val Glu Asn Trp Leu Arg Ser Glu Thr Thr Ile Glu Lys Lys
                245                 250                 255

Lys Pro Val Ile Ala Pro Pro Lys Val Gln Lys Ser Ser Pro Phe Gly
            260                 265                 270

Ser Ser Pro Phe Gln Ser Ser Arg His Met Ala Tyr Phe Arg
        275                 280                 285

<210> SEQ ID NO 71
<211> LENGTH: 283
<212> TYPE: PRT
<213> ORGANISM: Glycine max
<220> FEATURE:
<221> NAME/KEY: MISC_FEATURE
<222> LOCATION: (1)..(283)
<223> OTHER INFORMATION: ABC Transporter

<400> SEQUENCE: 71

Met Ala Ala Glu Asn Glu Asp Ser Cys Gly Ile Arg Val Thr Gly Met
```

```
            1               5                  10                 15
Gln Phe Ser Tyr Asp Val Gln Gln Pro Pro Leu Phe Leu Asp Phe Asn
                20                 25                 30

Leu Asn Val Ser Pro Gly Ser Arg Cys Leu Leu Val Gly Ala Asn Gly
                35                 40                 45

Ser Gly Lys Thr Thr Leu Leu Lys Ile Leu Ala Gly Lys His Met Val
    50                 55                 60

Gly Gly Arg Asp Val Val Arg Val Leu Ser Gly Ser Ala Phe His Asp
65                 70                 75                 80

Thr Gln Leu Val Cys Ser Gly Asp Leu Ala Tyr Leu Gly Gly Ser Trp
                85                 90                 95

Ser Lys Asn Val Gly Ser Ala Gly Glu Ile Pro Leu Gln Gly Asp Ser
                100                105                110

Ser Ala Glu His Met Ile Phe Gly Val Glu Gly Ala Asp Pro Glu Arg
                115                120                125

Arg Asp Lys Leu Ile Glu Leu Leu Asp Ile Asp Leu Gln Trp Arg Met
                130                135                140

His Lys Val Ser Asp Gly Gln Arg Arg Val Gln Ile Cys Leu Gly
145                 150                155                160

Leu Leu His Pro Tyr Lys Val Leu Leu Leu Asp Glu Val Thr Val Asp
                165                170                175

Leu Asp Val Val Thr Arg Met Asp Leu Leu Asp Phe Phe Lys Glu Glu
                180                185                190

Cys Glu Gln Arg Glu Ala Ile Ile Val Tyr Ala Thr His Ile Phe Asp
                195                200                205

Gly Leu Glu Thr Trp Ala Thr His Leu Ala Tyr Ile Gln Asp Gly Glu
    210                215                220

Leu Arg Arg Ala Glu Lys Ile Ser Asn Val Lys Glu Leu Lys Ser Ser
225                 230                235                240

Thr Asn Leu Leu Ser Val Val Glu Ala Trp Leu Arg Ala Glu Thr Lys
                245                250                255

Leu Glu Lys Lys Asn Pro Val Gln Lys Thr Ser Val Ala Ser Ser Pro
                260                265                270

Phe Phe Ser Ser Arg His Met Ala Tyr Tyr Arg
                275                280

<210> SEQ ID NO 72
<211> LENGTH: 287
<212> TYPE: PRT
<213> ORGANISM: Lotus japonicus
<220> FEATURE:
<221> NAME/KEY: MISC_FEATURE
<222> LOCATION: (1)..(287)
<223> OTHER INFORMATION: ABC Transporter

<400> SEQUENCE: 72

Met Ala Ile Gln Asp Ser Glu Arg Ser Gly Gly Gly Ile Arg Val
1               5                  10                 15

Gln Gly Met Gln Phe Thr Tyr Pro Gly Gln Gln Pro Pro Leu Phe Leu
                20                 25                 30

Asp Phe His Leu Asp Val Ser Pro Gly Ser Arg Cys Leu Leu Leu Gly
                35                 40                 45

Ala Asn Gly Ser Gly Lys Thr Thr Leu Leu Lys Ile Leu Thr Gly Lys
    50                 55                 60

His Met Val Gly Gly Arg Asp Val Val Arg Val Leu Asn Gly Ser Ala
65                 70                 75                 80
```

-continued

```
Phe His Asp Thr Gln Leu Val Cys Ser Gly Asp Leu Ser Tyr Leu Gly
                85                  90                  95

Gly Ser Trp Ser Lys Thr Ile Gly Cys Ala Gly Glu Ile Pro Leu Gln
            100                 105                 110

Gly Asp Phe Ser Ala Glu His Met Ile Phe Gly Val Glu Gly Ala Asp
        115                 120                 125

Pro Asp Arg Arg Asp Arg Leu Ile Glu Leu Leu Asp Ile Asp Leu Gln
    130                 135                 140

Trp Arg Met His Lys Val Ser Asp Gly Gln Arg Arg Val Gln Ile
145                 150                 155                 160

Cys Leu Gly Leu Leu His Pro Tyr Lys Ala Leu Leu Leu Asp Glu Val
                165                 170                 175

Thr Val Asp Leu Asp Val Val Thr Arg Met Asp Leu Leu Asp Phe Phe
                180                 185                 190

Lys Glu Glu Cys Glu Gln Arg Glu Ala Thr Ile Val Tyr Ala Thr His
                195                 200                 205

Ile Phe Asp Gly Leu Glu Thr Trp Ala Thr His Leu Ala Tyr Ile Gln
        210                 215                 220

Glu Gly Glu Leu Lys Arg Thr Gly Lys Ile Ser Asp Val Asn Glu Leu
225                 230                 235                 240

Lys Ser Ser Ala Asn Leu Leu Ser Val Val Glu Ser Trp Leu Arg Ala
                245                 250                 255

Glu Thr Lys Leu Glu Lys Lys Asn Pro Thr Ser Asn Val Gln Lys Thr
                260                 265                 270

Ser Ser Ser Pro Phe Phe Ser Ser Arg His Met Ala Tyr Tyr Arg
                275                 280                 285
```

<210> SEQ ID NO 73
<211> LENGTH: 296
<212> TYPE: PRT
<213> ORGANISM: Phaseolus vulgaris
<220> FEATURE:
<221> NAME/KEY: MISC_FEATURE
<222> LOCATION: (1)..(296)
<223> OTHER INFORMATION: ABC Transporter

<400> SEQUENCE: 73

```
Met Asn Thr Ser Leu Ser Ser Met Ala Glu Tyr Ser Leu Thr Met Ala
1               5                   10                  15

Ala Ala Asp Glu Asp Ser Leu Gly Ile Arg Val Arg Gly Met Gln Phe
                20                  25                  30

Ser Tyr Glu Ala Gln Gln Pro Pro Leu Phe Leu Asp Phe Lys Leu Asn
            35                  40                  45

Val Glu Pro Gly Ser Arg Cys Leu Leu Val Gly Ala Asn Gly Ser Gly
        50                  55                  60

Lys Thr Thr Leu Leu Lys Ile Leu Ala Gly Lys His Met Val Gly Gly
65                  70                  75                  80

Arg Asp Val Val Arg Val Leu Asn Gly Ser Ala Phe His Asp Thr Gln
                85                  90                  95

Leu Val Cys Ser Gly Asp Leu Ala Tyr Leu Gly Gly Ser Trp Ser Lys
            100                 105                 110

Asn Val Gly Ser Ala Gly Glu Ile Pro Leu Gln Gly Asp Phe Ser Ala
        115                 120                 125

Glu His Met Ile Phe Gly Val Gly Ala Asp Pro Asp Arg Arg Asp
    130                 135                 140
```

```
Lys Leu Ile Glu Leu Leu Asp Ile Asp Leu Gln Trp Arg Met His Lys
145                 150                 155                 160

Val Ser Asp Gly Gln Arg Arg Val Gln Ile Cys Leu Gly Leu Leu
            165                 170                 175

Tyr Pro Tyr Lys Val Leu Leu Leu Asp Glu Val Thr Val Asp Leu Asp
            180                 185                 190

Val Val Thr Arg Met Asp Leu Leu Asp Phe Phe Arg Glu Glu Cys Glu
            195                 200                 205

Gln Arg Glu Ala Thr Ile Val Tyr Ala Thr His Ile Phe Asp Gly Leu
    210                 215                 220

Glu Thr Trp Ala Thr His Leu Ala Tyr Ile Gln Asp Gly Glu Leu Arg
225                 230                 235                 240

Arg Ala Glu Lys Ile Ser Asp Val Asn Glu Leu Lys Ser Ser Ile Asn
                245                 250                 255

Leu Leu Ser Val Val Glu Ala Trp Leu Arg Ala Glu Thr Lys Val Val
            260                 265                 270

Lys Lys Asn Pro Val Gln Lys Thr Phe Ala Ser Asn Pro Phe Phe Ser
            275                 280                 285

Ser Arg His Met Ala Tyr Tyr Arg
    290                 295

<210> SEQ ID NO 74
<211> LENGTH: 286
<212> TYPE: PRT
<213> ORGANISM: Nicotiana tomentosiformis
<220> FEATURE:
<221> NAME/KEY: MISC_FEATURE
<222> LOCATION: (1)..(286)
<223> OTHER INFORMATION: ABC Transporter

<400> SEQUENCE: 74

Met Glu Gly Glu Ser Asn Ser Ile Gln Val Asp Gly Met Gln Phe Ser
1               5                   10                  15

Tyr Asp Phe Gln Ser Pro Ile Phe Phe Asp Phe Ser Leu Lys Ile Ser
            20                  25                  30

Pro Gly Ser Arg Cys Leu Leu Val Gly Ala Asn Gly Ser Gly Lys Thr
        35                  40                  45

Thr Leu Leu Arg Ile Leu Ala Gly Lys His Met Val Gly Gly Arg Asp
    50                  55                  60

Val Val Lys Val Leu Asn Phe Ser Ala Phe His Asp Thr His Leu Val
65                  70                  75                  80

Cys Asp Gly Asp Leu Ala Tyr Leu Gly Glu Ser Trp Ser Lys Asn Val
                85                  90                  95

Gly Ser Ala Gly Glu Ile Pro Leu Gln Gly Asp Phe Ser Ala Glu His
            100                 105                 110

Met Ile Phe Gly Val Glu Gly Val Asp Pro Val Arg Arg Glu Lys Leu
            115                 120                 125

Ile Glu Leu Leu Asp Ile Asp Leu Gln Trp Arg Met His Lys Val Ser
    130                 135                 140

Asp Gly Gln Arg Arg Val Gln Ile Cys Met Gly Leu Leu His Pro
145                 150                 155                 160

Tyr Lys Val Leu Leu Leu Asp Glu Val Thr Val Asp Leu Asp Val Val
                165                 170                 175

Ala Arg Met Asp Leu Leu Asp Phe Phe Lys Glu Glu Cys Glu Gln Arg
            180                 185                 190

Gly Ala Thr Ile Val Tyr Ala Thr His Ile Phe Asp Gly Leu Glu Ser
```

```
            195                 200                 205
Trp Ala Thr Asp Leu Val Tyr Ile Gln Asp Gly Val Leu Lys Arg Ser
210                 215                 220

Glu Lys Leu Pro Glu Leu Pro Glu Leu Lys Ser Ser Pro Asn Leu Leu
225                 230                 235                 240

Ser Val Val Glu Asn Trp Leu Arg Ser Glu Thr Thr Ile Glu Lys Lys
                245                 250                 255

Lys Pro Val Ile Ala Pro Pro Lys Val Gln Lys Ser Ser Pro Phe Gly
                260                 265                 270

Ser Ser Pro Phe Gln Ser Ser Arg His Met Ala Tyr Phe Arg
                275                 280                 285

<210> SEQ ID NO 75
<211> LENGTH: 291
<212> TYPE: PRT
<213> ORGANISM: Arabis alpina
<220> FEATURE:
<221> NAME/KEY: MISC_FEATURE
<222> LOCATION: (1)..(291)
<223> OTHER INFORMATION: ABC Transporter

<400> SEQUENCE: 75

Met Ala Glu Lys His Ala Arg Thr Ser Gly Asp Asp Ala Ile Arg
1               5                   10                  15

Val Ser Gly Met Glu Phe Gly Tyr Glu Val Gln Asp Pro Ile Phe Phe
                20                  25                  30

Asp Phe Asn Leu Asp Leu Pro Ala Gly Ser Arg Cys Leu Leu Val Gly
                35                  40                  45

Ala Asn Gly Ser Gly Lys Thr Thr Leu Leu Lys Ile Met Ala Gly Lys
50                  55                  60

His Met Val Gly Gly Lys Asn Val Val Gln Val Leu Ser Arg Ser Ala
65                  70                  75                  80

Phe His Asp Thr Gln Leu Val Cys Ser Gly Asp Leu Ser Tyr Leu Gly
                85                  90                  95

Gly Ser Trp Ser Lys Thr Val Gly Ser Ala Gly Glu Val Pro Leu Gln
                100                 105                 110

Gly Asp Phe Ser Ala Glu His Met Ile Phe Gly Val Glu Gly Thr Asp
                115                 120                 125

Pro Val Arg Arg Glu Lys Leu Ile Asp Leu Leu Asp Ile Asn Leu Asn
                130                 135                 140

Trp Arg Met His Lys Val Ser Asp Gly Gln Lys Arg Arg Val Gln Ile
145                 150                 155                 160

Cys Met Gly Leu Leu His Pro Phe Lys Val Leu Leu Leu Asp Glu Val
                165                 170                 175

Thr Val Asp Leu Asp Val Val Ala Arg Met Asp Leu Leu Glu Phe Phe
                180                 185                 190

Lys Glu Glu Cys Asp Gln Arg Gly Ala Thr Ile Val Tyr Ala Thr His
                195                 200                 205

Ile Phe Asp Gly Leu Glu Thr Trp Ala Thr His Leu Ala Tyr Ile Gln
                210                 215                 220

Asp Gly Gln Leu Asn Arg Ser Ser Met Ala Asp Ile Asn Glu Leu
225                 230                 235                 240

Lys Thr Ala Pro Asn Leu Leu Ser Val Val Glu Ser Trp Leu Arg Ser
                245                 250                 255

Glu Thr Lys Leu Glu Lys Lys Arg Lys Pro Val Ala Ala Trp Lys
                260                 265                 270
```

-continued

```
Pro Ser Gln Phe Asp Thr Ser Pro Phe Arg Ser Ser Arg His Met Ala
        275                 280                 285

Tyr Tyr Arg
    290

<210> SEQ ID NO 76
<211> LENGTH: 302
<212> TYPE: PRT
<213> ORGANISM: Cephalotus follicularis
<220> FEATURE:
<221> NAME/KEY: MISC_FEATURE
<222> LOCATION: (1)..(302)
<223> OTHER INFORMATION: ABC Transporter

<400> SEQUENCE: 76

Met Leu Gln Arg Arg Lys Lys Met Gly Glu Glu Glu Asn Glu Lys
1               5                   10                  15

Pro Trp Ser Asn Ser Ser Ser Ile Arg Val Cys Gly Met Gln Phe
                20                  25                  30

Ala Tyr Asp Ala Gln Ser Pro Val Phe Val Asp Phe Asn Leu Asn Val
            35                  40                  45

Ser Pro Gly Ser Arg Trp Leu Leu Val Gly Ala Asn Gly Ser Gly Lys
        50                  55                  60

Thr Thr Leu Leu Lys Ile Leu Ala Gly Lys His Met Val Gly Arg
65                  70                  75                  80

Asp Val Val Ser Val Leu Asn Gly Ser Ala Phe His Asp Thr Gln Leu
                85                  90                  95

Val Cys Ser Gly Asp Leu Ala Tyr Leu Gly Ala Ser Trp Thr Lys Thr
            100                 105                 110

Leu Gly Ser Ala Gly Glu Ile Pro Leu Gln Gly Asp Phe Ser Ala Glu
        115                 120                 125

His Met Ile Phe Gly Val Glu Gly Ile Asp Pro Val Arg Arg Glu Lys
    130                 135                 140

Leu Ile Glu Leu Leu Asp Ile Asp Leu Arg Trp Arg Met His Lys Val
145                 150                 155                 160

Ser Asp Gly Gln Arg Arg Arg Val Gln Ile Cys Met Gly Leu Leu His
                165                 170                 175

Pro Phe Gln Val Leu Leu Leu Asp Glu Val Thr Val Asp Leu Asp Val
            180                 185                 190

Val Ala Arg Met Asp Leu Leu Asp Phe Phe Lys Glu Glu Cys Asp Gln
        195                 200                 205

Arg Gly Ala Thr Ile Val Tyr Ala Thr His Ile Phe Asp Gly Leu Glu
    210                 215                 220

Thr Trp Ala Thr His Leu Ala Tyr Ile Gln Asp Gly Gln Leu Arg Arg
225                 230                 235                 240

Ala Glu Lys Leu Leu Glu Ile Asp Glu Leu Lys Ser Ser Val Asn Leu
                245                 250                 255

Leu Ser Val Val Glu Ser Trp Leu Arg Ser Glu Thr Lys Cys Glu Lys
            260                 265                 270

Lys Lys Leu Ile Asn Pro Thr Pro Gln Ile Gln Val Ser Pro Phe Gly
        275                 280                 285

Thr Ser Pro Phe Met Pro Ser Arg His Met Ala Tyr Tyr Arg
    290                 295                 300

<210> SEQ ID NO 77
<211> LENGTH: 329
```

```
<212> TYPE: PRT
<213> ORGANISM: Gossypium raimondii
<220> FEATURE:
<221> NAME/KEY: MISC_FEATURE
<222> LOCATION: (1)..(329)
<223> OTHER INFORMATION: ABC Transporter

<400> SEQUENCE: 77

Met Ala Glu Gln Ala Cys Cys Arg Ser Gly Glu Gly Lys Glu Asn Gly
1               5                   10                  15

Gly Asp Ser Gln Gly Ile Thr Val Cys Gly Met Gln Phe Ala Tyr Glu
            20                  25                  30

Leu Gln His Pro Leu Phe Phe Asp Phe Asn Leu Asp Ile Ala Arg Gly
        35                  40                  45

Ser Arg Cys Leu Leu Val Gly Ala Asn Gly Ser Gly Lys Thr Thr Leu
50                  55                  60

Leu Lys Ile Leu Ala Gly Lys His Met Val Gly Arg Glu Val Val
65                  70                  75                  80

Arg Val Leu Asn Arg Ser Ala Phe His Asp Thr Gln Leu Val Cys Gly
                85                  90                  95

Gly Asp Leu Ala Tyr Leu Gly Gly Ser Trp Ser Lys Thr Ile Gly Ser
            100                 105                 110

Ala Val Ser Lys Phe Ser Tyr Phe Phe Lys Ile Asn Ile His His
        115                 120                 125

Phe Arg Leu Lys Leu Gln Ile Tyr Cys Ala Lys His Met Gln Gly Glu
130                 135                 140

Val Pro Leu Gln Gly Asp Phe Ser Ala Glu His Met Ile Phe Gly Val
145                 150                 155                 160

Glu Gly Ile Asp Pro Val Arg Arg Asp Lys Leu Ile Glu Leu Leu Asp
                165                 170                 175

Ile Asp Leu Gln Trp Arg Met His Lys Val Ser Asp Gly Gln Arg Arg
            180                 185                 190

Arg Val Gln Ile Cys Met Gly Leu Leu His Pro Phe Gln Val Leu Leu
        195                 200                 205

Leu Asp Glu Val Thr Val Asp Leu Asp Val Val Ala Arg Met Asp Leu
210                 215                 220

Leu Asp Phe Phe Lys Glu Glu Cys Glu Gln Arg Gly Ala Thr Val Val
225                 230                 235                 240

Tyr Ala Thr His Ile Phe Asp Gly Leu Glu Thr Trp Ala Thr His Leu
                245                 250                 255

Ala Tyr Ile Gln Asp Gly Gln Leu Lys Arg Ser Glu Lys Leu Thr Glu
            260                 265                 270

Ile Asn Glu Leu Lys Ser Ser Glu Asn Leu Leu Ser Val Val Glu Ala
        275                 280                 285

Trp Leu Arg Ser Glu Thr Lys Cys Glu Lys Lys Pro Ser Asn Ser
290                 295                 300

Pro Ala Gln Val Gln Lys Ser Ser Pro Phe Gly Thr Ser Pro Phe Met
305                 310                 315                 320

Ser Ser Arg His Met Ala Tyr Tyr Arg
                325

<210> SEQ ID NO 78
<211> LENGTH: 282
<212> TYPE: PRT
<213> ORGANISM: Vigna angularis
<220> FEATURE:
<221> NAME/KEY: MISC_FEATURE
```

<222> LOCATION: (1)..(282)
<223> OTHER INFORMATION: ABC Transporter

<400> SEQUENCE: 78

```
Met Ala Ala Ala Glu Glu Asp Phe Pro Gly Ile Arg Val Arg Gly Met
1               5                   10                  15

Gln Phe Ser Tyr Glu Ala Gln Gln Pro Pro Leu Phe Leu Asp Phe Asn
            20                  25                  30

Leu Asn Val Glu Pro Gly Ser Arg Cys Leu Leu Val Gly Ala Asn Gly
        35                  40                  45

Ser Gly Lys Thr Thr Leu Leu Lys Ile Leu Ala Gly Lys His Met Val
    50                  55                  60

Gly Gly Arg Asp Val Val Arg Val Leu Asn Gly Ser Ala Phe His Asp
65                  70                  75                  80

Thr Gln Leu Val Cys Ser Gly Asp Leu Ala Tyr Leu Gly Gly Ser Trp
                85                  90                  95

Ser Lys Asn Val Gly Ser Ala Gly Glu Ile Pro Leu Gln Gly Asp Phe
            100                 105                 110

Ser Ala Glu His Met Ile Phe Gly Val Glu Gly Ala Asp Pro Asp Arg
        115                 120                 125

Arg Asp Lys Leu Ile Glu Leu Leu Asp Ile Asp Leu Gln Trp Arg Met
    130                 135                 140

His Lys Val Ser Asp Gly Gln Arg Arg Val Gln Ile Cys Leu Gly
145                 150                 155                 160

Leu Leu Tyr Pro Tyr Lys Val Leu Leu Asp Glu Val Thr Val Asp
                165                 170                 175

Leu Asp Val Val Thr Arg Met Asp Leu Leu Glu Phe Phe Arg Glu Glu
            180                 185                 190

Cys Glu Gln Arg Glu Ala Thr Ile Val Tyr Ala Thr His Ile Phe Asp
        195                 200                 205

Gly Leu Glu Ala Trp Ala Thr His Leu Ala Tyr Ile Gln Asp Gly Glu
    210                 215                 220

Leu Arg Arg Ala Glu Lys Ile Ser Asp Val Asn Glu Leu Lys Ser Ser
225                 230                 235                 240

Thr Asn Leu Leu Ser Val Val Glu Asp Trp Leu Arg Ala Glu Thr Lys
                245                 250                 255

Gly Val Lys Lys Lys Pro Val Gln Lys Asn Phe Ala Ser Ser Pro Phe
            260                 265                 270

Phe Ser Ser Arg His Met Ala Tyr Tyr Arg
        275                 280
```

<210> SEQ ID NO 79
<211> LENGTH: 286
<212> TYPE: PRT
<213> ORGANISM: Nicotiana attenuata
<220> FEATURE:
<221> NAME/KEY: MISC_FEATURE
<222> LOCATION: (1)..(286)
<223> OTHER INFORMATION: ABC Transporter

<400> SEQUENCE: 79

```
Met Glu Gly Arg Ser Asn Ser Ile Leu Val Asn Gly Met Gln Phe Ser
1               5                   10                  15

Tyr Asp Phe Gln Ser Pro Ile Phe Phe Asp Phe Ser Leu Lys Ile Ser
            20                  25                  30

Pro Gly Ser Arg Cys Leu Leu Val Gly Ala Asn Gly Ser Gly Lys Thr
        35                  40                  45
```

```
Thr Leu Leu Arg Ile Leu Ala Gly Lys His Met Val Gly Gly Arg Asp
     50                  55                  60

Val Val Lys Val Leu Asn Phe Ser Ala Phe His Asp Thr His Leu Val
 65                  70                  75                  80

Cys Asp Gly Asp Leu Ala Tyr Leu Gly Glu Ser Trp Ser Lys Asn Ala
                 85                  90                  95

Gly Ser Ala Gly Glu Ile Pro Leu Gln Gly Asp Phe Ser Ala Glu His
                100                 105                 110

Met Ile Phe Gly Val Glu Gly Val Asp Pro Val Arg Arg Glu Lys Leu
                115                 120                 125

Ile Glu Leu Leu Asp Ile Asn Leu Gln Trp Arg Met His Lys Val Ser
    130                 135                 140

Asp Gly Gln Arg Arg Val Gln Ile Cys Met Gly Leu Leu His Pro
145                 150                 155                 160

Tyr Lys Val Leu Leu Leu Asp Glu Val Thr Val Asp Leu Asp Val Val
                165                 170                 175

Ala Arg Met Asp Leu Leu Asp Phe Phe Lys Glu Glu Cys Glu Gln Arg
                180                 185                 190

Gly Ala Thr Ile Val Tyr Ala Thr His Ile Phe Asp Gly Leu Glu Ser
                195                 200                 205

Trp Ala Thr Asp Leu Val Tyr Ile Gln Asp Gly Val Leu Lys Arg Ser
    210                 215                 220

Glu Lys Leu Pro Glu Leu Pro Glu Leu Lys Ser Ser Pro Asn Leu Leu
225                 230                 235                 240

Ser Val Val Glu Asn Trp Leu Arg Ser Glu Thr Thr Ile Glu Lys Lys
                245                 250                 255

Lys Pro Val Ile Ala Pro Pro Lys Val Gln Lys Ser Ser Pro Phe Gly
                260                 265                 270

Ser Ser Pro Phe Gln Ser Ser Arg His Met Ala Tyr Phe Arg
            275                 280                 285

<210> SEQ ID NO 80
<211> LENGTH: 307
<212> TYPE: PRT
<213> ORGANISM: Cucumis melo
<220> FEATURE:
<221> NAME/KEY: MISC_FEATURE
<222> LOCATION: (1)..(307)
<223> OTHER INFORMATION: ABC Transporter

<400> SEQUENCE: 80

Met Ala Asp Asn Gly Ile Ser Leu Val Gly Asn Asp Gly Ile Glu Val
 1                   5                  10                  15

Val Asp Glu Lys Gly Ser Pro Gly Ile Lys Val Gln Ala Met Gln Phe
                 20                  25                  30

Ser Tyr Glu Ser Asp Ser Pro Leu Phe Val Glu Phe Asn Leu Gln Ile
             35                  40                  45

Gly Ser Gly Ser Arg Cys Leu Leu Val Gly Ala Asn Gly Ser Gly Lys
         50                  55                  60

Thr Thr Leu Leu Lys Ile Leu Ala Gly Lys His Met Val Gly Gly Arg
 65                  70                  75                  80

Asp Val Val Gln Val Leu Asn Gly Ser Ala Phe His Asp Thr Gln Leu
                 85                  90                  95

Val Cys Ser Gly Asp Leu Ala Tyr Leu Gly Gly Ser Trp Ser Lys Thr
                100                 105                 110
```

```
Val Ser Ser Ala Gly Glu Val Ala Leu Gln Gly Asp Phe Ser Ala Glu
            115                 120                 125

His Met Ile Phe Gly Val Glu Gly Thr Asp Pro Glu Arg Arg Glu Arg
        130                 135                 140

Leu Ile Asp Leu Leu Asp Ile Asp Leu Arg Trp Arg Met His Lys Val
145                 150                 155                 160

Ser Asp Gly Gln Arg Arg Val Gln Ile Cys Met Gly Leu Leu His
                165                 170                 175

Pro Phe Lys Val Leu Leu Asp Glu Val Thr Val Asp Leu Asp Val
                180                 185                 190

Val Ala Arg Met Asp Leu Leu Asp Phe Leu Lys Glu Glu Cys Asp Gln
        195                 200                 205

Arg Gly Ala Thr Ile Val Tyr Ala Thr His Ile Phe Asp Gly Leu Glu
        210                 215                 220

Thr Trp Ala Thr His Leu Ala Tyr Ile Gln Asp Gly Glu Leu Arg Lys
225                 230                 235                 240

Ser Glu Lys Leu Ser Ala Val Glu Glu Leu Lys Thr Cys Ala Asn Leu
                245                 250                 255

Leu Ser Val Val Glu Thr Trp Leu Arg Ala Glu Thr Lys Leu Glu Lys
                260                 265                 270

Lys Lys Lys Lys Gln Pro Ile Gln Pro Pro Ser Asn Asn Gln Lys Ile
                275                 280                 285

Val Ser Pro Phe Gly Ser Ser Pro Phe Thr Ser Ser Arg His Met Ala
                290                 295                 300

Tyr Tyr Arg
305

<210> SEQ ID NO 81
<211> LENGTH: 289
<212> TYPE: PRT
<213> ORGANISM: Lupinus angustifolius
<220> FEATURE:
<221> NAME/KEY: MISC_FEATURE
<222> LOCATION: (1)..(289)
<223> OTHER INFORMATION: ABC Transporter

<400> SEQUENCE: 81

Met Ala Arg Glu Ser Glu Asn Gly Ile Val Val Lys Ala Met Gln Phe
1               5                   10                  15

Ser Tyr Glu Tyr Ser Glu Lys Glu Pro Pro Leu Phe Ile Asp Phe Asn
                20                  25                  30

Leu Asn Val Ser Pro Gly Ser Arg Cys Leu Leu Leu Gly Ala Asn Gly
            35                  40                  45

Ser Gly Lys Thr Thr Leu Leu Lys Ile Leu Ala Gly Lys His Met Val
        50                  55                  60

Gly Gly Arg Asp Val Val Arg Val Leu Asn Gly Ser Ala Phe His Asp
65                  70                  75                  80

Thr Lys Leu Val Cys Ser Gly Asp Leu Ala Tyr Leu Gly Gly Ser Trp
                85                  90                  95

Ser Lys Asn Val Ser Ser Ala Gly Asp Ile Pro Leu Gln Gly Asp Phe
                100                 105                 110

Ser Ala Glu His Met Ile Phe Gly Val Glu Gly Ala Asp Pro Asp Arg
            115                 120                 125

Arg Asp Lys Leu Ile Asp Leu Leu Asp Ile Asp Leu Asn Trp Arg Met
        130                 135                 140

His Lys Val Ser Asp Gly Gln Arg Arg Val Gln Ile Cys Leu Gly
```

```
            145                 150                 155                 160
Leu Leu His Pro Tyr Lys Val Leu Leu Asp Glu Val Thr Val Asp
                165                 170                 175

Leu Asp Val Val Thr Arg Met Asp Leu Leu Asp Phe Phe Lys Glu Glu
                180                 185                 190

Cys Glu Gln Arg Glu Ala Thr Ile Val Tyr Ala Thr His Ile Phe Asp
                195                 200                 205

Gly Leu Glu Thr Trp Ala Thr His Leu Ala Tyr Ile Gln Glu Gly Glu
    210                 215                 220

Leu Arg Arg Ala Glu Lys Ile Ser Asp Val Ser Glu Leu Lys Ser Ser
225                 230                 235                 240

Thr Asn Leu Leu Ser Ile Val Glu Ser Trp Leu Arg Ala Glu Thr Lys
                245                 250                 255

Leu Glu Lys Lys Lys Pro Val His Lys Asp Ser His Thr Gln Asn Thr
                260                 265                 270

Ser Phe Val Ser Ser Pro Phe Phe Ser Ser Arg His Met Ala Tyr Tyr
                275                 280                 285

Arg

<210> SEQ ID NO 82
<211> LENGTH: 291
<212> TYPE: PRT
<213> ORGANISM: Brassica rapa
<220> FEATURE:
<221> NAME/KEY: MISC_FEATURE
<222> LOCATION: (1)..(291)
<223> OTHER INFORMATION: ABC Transporter

<400> SEQUENCE: 82

Met Ala Ala Lys Asp Gln Ala Thr Thr Ser Asp Asp Ala Ile Arg Val
1               5                   10                  15

Ser Gly Met Glu Phe Ser Tyr Glu Ala Glu Asp Pro Ile Phe Phe Asp
                20                  25                  30

Phe Asn Leu Asp Leu Pro Ala Gly Ser Arg Cys Leu Leu Val Gly Ala
                35                  40                  45

Asn Gly Ser Gly Lys Thr Thr Leu Leu Lys Ile Leu Ala Gly Lys His
            50                  55                  60

Met Val Gly Gly Lys Asn Val Val Gln Val Leu Ser Arg Ser Ala Phe
65              70                  75                  80

His Asp Thr Gln Leu Val Cys Ser Gly Asp Leu Ser Tyr Leu Gly Gly
                85                  90                  95

Ser Trp Ser Lys Thr Val Gly Ser Ala Gly Glu Val Pro Leu Gln Gly
                100                 105                 110

Asp Phe Ser Ala Glu His Met Ile Phe Gly Val Glu Gly Ile Asp Pro
            115                 120                 125

Val Arg Arg Glu Lys Leu Ile Asp Leu Leu Asp Ile Asn Leu Gln Trp
130                 135                 140

Arg Met His Lys Val Ser Asp Gly Gln Lys Arg Val Gln Ile Cys
145                 150                 155                 160

Met Gly Leu Leu His Pro Phe Lys Val Leu Leu Leu Asp Glu Val Thr
                165                 170                 175

Val Asp Leu Asp Val Val Ala Arg Met Asp Leu Leu Glu Phe Phe Lys
                180                 185                 190

Glu Glu Cys Asp Gln Arg Gly Ala Thr Ile Val Tyr Ala Thr His Ile
                195                 200                 205
```

```
Phe Asp Gly Leu Glu Thr Trp Ala Thr His Leu Ala Tyr Ile Gln Asn
    210                 215                 220

Gly Glu Leu Asn Arg Ser Ser Lys Met Ala Asp Ile Ser Glu Met Lys
225                 230                 235                 240

Thr Ser Pro Asn Leu Leu Ser Val Val Glu Ser Trp Leu Arg Ser Glu
                245                 250                 255

Thr Lys Ile Asp Lys Lys Lys Lys Glu Pro Val Pro Ala Trp Lys
        260                 265                 270

Pro Thr Pro Phe Asp Asn Ser Pro Phe Arg Ser Ser Arg His Met Ala
            275                 280                 285

Tyr Tyr Arg
    290

<210> SEQ ID NO 83
<211> LENGTH: 302
<212> TYPE: PRT
<213> ORGANISM: Nelumbo nucifera
<220> FEATURE:
<221> NAME/KEY: MISC_FEATURE
<222> LOCATION: (1)..(302)
<223> OTHER INFORMATION: ABC Transporter

<400> SEQUENCE: 83

Met Lys Lys Gln Asn Met Val Met Gly Lys Glu Glu Leu Gln Ser Arg
1               5                   10                  15

Glu Val Glu Glu Ser Ser Cys Ile Glu Val Ser Ala Leu His Phe Ala
                20                  25                  30

Tyr Asp Gly Gln Pro Pro Leu Phe Ala Asn Phe Asn Leu Arg Ile Ser
            35                  40                  45

Arg Gly Ser Arg Cys Leu Leu Val Gly Ala Asn Gly Ser Gly Lys Thr
    50                  55                  60

Thr Leu Leu Lys Ile Leu Ala Gly Lys His Met Val Gly Gly Arg Asp
65                  70                  75                  80

Val Val Arg Val Leu Asn Cys Ser Ala Phe His Asp Thr His Leu Val
                85                  90                  95

Cys Ser Gly Asp Leu Ala Tyr Leu Gly Gly Ser Trp Ser Lys Asn Ile
            100                 105                 110

Gly Ser Ala Gly Glu Ile Pro Leu Gln Gly Asp Phe Ser Ala Glu His
    115                 120                 125

Met Ile Phe Gly Val Glu Gly Thr Asp Pro Val Arg Arg Gln Lys Leu
130                 135                 140

Ile Glu Leu Leu Asp Ile Asp Leu Gln Trp Arg Met His Lys Val Ser
145                 150                 155                 160

Asp Gly Gln Arg Arg Arg Val Gln Ile Cys Met Gly Leu Leu His Leu
                165                 170                 175

Phe Gln Val Leu Leu Leu Asp Glu Val Thr Val Asp Leu Asp Val Val
            180                 185                 190

Ala Arg Leu Asp Leu Leu Glu Phe Leu Lys Glu Cys Asp Gln Arg
    195                 200                 205

Gly Ala Thr Ile Val Tyr Ala Thr His Ile Phe Asp Gly Leu Glu Thr
    210                 215                 220

Trp Ala Thr Asp Val Ala Tyr Val Gln Asp Gly Asp Leu Lys Lys Ala
225                 230                 235                 240

Glu Lys Leu Ser Glu Leu Gln Glu Leu Lys Ser Ala Ser Asn Leu Leu
                245                 250                 255

Ser Val Val Glu Ser Trp Leu Arg Ser Glu Thr Lys Cys Glu Cys Lys
```

```
                260                 265                 270
Lys Val Leu Asn Pro Pro Ala Glu Thr Arg Lys Thr Ser Pro Phe Asp
            275                 280                 285

Asn Ser Pro Phe Arg Ser Ser Arg His Met Ala Tyr Tyr Arg
        290                 295                 300
```

<210> SEQ ID NO 84
<211> LENGTH: 292
<212> TYPE: PRT
<213> ORGANISM: Raphanus sativus
<220> FEATURE:
<221> NAME/KEY: MISC_FEATURE
<222> LOCATION: (1)..(292)
<223> OTHER INFORMATION: ABC Transporter

<400> SEQUENCE: 84

```
Met Ala Ala Lys Asp Pro Ala Thr Thr Ser Asp Asp Ala Ile Arg Val
1               5                   10                  15

Ser Gly Met Glu Phe Cys Tyr Glu Ala Asp Pro Ile Phe Phe Asp
            20                  25                  30

Phe Asn Leu Glu Leu Pro Ala Gly Ser Arg Cys Leu Leu Val Gly Ala
        35                  40                  45

Asn Gly Ser Gly Lys Thr Thr Leu Leu Lys Ile Leu Ala Gly Lys His
    50                  55                  60

Met Val Gly Gly Lys Asn Val Val Gln Val Leu Ser Arg Ser Ala Phe
65                  70                  75                  80

His Asp Thr Gln Leu Ile Cys Ser Gly Asp Leu Ser Tyr Leu Gly Gly
                85                  90                  95

Ser Trp Ser Lys Thr Val Gly Ser Ala Gly Glu Val Pro Leu Gln Gly
            100                 105                 110

Asp Phe Ser Ala Glu His Met Ile Phe Gly Val Glu Gly Ile Asp Pro
        115                 120                 125

Val Arg Arg Glu Lys Leu Ile Asp Leu Leu Asp Ile Asn Leu Gln Trp
    130                 135                 140

Arg Met His Lys Val Ser Asp Gly Gln Lys Arg Arg Val Gln Ile Cys
145                 150                 155                 160

Met Gly Leu Leu His Pro Phe Lys Val Leu Leu Leu Asp Glu Val Thr
                165                 170                 175

Val Asp Leu Asp Val Val Ala Arg Met Asp Leu Leu Glu Phe Phe Lys
            180                 185                 190

Glu Glu Cys Asp Gln Arg Gly Ala Thr Ile Val Tyr Ala Thr His Ile
        195                 200                 205

Phe Asp Gly Leu Glu Thr Trp Ala Thr His Leu Ala Tyr Ile Gln Asn
    210                 215                 220

Gly Glu Leu Asn Arg Ser Ser Lys Met Ala Asp Ile Asn Glu Met Lys
225                 230                 235                 240

Thr Ser Pro Asn Leu Leu Ser Val Val Glu Ser Trp Leu Arg Ser Glu
                245                 250                 255

Thr Lys Leu Val Lys Lys Lys Lys Lys Glu Pro Val Ala Ala Trp
            260                 265                 270

Lys Pro Ser Pro Phe Asp Asn Ser Pro Phe Arg Ser Ser Arg His Met
        275                 280                 285

Ala Tyr Tyr Arg
    290
```

<210> SEQ ID NO 85

```
<211> LENGTH: 291
<212> TYPE: PRT
<213> ORGANISM: Zostera marina
<220> FEATURE:
<221> NAME/KEY: MISC_FEATURE
<222> LOCATION: (1)..(291)
<223> OTHER INFORMATION: ABC Transporter

<400> SEQUENCE: 85

Met Lys Ser Met Val Gly Asn Gly Gly Ile Glu Val Ser Cys Met Gln
1               5                   10                  15

Phe Gly Tyr Asp Gly Ser His Thr Pro Leu Phe Ala Lys Phe Asp Leu
            20                  25                  30

Gln Ile Pro Pro Gly Ser Arg Cys Leu Leu Val Gly Ala Asn Gly Ser
        35                  40                  45

Gly Lys Thr Thr Leu Leu Lys Ile Leu Ala Gly Lys His Met Val Gly
    50                  55                  60

Gly Gln Asp Val Val Lys Ile Leu Asp Ser Ser Ala Phe His Asp Thr
65                  70                  75                  80

Gln Leu Val Cys Ser Gly Asp Leu Ala Tyr Leu Gly His Ser Trp Ser
                85                  90                  95

Arg Ser Ile Gly Ala Ala Gly Asp Val Pro Leu Gln Gly Asp Phe Ser
            100                 105                 110

Ala Glu His Met Ile Phe Gly Val Gln Gly Ile Asp Asn Ser Arg Arg
        115                 120                 125

Glu Lys Leu Ile Asp Leu Leu Asp Ile Asp Leu Gln Trp Arg Met His
    130                 135                 140

Asn Val Ser Asp Gly Gln Arg Arg Val Gln Ile Cys Leu Gly Leu
145                 150                 155                 160

Leu His Pro Tyr Lys Val Leu Leu Asp Glu Val Thr Val Asp Leu
            165                 170                 175

Asp Val Val Thr Arg Met Asp Leu Leu Gly Phe Leu Lys Glu Glu Cys
        180                 185                 190

Glu Glu Arg Gly Ala Ile Ile Val Tyr Ala Thr His Ile Phe Asp Gly
    195                 200                 205

Leu Glu Thr Trp Ala Ser Asp Val Ala Tyr Ile Gln Gln Gly Val Leu
210                 215                 220

Lys Lys Cys Ala Lys Met Ser Gln Ile His Glu Leu Gly Thr Cys Lys
225                 230                 235                 240

Asn Leu Leu Ser Val Val Glu Ser Trp Leu Arg Ala Glu Thr Lys Ile
            245                 250                 255

Leu Lys Lys Glu Glu Ser Ser Thr Val Val His Leu Gln Leu Gln Thr
        260                 265                 270

Pro Thr Val Val Ala Pro Ser Pro Phe Arg Ala Ser Arg His Met Ala
    275                 280                 285

Tyr Tyr Arg
    290

<210> SEQ ID NO 86
<211> LENGTH: 299
<212> TYPE: PRT
<213> ORGANISM: Cajanus cajan
<220> FEATURE:
<221> NAME/KEY: MISC_FEATURE
<222> LOCATION: (1)..(299)
<223> OTHER INFORMATION: ABC Transporter

<400> SEQUENCE: 86
```

Met Asn Lys Ser Leu Ser Asn Gly Gly Cys Thr Arg Thr Leu Thr Thr
1               5                   10                  15

Met Ala Pro Glu Gln Glu Asp Ser Arg Gly Ile Arg Val Asn Ala Met
            20                  25                  30

Gln Phe Ser Tyr Asp Val Gln Gln Pro Pro Leu Phe Leu Asp Phe Ser
        35                  40                  45

Leu Asp Val Glu Pro Gly Ser Arg Cys Leu Leu Val Gly Ala Asn Gly
    50                  55                  60

Ser Gly Lys Thr Thr Leu Leu Lys Ile Leu Ala Gly Lys His Met Val
65                  70                  75                  80

Gly Gly Arg Asp Val Val Arg Val Leu Asn Gly Ser Ala Phe His Asp
            85                  90                  95

Thr Gln Leu Val Cys Ser Gly Asp Leu Ala Tyr Leu Gly Gly Ser Trp
        100                 105                 110

Ser Lys Asn Val Gly Ser Ala Gly Glu Ile Pro Leu Gln Gly Asp Phe
    115                 120                 125

Ser Ala Glu His Met Ile Phe Gly Val Glu Gly Ala Asp Pro Asp Arg
130                 135                 140

Arg Asp Lys Leu Ile Asp Leu Leu Asp Ile Asp Leu Gln Trp Arg Met
145                 150                 155                 160

His Lys Val Ser Asp Gly Gln Arg Arg Val Gln Ile Cys Leu Gly
            165                 170                 175

Leu Leu Tyr Pro Tyr Lys Val Leu Leu Leu Asp Glu Val Thr Val Asp
        180                 185                 190

Leu Asp Val Val Thr Arg Met Asp Leu Leu Asp Phe Phe Arg Glu Glu
    195                 200                 205

Cys Glu Gln Arg Glu Ala Thr Ile Val Tyr Ala Thr His Ile Phe Asp
210                 215                 220

Gly Leu Glu Thr Trp Ala Thr His Leu Ala Tyr Ile Gln Asp Gly Glu
225                 230                 235                 240

Leu Arg Arg Ala Glu Lys Leu Ser Asp Val Asn Glu Leu Lys Ser Thr
            245                 250                 255

Thr Asn Leu Leu Ser Val Val Glu Ser Trp Leu Arg Ala Glu Thr Lys
        260                 265                 270

Leu Glu Lys Lys Asn Pro Val Gln Lys Thr Ser Phe Ala Ser Ser Pro
    275                 280                 285

Phe Phe Ser Ser Arg His Met Ala Tyr Tyr Arg
290                 295

<210> SEQ ID NO 87
<211> LENGTH: 305
<212> TYPE: PRT
<213> ORGANISM: Eucalyptus grandis
<220> FEATURE:
<221> NAME/KEY: MISC_FEATURE
<222> LOCATION: (1)..(305)
<223> OTHER INFORMATION: ABC Transporter

<400> SEQUENCE: 87

Met Val Gly Val Gly Asp Val Ala Lys Pro Arg Gly Glu Ala Gly Gly
1               5                   10                  15

Gly Asp Gly Asp Gly Gly Glu Arg Asp Ser Val Arg Val Cys Gly Met
            20                  25                  30

Gln Phe Ala Tyr Glu Gly Gln Pro Pro Leu Phe Leu Asp Phe Asn Leu
        35                  40                  45

Ser Val Ser Pro Gly Ser Arg Cys Leu Leu Leu Gly Ala Asn Gly Ser

```
                    50                  55                  60

Gly Lys Thr Thr Leu Leu Lys Ile Leu Ala Gly Lys Asn Met Val Gly
 65                  70                  75                  80

Gly Gln Asn Val Val Arg Val Leu Asn Arg Ser Ala Phe His Asn Thr
                     85                  90                  95

Gln Leu Val Cys Ser Gly Asp Leu Ala Tyr Leu Gly Gly Ser Trp Ser
                100                 105                 110

Lys Thr Val Gly Ser Ala Gly Glu Ile Pro Leu Gln Gly Asp Phe Ser
            115                 120                 125

Ala Glu His Met Ile Phe Gly Val Glu Gly Ala Asp Pro Val Arg Arg
        130                 135                 140

Glu Lys Leu Ile Glu Leu Leu Asp Ile Asp Leu Gln Trp Arg Met His
145                 150                 155                 160

Lys Val Ser Asp Gly Gln Arg Arg Val Gln Ile Cys Met Gly Leu
                165                 170                 175

Leu His Pro Phe Gln Val Leu Leu Asp Glu Val Thr Val Asp Leu
                180                 185                 190

Asp Val Val Thr Arg Met Asp Phe Leu Asp Phe Leu Arg Glu Glu Cys
            195                 200                 205

Asp Gln Arg Gly Ala Ala Ile Val Tyr Ala Thr His Ile Phe Asp Gly
        210                 215                 220

Leu Glu Thr Trp Ala Thr His Leu Val Tyr Ile Gln Asp Gly Glu Leu
225                 230                 235                 240

Arg Arg Ala Glu Arg Leu Thr Glu Val Asp Asp Leu Lys Ser Ser Ala
                245                 250                 255

Asn Leu His Ser Val Val Glu Ala Trp Leu Arg Ser Glu Thr Lys Arg
                260                 265                 270

Glu Lys Lys Lys Pro Val Thr Thr Ser Ser Gln Pro Gln Arg Thr Ser
            275                 280                 285

Leu Ser Gly Ala Ser Pro Phe Thr Ser Ser Arg His Met Ala Tyr Tyr
        290                 295                 300

Arg
305

<210> SEQ ID NO 88
<211> LENGTH: 291
<212> TYPE: PRT
<213> ORGANISM: Brassica oleracea
<220> FEATURE:
<221> NAME/KEY: MISC_FEATURE
<222> LOCATION: (1)..(291)
<223> OTHER INFORMATION: ABC Transporter

<400> SEQUENCE: 88

Met Ala Ala Lys Asp Gln Ala Thr Thr Ser Asp Asp Ala Ile Arg Val
  1               5                  10                  15

Ser Gly Met Glu Phe Ser Tyr Glu Ala Glu Asp Pro Ile Phe Phe Asp
                 20                  25                  30

Phe Asn Leu Asp Leu Pro Ala Gly Ser Arg Cys Leu Leu Val Gly Ala
             35                  40                  45

Asn Gly Ser Gly Lys Thr Thr Leu Leu Lys Ile Leu Ala Gly Lys His
         50                  55                  60

Met Val Gly Gly Lys Asn Val Val Gln Val Leu Ser Arg Ser Ala Phe
 65                  70                  75                  80

His Asp Thr Gln Leu Val Cys Ser Gly Asp Leu Ser Tyr Leu Gly Gly
                 85                  90                  95
```

```
Ser Trp Ser Lys Thr Ile Gly Ser Ala Gly Glu Val Pro Leu Gln Gly
            100                 105                 110

Asp Phe Ser Ala Glu His Met Ile Phe Gly Val Glu Gly Ile Asp Pro
            115                 120                 125

Val Arg Arg Asp Lys Leu Ile Asp Leu Leu Asp Ile Asn Leu Gln Trp
            130                 135                 140

Arg Met His Lys Val Ser Asp Gly Gln Lys Arg Arg Val Gln Ile Cys
145                 150                 155                 160

Met Gly Leu Leu His Pro Phe Lys Val Leu Leu Asp Glu Val Thr
                165                 170                 175

Val Asp Leu Asp Val Val Ala Arg Met Asp Leu Leu Glu Phe Phe Lys
            180                 185                 190

Glu Glu Cys Asp Gln Arg Gly Ala Thr Ile Val Tyr Ala Thr His Ile
            195                 200                 205

Phe Asp Gly Leu Glu Thr Trp Ala Thr His Leu Ala Tyr Ile Gln Asn
            210                 215                 220

Gly Glu Leu Asn Arg Ser Ser Lys Met Ala Asp Ile Ser Glu Met Lys
225                 230                 235                 240

Thr Ser Pro Asn Leu Leu Ser Val Val Glu Ser Trp Leu Arg Ser Glu
                245                 250                 255

Thr Lys Ile Tyr Lys Lys Lys Lys Glu Pro Val Ala Ala Trp Lys
            260                 265                 270

Pro Thr Pro Phe Asp Asn Ser Pro Phe Arg Ser Ser Arg His Met Ala
            275                 280                 285

Tyr Tyr Arg
            290

<210> SEQ ID NO 89
<211> LENGTH: 288
<212> TYPE: PRT
<213> ORGANISM: Erythranthe guttata
<220> FEATURE:
<221> NAME/KEY: MISC_FEATURE
<222> LOCATION: (1)..(288)
<223> OTHER INFORMATION: ABC Transporter

<400> SEQUENCE: 89

Met Gly Glu Glu Ser His Ser Ile Gln Val Ser Gly Met Gln Phe Ser
1               5                   10                  15

Tyr Asp Ala Ile Arg Ser Pro Leu Phe Phe Asp Phe Asn Leu Asp Ile
            20                  25                  30

Ser Pro Arg Ser Arg Cys Leu Leu Val Gly Ala Asn Gly Ser Gly Lys
            35                  40                  45

Thr Thr Leu Leu Arg Ile Leu Ala Gly Lys His Met Val Gly Gly Arg
        50                  55                  60

Asp Val Val Arg Val Leu Asn Cys Ser Ala Phe His Asp Thr Ser Leu
65                  70                  75                  80

Val Cys Asn Gly Asp Leu Ala Tyr Leu Gly Glu Ser Trp Ser Lys Thr
                85                  90                  95

Val Gly Ser Ala Gly Glu Leu Pro Leu Gln Gly Asp Phe Ser Ala Glu
            100                 105                 110

His Met Ile Phe Gly Val Glu Gly Val Asp Pro Val Arg Arg Asp Lys
            115                 120                 125

Leu Ile Glu Leu Leu Asp Ile Asp Leu Arg Trp Arg Met His Lys Val
            130                 135                 140
```

Ser Asp Gly Gln Arg Arg Val Gln Ile Cys Met Gly Leu Leu His
145                 150                 155                 160

Pro Tyr Lys Val Leu Leu Asp Glu Val Thr Val Asp Leu Asp Val
            165                 170                 175

Val Ala Arg Met Asp Leu Leu Glu Phe Phe Lys Glu Glu Cys Glu Gln
            180                 185                 190

Arg Gly Ala Thr Ile Val Tyr Ala Thr His Ile Phe Asp Gly Leu Glu
            195                 200                 205

Thr Trp Ala Thr Asp Leu Val Tyr Val Gln Asp Gly Val Leu Asn Lys
210                 215                 220

Ser Gln Lys Leu Ser Asp Leu Asn Glu Leu Lys Asn Asn Leu Asn Leu
225                 230                 235                 240

Leu Ser Val Val Glu Ser Trp Leu Arg Ser Glu Thr Lys Ile Glu Lys
            245                 250                 255

Lys Lys Thr Gln Val Asn Ser Thr Pro Gln Pro Lys Lys Ser Ser Pro
            260                 265                 270

Phe Asp Ser Ser Pro Phe Arg Ser Ser Arg His Met Ala Tyr Tyr Arg
            275                 280                 285

<210> SEQ ID NO 90
<211> LENGTH: 282
<212> TYPE: PRT
<213> ORGANISM: Vigna radiata
<220> FEATURE:
<221> NAME/KEY: MISC_FEATURE
<222> LOCATION: (1)..(282)
<223> OTHER INFORMATION: ABC Transporter

<400> SEQUENCE: 90

Met Ala Ala Ala Glu Glu Asp Ser Pro Gly Ile Arg Val Ser Gly Met
1               5                   10                  15

Gln Phe Ser Tyr Glu Ala Gln Gln Pro Pro Leu Phe Leu Asp Phe Asn
            20                  25                  30

Leu Asn Val Lys Pro Gly Ser Arg Cys Leu Leu Val Gly Ala Asn Gly
            35                  40                  45

Ser Gly Lys Thr Thr Leu Leu Lys Ile Leu Ala Gly Lys His Met Val
50                  55                  60

Gly Gly Arg Asp Val Val Arg Val Leu Asn Gly Ser Ala Phe His Asp
65                  70                  75                  80

Thr Gln Leu Val Cys Ser Gly Asp Leu Ala Tyr Leu Gly Gly Ser Trp
            85                  90                  95

Ser Lys Asn Val Gly Ser Ala Gly Glu Ile Pro Leu Gln Gly Asp Phe
            100                 105                 110

Ser Ala Glu His Met Ile Phe Gly Val Glu Gly Ala Asp Pro Asp Arg
            115                 120                 125

Arg Asp Lys Leu Ile Glu Leu Leu Asp Ile Asp Leu Gln Trp Arg Met
            130                 135                 140

His Lys Val Ser Asp Gly Gln Arg Arg Val Gln Ile Cys Leu Gly
145                 150                 155                 160

Leu Leu Tyr Pro Tyr Lys Val Leu Leu Asp Glu Val Thr Val Asp
            165                 170                 175

Leu Asp Val Val Thr Arg Met Asp Leu Leu Glu Phe Phe Arg Glu Glu
            180                 185                 190

Cys Glu Gln Arg Glu Ala Thr Ile Val Tyr Ala Thr His Ile Phe Asp
            195                 200                 205

Gly Leu Glu Ala Trp Ala Thr His Leu Ala Tyr Ile Gln Asp Gly Glu

```
                210             215             220
Leu Arg Arg Ala Glu Lys Ile Ser Asp Val Asn Glu Leu Lys Ser Ser
225                 230                 235                 240

Thr Asn Leu Leu Ser Val Val Glu Thr Trp Leu Arg Ala Glu Thr Lys
                245                 250                 255

Val Val Lys Lys Lys Pro Val Gln Lys Asn Phe Ala Ser Ser Pro Phe
                260                 265                 270

Phe Ser Ser Arg His Met Ala Tyr Tyr Arg
                275                 280

<210> SEQ ID NO 91
<211> LENGTH: 286
<212> TYPE: PRT
<213> ORGANISM: Capsicum annuum
<220> FEATURE:
<221> NAME/KEY: MISC_FEATURE
<222> LOCATION: (1)..(286)
<223> OTHER INFORMATION: ABC Transporter

<400> SEQUENCE: 91

Met Glu Gly Glu Ser Ser Ile Arg Val Asn Gly Met Gln Phe Ser
1               5                   10                  15

Tyr Asp Phe Gln Ser Pro Ile Phe Phe Asp Phe Asn Leu Asn Ile Ser
                20                  25                  30

Pro Arg Ser Arg Cys Leu Leu Leu Gly Ala Asn Gly Ser Gly Lys Thr
                35                  40                  45

Thr Leu Leu Lys Ile Leu Ala Gly Lys His Met Val Gly Gly Lys Glu
        50                  55                  60

Val Val Arg Val Leu Asn Phe Ser Ala Phe His Asp Thr His Leu Val
65                  70                  75                  80

Cys Ser Gly Asp Leu Ala Tyr Leu Gly Glu Ser Trp Ser Lys Thr Val
                85                  90                  95

Gly Thr Val Gly Glu Val Pro Leu Gln Gly Asp Phe Ser Ala Glu His
                100                 105                 110

Met Ile Phe Gly Val Glu Gly Val Asp Pro Val Arg Arg Glu Lys Leu
                115                 120                 125

Ile Glu Leu Leu Asp Ile Asp Leu Gln Trp Arg Met His Lys Val Ser
            130                 135                 140

Asp Gly Gln Arg Arg Val Gln Ile Cys Met Gly Leu Leu His Pro
145                 150                 155                 160

Tyr Lys Val Leu Leu Leu Asp Glu Val Thr Val Asp Leu Asp Val Val
                165                 170                 175

Ala Arg Met Asp Leu Leu Asp Phe Phe Lys Glu Glu Cys Glu Gln Arg
                180                 185                 190

Gly Ala Thr Ile Val Tyr Ala Thr His Ile Phe Asp Gly Leu Glu Thr
                195                 200                 205

Trp Ala Thr Asp Leu Val Tyr Ile Gln Asp Gly Val Leu Lys Arg Ser
                210                 215                 220

Glu Lys Leu Pro Glu Leu Pro Glu Leu Lys Ser Ala Pro Asn Leu Leu
225                 230                 235                 240

Ser Val Val Glu Asn Trp Leu Arg Ser Glu Thr Thr Ile Glu Lys Lys
                245                 250                 255

Lys Pro Leu Pro Ala Pro Pro Lys Val Gln Lys Ser Ser Pro Phe Val
                260                 265                 270

Ser Ser Pro Phe Gln Ser Ser Arg His Met Ala Tyr Phe Arg
                275                 280                 285
```

<210> SEQ ID NO 92
<211> LENGTH: 286
<212> TYPE: PRT
<213> ORGANISM: Solanum pennellii
<220> FEATURE:
<221> NAME/KEY: MISC_FEATURE
<222> LOCATION: (1)..(286)
<223> OTHER INFORMATION: ABC Transporter

<400> SEQUENCE: 92

Met Ala Gly Glu Ser Ser Ile Gln Val Asn Gly Met Gln Phe Ser
1               5                   10                  15

Tyr Asp Phe Gln Ser Pro Ile Tyr Phe Asp Phe Asn Leu Ser Val Ala
            20                  25                  30

Pro Arg Ser Arg Cys Leu Leu Leu Gly Ala Asn Gly Ser Gly Lys Thr
            35                  40                  45

Thr Leu Leu Lys Ile Leu Ala Gly Lys His Met Val Gly Gly Lys Asp
        50                  55                  60

Val Val Arg Val Leu Asn Leu Ser Ala Phe His Asp Thr His Leu Val
65                  70                  75                  80

Cys Ser Gly Asp Leu Ala Tyr Leu Gly Glu Ser Trp Ser Lys Asn Val
                85                  90                  95

Gly Ala Val Gly Asp Ile Pro Leu Gln Gly Asp Phe Ser Ala Glu His
            100                 105                 110

Met Ile Phe Gly Val Glu Gly Val Asp Pro Val Arg Arg Glu Lys Leu
        115                 120                 125

Ile Glu Leu Leu Asp Ile Asp Leu Gln Trp Arg Met His Lys Val Ser
130                 135                 140

Asp Gly Gln Arg Arg Val Gln Ile Cys Met Gly Leu Leu His Pro
145                 150                 155                 160

Tyr Lys Val Leu Leu Met Asp Glu Val Thr Val Asp Leu Asp Val Val
                165                 170                 175

Ala Arg Met Asp Leu Leu Asp Phe Phe Lys Glu Glu Cys Glu Gln Arg
            180                 185                 190

Gly Ala Thr Ile Val Tyr Ala Thr His Ile Phe Asp Gly Leu Glu Thr
        195                 200                 205

Trp Ala Thr Asp Leu Val Tyr Ile Gln Glu Gly Val Leu Lys Arg Thr
210                 215                 220

Glu Lys Leu Pro Glu Leu Pro Glu Leu Lys Ser Ser Pro Asn Leu Leu
225                 230                 235                 240

Ser Val Val Glu Asn Trp Leu Arg Ser Glu Thr Pro Ile Glu Lys Lys
                245                 250                 255

Lys Pro Ala Pro Ala Pro Ala Lys Ala Gln Lys Ser Ser Pro Phe Gly
            260                 265                 270

Ser Ser Pro Phe Gln Ser Ser Arg His Met Ser His Tyr Arg
        275                 280                 285

<210> SEQ ID NO 93
<211> LENGTH: 286
<212> TYPE: PRT
<213> ORGANISM: Solanum lycopersicum
<220> FEATURE:
<221> NAME/KEY: MISC_FEATURE
<222> LOCATION: (1)..(286)
<223> OTHER INFORMATION: ABC Transporter

<400> SEQUENCE: 93

```
Met Ala Gly Glu Ser Ser Ile Gln Val Asn Gly Met Gln Phe Ser
1               5                   10                  15

Tyr Asp Phe Gln Ser Pro Ile Tyr Phe Asp Phe Asn Leu Asn Val Ala
            20                  25                  30

Pro Arg Ser Arg Cys Leu Leu Leu Gly Ala Asn Gly Ser Gly Lys Thr
        35                  40                  45

Thr Leu Leu Lys Ile Leu Ala Gly Lys His Met Val Gly Gly Lys Asp
50                  55                  60

Val Val Arg Val Leu Asn Leu Ser Ala Phe His Asp Thr His Leu Val
65                  70                  75                  80

Cys Ser Gly Asp Leu Ala Tyr Leu Gly Glu Ser Trp Ser Lys Asn Val
                85                  90                  95

Gly Ala Val Gly Asp Ile Pro Leu Gln Gly Asp Phe Ser Ala Glu His
            100                 105                 110

Met Ile Phe Gly Val Glu Gly Val Asp Pro Val Arg Arg Glu Lys Leu
        115                 120                 125

Ile Glu Leu Leu Asp Ile Asp Leu Gln Trp Arg Met His Lys Val Ser
130                 135                 140

Asp Gly Gln Arg Arg Arg Val Gln Ile Cys Met Gly Leu Leu His Pro
145                 150                 155                 160

Tyr Lys Val Leu Leu Met Asp Glu Val Thr Val Asp Leu Asp Val Val
                165                 170                 175

Ala Arg Met Asp Leu Leu Asp Phe Phe Lys Glu Glu Cys Glu Gln Arg
            180                 185                 190

Gly Ala Thr Ile Val Tyr Ala Thr His Ile Phe Asp Gly Leu Glu Thr
        195                 200                 205

Trp Ala Thr Asp Leu Val Tyr Ile Gln Glu Gly Val Leu Lys Arg Thr
210                 215                 220

Glu Lys Leu Pro Glu Leu Pro Glu Leu Lys Ser Ser Pro Asn Leu Leu
225                 230                 235                 240

Ser Val Val Glu Asn Trp Leu Arg Ser Glu Thr Pro Ile Glu Lys Lys
                245                 250                 255

Lys Pro Ala Pro Ala Pro Ala Lys Ala Gln Lys Ser Ser Pro Phe Gly
            260                 265                 270

Ser Ser Pro Phe Gln Ser Ser Arg His Met Ser His Tyr Arg
        275                 280                 285

<210> SEQ ID NO 94
<211> LENGTH: 260
<212> TYPE: PRT
<213> ORGANISM: Sesamum indicum
<220> FEATURE:
<221> NAME/KEY: MISC_FEATURE
<222> LOCATION: (1)..(260)
<223> OTHER INFORMATION: ABC Transporter

<400> SEQUENCE: 94

Met Ser Leu Asn Ile Tyr Pro Gly Ser Arg Cys Leu Leu Val Gly Ala
1               5                   10                  15

Asn Gly Ser Gly Lys Thr Thr Leu Leu Arg Ile Leu Ala Gly Lys His
            20                  25                  30

Met Val Gly Gly Arg Asp Val Arg Val Leu Asn Cys Ser Ala Phe
        35                  40                  45

His Asp Thr Ser Leu Val Cys Ser Gly Asp Leu Ala Tyr Leu Gly Glu
50                  55                  60

Ser Trp Ser Lys Thr Val Gly Ser Ala Gly Glu Leu Pro Leu Gln Gly
```

```
                65                  70                  75                  80
Asp Phe Ser Ala Glu His Met Ile Phe Gly Val Glu Gly Val Asp Pro
                    85                  90                  95

Val Arg Arg Asp Lys Leu Ile Glu Leu Leu Asp Ile Asp Leu His Trp
                100                 105                 110

Arg Met His Lys Val Ser Asp Gly Gln Arg Arg Val Gln Ile Cys
            115                 120                 125

Met Gly Leu Leu His Pro Tyr Lys Val Leu Leu Asp Glu Val Thr
        130                 135                 140

Val Asp Leu Asp Val Val Ala Arg Met Asp Leu Leu Glu Phe Phe Lys
145                 150                 155                 160

Glu Glu Cys Glu Gln Arg Arg Ala Thr Ile Val Tyr Ala Thr His Ile
                165                 170                 175

Phe Asp Gly Leu Glu Thr Trp Ala Thr Asp Leu Val Tyr Val Gln Glu
                180                 185                 190

Gly Val Leu Lys Arg Ser Asp Lys Leu Ala Asp Leu Lys Glu Leu Lys
                195                 200                 205

Asn Asn Met Asn Leu Leu Ser Val Val Glu Ser Trp Leu Arg Thr Glu
        210                 215                 220

Thr Lys Ile Glu Lys Lys Pro Val Asn Ser Pro Ser Pro Leu Gln
225                 230                 235                 240

Lys Ser Ser Pro Phe Asp Asn Ser Pro Phe Arg Ser Ser Arg His Met
                245                 250                 255

Ala Tyr Tyr Arg
            260

<210> SEQ ID NO 95
<211> LENGTH: 286
<212> TYPE: PRT
<213> ORGANISM: Solanum tuberosum
<220> FEATURE:
<221> NAME/KEY: MISC_FEATURE
<222> LOCATION: (1)..(286)
<223> OTHER INFORMATION: ABC Transporter

<400> SEQUENCE: 95

Met Glu Gly Glu Ser Ser Ile Gln Val Asn Gly Met Gln Phe Ser
1               5                   10                  15

Tyr Asp Phe Gln Ser Pro Ile Tyr Phe Asp Phe Asn Leu Asn Ile Ala
                20                  25                  30

Pro Arg Ser Arg Cys Leu Leu Leu Gly Ala Asn Gly Ser Gly Lys Thr
            35                  40                  45

Thr Leu Leu Lys Ile Leu Ala Gly Lys His Met Val Gly Gly Lys Asp
        50                  55                  60

Val Val Arg Val Leu Asn Phe Ser Ala Phe His Asp Thr His Leu Val
65                  70                  75                  80

Cys Ser Gly Asp Leu Ala Tyr Leu Gly Glu Ser Trp Ser Lys Asn Val
                85                  90                  95

Gly Ala Val Gly Glu Ile Pro Leu Gln Gly Asp Phe Ser Ala Glu His
                100                 105                 110

Met Ile Phe Gly Val Glu Gly Val Asp Pro Val Arg Arg Glu Lys Leu
            115                 120                 125

Ile Glu Leu Leu Asp Ile Asp Leu Gln Trp Arg Met His Lys Val Ser
        130                 135                 140

Asp Gly Gln Arg Arg Val Gln Ile Cys Met Gly Leu Leu His Pro
145                 150                 155                 160
```

```
Tyr Lys Val Leu Leu Leu Asp Glu Val Thr Val Asp Leu Asp Val Val
                165                 170                 175

Ala Arg Met Asp Leu Leu Asp Phe Phe Lys Glu Glu Cys Glu Gln Arg
            180                 185                 190

Gly Ala Thr Ile Val Tyr Ala Thr His Ile Phe Asp Gly Leu Glu Thr
            195                 200                 205

Trp Ala Thr Asp Leu Val Tyr Ile Gln Glu Gly Val Leu Lys Arg Thr
210                 215                 220

Glu Lys Leu Pro Glu Leu Pro Glu Leu Lys Ser Ser Pro Asn Leu Leu
225                 230                 235                 240

Ser Val Val Glu Asn Trp Leu Arg Ser Glu Thr Pro Ile Glu Lys Lys
            245                 250                 255

Lys Pro Ala Pro Ser Pro Pro Lys Ala Gln Lys Ser Ser Pro Phe Gly
            260                 265                 270

Ser Ser Pro Phe Gln Ser Ser Arg His Met Ala Tyr Phe Arg
            275                 280                 285

<210> SEQ ID NO 96
<211> LENGTH: 291
<212> TYPE: PRT
<213> ORGANISM: Camelina sativa
<220> FEATURE:
<221> NAME/KEY: MISC_FEATURE
<222> LOCATION: (1)..(291)
<223> OTHER INFORMATION: ABC Transporter

<400> SEQUENCE: 96

Met Ala Glu Glu Lys Asp Ala Thr Ala Ser Gly Asp Asp Ala Ile Lys
1               5                   10                  15

Val Ser Gly Met Gln Phe Ala Tyr Glu Val Glu Asp Pro Ile Phe Phe
            20                  25                  30

Asp Phe Asn Leu Asp Leu Pro Ala Gly Ser Arg Cys Leu Leu Val Gly
            35                  40                  45

Ala Asn Gly Ser Gly Lys Thr Thr Leu Leu Lys Ile Leu Ala Gly Lys
50                  55                  60

His Met Val Gly Gly Lys Asn Val Val Gln Val Leu Ser Arg Ser Ala
65                  70                  75                  80

Phe His Asp Thr Gln Leu Val Cys Ser Gly Asp Leu Ser Tyr Leu Gly
            85                  90                  95

Gly Ser Trp Ser Lys Thr Val Gly Ser Ala Gly Glu Val Pro Leu Gln
            100                 105                 110

Gly Asp Phe Ser Ala Glu His Met Ile Phe Gly Val Glu Gly Ile Asp
            115                 120                 125

Pro Val Arg Arg Glu Lys Leu Ile Asp Leu Leu Asp Ile Asn Leu Gln
130                 135                 140

Trp Arg Met His Lys Val Ser Asp Gly Gln Lys Arg Arg Val Gln Ile
145                 150                 155                 160

Cys Met Gly Leu Leu His Pro Phe Lys Val Leu Leu Leu Asp Glu Val
            165                 170                 175

Thr Val Asp Leu Asp Val Val Ala Arg Met Asp Leu Leu Lys Phe Phe
            180                 185                 190

Val Glu Glu Cys Asp Gln Arg Gly Ala Thr Ile Val Tyr Ala Thr His
            195                 200                 205

Ile Phe Asp Gly Leu Glu Thr Trp Ala Thr His Leu Ala Tyr Ile Gln
210                 215                 220
```

```
Asp Gly Glu Leu Asn Gly Leu Ser Lys Met Ala Asp Ile Glu Glu Leu
225                 230                 235                 240

Lys Ser Ala Pro Asn Leu Leu Ser Val Val Glu Ser Trp Leu Arg Ser
            245                 250                 255

Glu Ile Lys Val Val Lys Lys Lys Lys Pro Val Ala Ala Trp Lys
                260                 265                 270

Pro Ser Pro Leu Asp Asn Ser Pro Phe Arg Ser Ser Arg His Met Ala
            275                 280                 285

Tyr Tyr Arg
    290

<210> SEQ ID NO 97
<211> LENGTH: 290
<212> TYPE: PRT
<213> ORGANISM: Arabidopsis thaliana
<220> FEATURE:
<221> NAME/KEY: MISC_FEATURE
<222> LOCATION: (1)..(290)
<223> OTHER INFORMATION: ABC Transporter

<400> SEQUENCE: 97

Met Ala Glu Lys Asp Ala Thr Ala Ser Gly Asp Ala Ile Arg Val
1               5                   10                  15

Ser Gly Met Gln Phe Ala Tyr Glu Val Glu Asp Pro Ile Phe Phe Asp
            20                  25                  30

Phe Asn Leu Asp Leu Pro Ala Gly Ser Arg Cys Leu Val Gly Ala
            35                  40                  45

Asn Gly Ser Gly Lys Thr Thr Leu Leu Lys Ile Leu Ala Gly Lys His
50                  55                  60

Met Val Gly Gly Lys Asn Val Val Gln Val Leu Ser Arg Ser Ala Phe
65                  70                  75                  80

His Asp Thr Gln Leu Val Cys Ser Gly Asp Leu Ser Tyr Leu Gly Gly
                85                  90                  95

Ser Trp Ser Lys Thr Val Gly Ser Ala Gly Glu Val Pro Leu Gln Gly
            100                 105                 110

Asp Phe Ser Ala Glu His Met Ile Phe Gly Val Glu Gly Thr Asp Pro
            115                 120                 125

Val Arg Arg Glu Lys Leu Ile Asp Leu Leu Asp Ile Asn Leu Gln Trp
130                 135                 140

Arg Met His Lys Val Ser Asp Gly Gln Lys Arg Arg Val Gln Ile Cys
145                 150                 155                 160

Met Gly Leu Leu His Pro Phe Lys Val Leu Leu Leu Asp Glu Val Thr
                165                 170                 175

Val Asp Leu Asp Val Val Ala Arg Met Asp Leu Leu Glu Phe Phe Lys
            180                 185                 190

Glu Glu Cys Asp Gln Arg Gly Ala Thr Ile Val Tyr Ala Thr His Ile
            195                 200                 205

Phe Asp Gly Leu Glu Thr Trp Ala Thr His Leu Ala Tyr Ile Gln Asp
            210                 215                 220

Gly Glu Leu Asn Arg Leu Ser Lys Met Thr Asp Ile Glu Glu Leu Lys
225                 230                 235                 240

Thr Ser Pro Asn Leu Leu Ser Val Val Glu Ser Trp Leu Arg Ser Glu
                245                 250                 255

Ile Lys Leu Val Lys Lys Lys Lys Pro Val Ala Pro Trp Lys Pro
            260                 265                 270

Ser Pro Phe Asp Asn Ser Pro Phe Arg Ser Ser Arg His Met Ala Tyr
```

Tyr Arg
    290

<210> SEQ ID NO 98
<211> LENGTH: 306
<212> TYPE: PRT
<213> ORGANISM: Cucumis sativus
<220> FEATURE:
<221> NAME/KEY: MISC_FEATURE
<222> LOCATION: (1)..(306)
<223> OTHER INFORMATION: ABC Transporter

<400> SEQUENCE: 98

Met Ala Asp Asn Gly Ile Ser Ile Ala Gly Asn Asp Gly Ile Glu Val
1               5                   10                  15

Leu Asp Glu Lys Gly Ser Thr Ser Ile Lys Val Gln Ala Met Gln Phe
            20                  25                  30

Ser Tyr Glu Ser Asp Ser Pro Leu Phe Val Glu Phe Asn Leu Gln Val
        35                  40                  45

Gly Ser Gly Ser Arg Cys Leu Leu Val Gly Ala Asn Gly Ser Gly Lys
    50                  55                  60

Thr Thr Leu Leu Lys Ile Leu Ala Gly Lys His Met Val Gly Gly Arg
65                  70                  75                  80

Asp Val Val Gln Val Leu Asn Gly Ser Ala Phe His Asp Thr Gln Leu
                85                  90                  95

Val Cys Ser Gly Asp Leu Ala Tyr Leu Gly Gly Ser Trp Ser Arg Thr
            100                 105                 110

Ile Ser Cys Ala Gly Glu Val Ala Leu Gln Gly Asp Phe Ser Ala Glu
        115                 120                 125

His Met Ile Phe Gly Val Glu Gly Thr Asp Pro Glu Arg Arg Asp Arg
    130                 135                 140

Leu Ile Asp Leu Leu Asp Ile Asp Leu Arg Trp Arg Met His Lys Val
145                 150                 155                 160

Ser Asp Gly Gln Arg Arg Val Gln Ile Cys Met Gly Leu Leu His
                165                 170                 175

Pro Phe Lys Val Leu Leu Leu Asp Glu Val Thr Val Asp Leu Asp Val
            180                 185                 190

Val Ala Arg Met Asp Leu Leu Asp Phe Leu Lys Glu Glu Cys Asp Gln
        195                 200                 205

Arg Gly Ala Thr Ile Val Tyr Ala Thr His Ile Phe Asp Gly Leu Glu
    210                 215                 220

Thr Trp Ala Thr His Leu Ala Tyr Ile Gln Asp Gly Glu Leu Arg Lys
225                 230                 235                 240

Ser Glu Lys Leu Ser Lys Val Glu Glu Leu Lys Thr Cys Ala Asn Leu
                245                 250                 255

Leu Ser Val Val Glu Thr Trp Leu Arg Ala Glu Thr Lys Leu Glu Lys
            260                 265                 270

Lys Lys Lys Leu Pro Ile Gln Pro Pro Ser Asn Asn Gln Lys Ile Val
        275                 280                 285

Ser Pro Phe Gly Ser Ser Pro Phe Met Ser Ser Arg His Met Ala Tyr
    290                 295                 300

Tyr Arg
305

<210> SEQ ID NO 99

-continued

```
<211> LENGTH: 289
<212> TYPE: PRT
<213> ORGANISM: Eutrema salsugineum
<220> FEATURE:
<221> NAME/KEY: MISC_FEATURE
<222> LOCATION: (1)..(289)
<223> OTHER INFORMATION: ABC Transporter

<400> SEQUENCE: 99
```

Met Ala Thr Thr Ser Gly Asp Asp Ala Ile Arg Val Ser Gly Met Glu
1               5                   10                  15

Phe Ala Tyr Glu Val Asp Asp Pro Ile Phe Asp Phe Asn Leu Asp
            20                  25                  30

Leu Pro Ala Gly Ser Arg Cys Leu Leu Val Gly Ala Asn Gly Ser Gly
        35                  40                  45

Lys Thr Thr Leu Leu Lys Ile Leu Ala Gly Lys His Met Val Gly Gly
    50                  55                  60

Lys Asn Val Val Gln Val Leu Ser Arg Ser Ala Phe His Asp Thr Gln
65                  70                  75                  80

Leu Val Cys Ser Gly Asp Leu Ser Tyr Leu Gly Ser Trp Ser Lys
            85                  90                  95

Thr Val Gly Ser Ala Gly Glu Val Pro Leu Gln Gly Asp Phe Ser Ala
            100                 105                 110

Glu His Met Ile Phe Gly Val Glu Gly Ile Asp Pro Val Arg Arg Glu
        115                 120                 125

Lys Leu Ile Asp Leu Leu Asp Ile Asn Leu His Trp Arg Met His Lys
130                 135                 140

Val Ser Asp Gly Gln Lys Arg Arg Val Gln Ile Cys Met Gly Leu Leu
145                 150                 155                 160

His Pro Phe Lys Val Leu Leu Leu Asp Glu Val Thr Val Asp Leu Asp
                165                 170                 175

Val Val Ala Arg Met Asp Leu Leu Glu Phe Phe Lys Glu Glu Cys Asp
            180                 185                 190

Lys Arg Gly Ala Thr Ile Val Tyr Ala Thr His Ile Phe Asp Gly Leu
        195                 200                 205

Glu Thr Trp Ala Thr His Leu Ala Tyr Ile Gln Asn Gly Glu Leu Ile
    210                 215                 220

Arg Ser Ser Arg Met Ala Asp Ile Asn Glu Met Lys Ile Ser Pro Asn
225                 230                 235                 240

Leu Leu Ser Val Val Glu Ser Trp Leu Arg Ser Glu Thr Lys Leu Glu
                245                 250                 255

Lys Lys Lys Lys Lys Lys Glu Pro Ala Ala Lys Trp Lys Pro Ser
            260                 265                 270

Pro Phe Asp Asn Ser Pro Phe Arg Ser Arg His Met Ala Tyr Tyr
        275                 280                 285

Arg

```
<210> SEQ ID NO 100
<211> LENGTH: 284
<212> TYPE: PRT
<213> ORGANISM: Fragaria vesca
<220> FEATURE:
<221> NAME/KEY: MISC_FEATURE
<222> LOCATION: (1)..(284)
<223> OTHER INFORMATION: ABC Transporter

<400> SEQUENCE: 100
```

Met Ala Glu Pro Gln Glu Ser Glu Ala Ser Ser Gly Ile Arg Val Ser

```
                1               5              10              15
            Gly Met Gln Phe Ala Tyr Asp Ala Gln Pro Leu Phe Tyr Asp Phe
                           20              25              30

Ser Leu Asn Val Ala Pro Gly Ser Arg Cys Leu Leu Val Gly Ala Asn
                           35              40              45

Gly Ser Gly Lys Thr Thr Leu Leu Lys Ile Leu Ala Gly Lys Gln Met
                50              55              60

Val Gly Gly Arg Asp Val Val Arg Val Leu Asn Cys Ser Ala Phe His
             65              70              75              80

Asp Thr His Leu Val Cys Ser Gly Asp Leu Ala Tyr Leu Gly Gly Ser
                           85              90              95

Trp Ser Lys Thr Val Gly Ser Ala Gly Glu Val Pro Leu Gln Gly Asp
                          100             105             110

Phe Ser Ala Glu His Met Ile Phe Gly Val Glu Gly Thr Asp Pro Val
                          115             120             125

Arg Arg Glu Lys Leu Ile Glu Leu Leu Asp Ile Asp Leu Lys Trp Arg
                          130             135             140

Met His Lys Val Ser Asp Gly Gln Arg Arg Val Gln Ile Cys Met
            145             150             155             160

Gly Leu Leu His Pro Phe Lys Val Leu Leu Leu Asp Glu Val Thr Val
                          165             170             175

Asp Leu Asp Val Val Ala Arg Met Asp Leu Leu Glu Phe Phe Lys Glu
                          180             185             190

Glu Cys Glu Gln Arg Gly Ala Thr Ile Val Tyr Ala Thr His Ile Phe
                          195             200             205

Asp Gly Leu Glu Thr Trp Ala Thr His Leu Ala Tyr Ile Gln Asp Gly
                          210             215             220

Glu Leu Lys Lys Ala Gln Lys Leu Leu Glu Val Glu Glu Leu Lys Asn
            225             230             235             240

Ser Val Asn Leu Leu Ser Val Val Glu Ser Trp Leu Arg Ala Glu Thr
                          245             250             255

Lys Gln Glu Lys Lys Lys Thr Lys Asn Pro Ala Gln Thr Ser Ser Pro
                          260             265             270

Phe Gly Met Ser Ser Arg Gln Met Ala Tyr Tyr Arg
                          275             280

<210> SEQ ID NO 101
<211> LENGTH: 290
<212> TYPE: PRT
<213> ORGANISM: Capsella rubella
<220> FEATURE:
<221> NAME/KEY: MISC_FEATURE
<222> LOCATION: (1)..(290)
<223> OTHER INFORMATION: ABC Transporter

<400> SEQUENCE: 101

Met Ala Glu Lys Asp Ala Thr Ala Ser Gly Gly Asp Ala Ile Arg Val
 1               5              10              15

Ser Gly Met Gln Phe Ala Tyr Glu Val Glu Asp Pro Ile Phe Phe Asp
                20              25              30

Phe Asn Leu Asp Leu Pro Val Gly Ser Arg Cys Leu Leu Val Gly Ala
                35              40              45

Asn Gly Ser Gly Lys Thr Thr Leu Leu Lys Ile Leu Ala Gly Lys His
            50              55              60

Met Val Gly Gly Lys Asn Val Val Gln Val Leu Ser Arg Ser Ala Phe
 65              70              75              80
```

```
His Asp Thr Gln Leu Val Cys Ser Gly Asp Leu Ser Tyr Leu Gly Gly
                85                  90                  95

Ser Trp Ser Lys Thr Val Gly Ser Ala Gly Glu Val Pro Leu Gln Gly
            100                 105                 110

Asp Phe Ser Ala Glu His Met Ile Phe Gly Val Glu Gly Ile Asp Pro
        115                 120                 125

Val Arg Arg Glu Lys Leu Ile Asp Leu Leu Asp Ile Asn Leu Gln Trp
    130                 135                 140

Arg Met His Lys Val Ser Asp Gly Gln Lys Arg Arg Val Gln Ile Cys
145                 150                 155                 160

Met Gly Leu Leu His Pro Phe Lys Val Leu Leu Leu Asp Glu Val Thr
                165                 170                 175

Val Asp Leu Asp Val Val Ala Arg Met Asp Leu Leu Glu Phe Phe Ile
            180                 185                 190

Glu Glu Cys Asp Gln Arg Gly Ala Thr Ile Val Tyr Ala Thr His Ile
        195                 200                 205

Phe Asp Gly Leu Glu Thr Trp Ala Thr His Leu Ala Tyr Ile Gln Asp
    210                 215                 220

Gly Glu Leu Asn Arg Leu Ser Lys Met Thr Asp Ile Asp Glu Leu Lys
225                 230                 235                 240

Thr Ser Pro Asn Leu Leu Ser Val Val Glu Ser Trp Leu Arg Ser Glu
                245                 250                 255

Ile Lys Leu Val Lys Lys Lys Ile Lys Pro Val Ala Ala Trp Lys
            260                 265                 270

Pro Ser Pro Phe Asp Asn Ser Pro Phe Arg Ser Arg His Met Ala
        275                 280                 285

Tyr Tyr
    290

<210> SEQ ID NO 102
<211> LENGTH: 291
<212> TYPE: PRT
<213> ORGANISM: Tarenaya hassleriana
<220> FEATURE:
<221> NAME/KEY: MISC_FEATURE
<222> LOCATION: (1)..(291)
<223> OTHER INFORMATION: ABC Transporter

<400> SEQUENCE: 102

Met Ala Glu Arg Asp Ala Ala Lys Gly Gly Gly Asp Gly Asp Asp
1               5                   10                  15

Ala Ile Arg Val Cys Gly Met Gln Phe Ala Tyr Asp Val Gln Asp Pro
            20                  25                  30

Leu Phe Phe Asp Phe Asn Leu Glu Leu Pro Ala Gly Ser Arg Cys Leu
        35                  40                  45

Leu Val Gly Ala Asn Gly Ser Gly Lys Thr Thr Leu Leu Lys Ile Leu
    50                  55                  60

Ala Gly Lys His Met Val Gly Gly Lys Asn Val Val Gln Val Leu Asn
65                  70                  75                  80

Arg Ser Ala Phe His Asp Thr Lys Leu Val Cys Ser Gly Asp Leu Ala
                85                  90                  95

Tyr Leu Gly Gly Ser Trp Ser Lys Thr Val Gly Ser Ala Gly Glu Val
            100                 105                 110

Pro Leu Gln Gly Asp Phe Ser Ala Glu His Met Ile Phe Gly Val Glu
        115                 120                 125
```

```
Gly Ile Asp Pro Ala Arg Arg Glu Lys Leu Ile Glu Leu Leu Asp Ile
    130                 135                 140

Asp Leu Gln Trp Arg Met His Lys Val Ser Asp Gly Gln Arg Arg
145                 150                 155                 160

Val Gln Ile Cys Met Gly Leu Leu His Pro Phe Lys Val Leu Leu
                165                 170                 175

Asp Glu Val Thr Val Asp Leu Asp Val Val Ala Arg Met Asp Leu Leu
                180                 185                 190

Glu Phe Phe Lys Glu Glu Cys Glu Gln Arg Gly Ala Thr Ile Val Tyr
                195                 200                 205

Ala Thr His Ile Phe Asp Gly Leu Glu Thr Trp Ala Thr His Leu Ala
210                 215                 220

Tyr Val His Asp Gly Glu Leu Lys Arg Ser Ala Glu Thr Lys Glu Ile
225                 230                 235                 240

Glu Glu Leu Lys Thr Ser Ala Asn Leu Leu Ser Val Val Glu Asp Trp
                245                 250                 255

Leu Arg Ser Glu Thr Lys Asp Glu Asn Lys Lys Lys Lys Pro Ala
                260                 265                 270

Gln Asn Thr Ser Gln Ser Pro Phe Gly Met Ser Ser Arg His Met Ala
                275                 280                 285

Tyr Tyr Arg
    290

<210> SEQ ID NO 103
<211> LENGTH: 291
<212> TYPE: PRT
<213> ORGANISM: Noccaea caerulescens
<220> FEATURE:
<221> NAME/KEY: MISC_FEATURE
<222> LOCATION: (1)..(291)
<223> OTHER INFORMATION: ABC Transporter

<400> SEQUENCE: 103

Met Ala Ala Lys Asp Pro Thr Thr Thr Asn Asp Asp Ala Ile Arg Val
1               5                   10                  15

Ser Gly Met Glu Phe Ala Tyr Glu Val Glu Asp Pro Ile Phe Phe Asp
                20                  25                  30

Phe Ser Leu Asp Leu Pro Ser Gly Ser Arg Cys Leu Leu Val Gly Ala
            35                  40                  45

Asn Gly Ser Gly Lys Thr Thr Leu Leu Lys Ile Leu Ala Gly Lys His
    50                  55                  60

Leu Val Gly Gly Arg Asn Val Val Gln Val Leu Ser Arg Ser Ala Phe
65                  70                  75                  80

His Asp Thr Gln Leu Val Cys Ser Gly Asp Leu Ser Tyr Leu Gly Gly
                85                  90                  95

Ser Trp Ser Lys Thr Val Gly Ser Ala Gly Glu Val Pro Leu Gln Gly
                100                 105                 110

Asp Phe Ser Ala Glu Leu Met Ile Phe Gly Val Glu Gly Val Asp Pro
            115                 120                 125

Val Arg Arg Glu Lys Leu Ile Asp Leu Leu Asp Ile Asn Leu His Trp
    130                 135                 140

Arg Met His Lys Val Ser Asp Gly Gln Lys Arg Val Gln Ile Cys
145                 150                 155                 160

Met Gly Leu Leu His Pro Phe Lys Val Leu Leu Leu Asp Glu Val Thr
                165                 170                 175

Val Asp Leu Asp Val Val Ala Arg Met Asp Leu Leu Glu Phe Phe Gln
```

```
                    180                 185                 190
Glu Glu Cys Asp Gln Arg Gly Ala Thr Ile Val Tyr Ala Thr His Ile
        195                 200                 205

Phe Asp Gly Leu Glu Ala Trp Gly Thr His Leu Ala Tyr Ile Gln Asp
        210                 215                 220

Gly Glu Leu Asn Arg Ser Leu Lys Met Ala Asp Ile Asp Glu Leu Lys
225                 230                 235                 240

Thr Ser Pro Asn Leu Leu Ser Val Val Glu Ser Trp Leu Arg Ser Glu
                245                 250                 255

Thr Lys Pro Glu Lys Lys Lys Lys Lys Pro Val Ala Ala Trp Lys
            260                 265                 270

Pro Ser Pro Phe Asp Asn Ser Pro Phe Arg Ser Ser Lys His Met Ala
        275                 280                 285

Tyr Tyr Arg
290
```